US007225079B2

(12) United States Patent
Gjerde et al.

(10) Patent No.: US 7,225,079 B2
(45) Date of Patent: May 29, 2007

(54) SYSTEM AND METHOD FOR AUTOMATED MATCHED ION POLYNUCLEOTIDE CHROMATOGRAPHY

(75) Inventors: Douglas T. Gjerde, Saratoga, CA (US); Paul D. Taylor, Gilroy, CA (US); Christopher P. Hanna, San Francisco, CA (US)

(73) Assignee: Transgenomic, Inc., Omaha, NE (US)

( * ) Notice: Subject to any disclaimer, the term of this patent is extended or adjusted under 35 U.S.C. 154(b) by 543 days.

(21) Appl. No.: 10/308,576

(22) Filed: Dec. 2, 2002

(65) Prior Publication Data

US 2003/0165941 A1 Sep. 4, 2003

Related U.S. Application Data

(63) Continuation of application No. 09/469,551, filed on Dec. 22, 1999, now abandoned, which is a continuation-in-part of application No. 09/457,125, filed on Dec. 7, 1999, now abandoned, which is a continuation-in-part of application No. 09/129,105, filed on Aug. 4, 1998, now Pat. No. 6,287,822.

(51) Int. Cl.
 G06F 9/00 (2006.01)
 C12Q 1/68 (2006.01)
 C07H 21/00 (2006.01)
 B01D 15/18 (2006.01)

(52) U.S. Cl. ............................ 702/19; 435/6; 536/25.4; 210/635

(58) Field of Classification Search ...................... None
 See application file for complete search history.

(56) References Cited

U.S. PATENT DOCUMENTS

| | | | |
|---|---|---|---|
| 3,826,905 A | 7/1974 | Valkama et al. | 235/151.12 |
| 4,438,070 A | 3/1984 | Stephens et al. | |
| 4,468,331 A | 8/1984 | Antle et al. | 210/659 |
| 4,468,742 A | 8/1984 | Jenden et al. | 364/497 |
| 4,802,981 A | 2/1989 | Kenny et al. | 210/198.2 |
| 5,203,992 A | 4/1993 | Drouen | 210/198.2 |
| 5,209,853 A | 5/1993 | Lynch et al. | 210/656 |
| 5,238,557 A | 8/1993 | Schneider et al. | 210/198.2 |
| 5,350,520 A | 9/1994 | Kikumoto | 210/656 |
| 5,409,586 A | 4/1995 | Kamahori et al. | 204/182.8 |
| 5,436,166 A | 7/1995 | Ito et al. | 436/161 |
| 5,443,734 A | 8/1995 | Fetner et al. | 210/656 |
| 5,446,147 A | 8/1995 | Kung et al. | 540/595 |
| 5,459,039 A | 10/1995 | Modrich et al. | 435/6 |
| 5,508,204 A | 4/1996 | Norman | 436/161 |
| 5,585,236 A | 12/1996 | Bonn et al. | 435/5 |
| 5,633,129 A | 5/1997 | Karger et al. | 435/6 |
| 5,641,400 A | 6/1997 | Kaltenbach et al. | 210/198.2 |
| 5,670,054 A | 9/1997 | Kibbey et al. | 210/656 |
| 5,698,400 A | 12/1997 | Cotton et al. | 435/6 |
| 5,772,889 A | 6/1998 | Gjerde et al. | 210/635 |
| 5,795,976 A | 8/1998 | Oefner et al. | 536/25.4 |
| 5,830,353 A | 11/1998 | Henderson | 210/198.2 |
| 5,841,959 A | 11/1998 | Guiremand | 395/140 |
| 5,938,931 A | 8/1999 | Ono et al. | 210/656 |
| 5,955,030 A | 9/1999 | Pettit | 422/82.08 |
| 5,960,411 A | 9/1999 | Hartman et al. | 705/26 |
| 5,968,361 A | 10/1999 | Goetzinger et al. | 210/635 |
| 5,969,228 A | 10/1999 | Gorenstein | 73/23.22 |
| 5,997,742 A | 12/1999 | Gjerde et al. | 210/635 |
| 6,036,856 A | 3/2000 | Ono et al. | 210/198.2 |
| 6,197,516 B1 | 3/2001 | Altshuler et al. | 435/6 |
| 6,287,822 B1 | 9/2001 | Gjerde et al. | 435/91.2 |
| 6,366,924 B1 | 4/2002 | Parce | |

FOREIGN PATENT DOCUMENTS

| | | |
|---|---|---|
| WO | WO 99/05319 | 2/1999 |
| WO | WO 99/07899 | 2/1999 |
| WO | WO 99/19514 | 4/1999 |
| WO | WO 01/46687 | 6/2001 |

OTHER PUBLICATIONS

Strohmeier (Hewlett Packard Journal (Apr. 1990), pp. 1-11 (from online source findarticles.com).*

(Continued)

*Primary Examiner*—Lori A. Clow
(74) *Attorney, Agent, or Firm*—Licata & Tyrrell P.C.

(57) ABSTRACT

In an extensive Matched Ion Polynucleotide Chromatography (MIPC) system and method, and the computer programs or software associated therewith, the system provides automated options for sample selection, mobile phase gradient selection and control, column and mobile phase temperature control, and fragment collection for a wide variety of MIPC separation processes. MIPC separation processes can be applied to effect size-based separation of DNA fragments, mutation detection, DNA fragment purification, PCR process monitoring and other novel processes. This invention is directed to the system and software which automates many of these procedures, facilitating use of the system to achieve complex separation methods. In one embodiment of the invention, a user specifies a size range of double stranded DNA fragment(s) in a mixture, the software calculates a solvent gradient to elute the fragment(s), and the system performs the chromatographic separation using the calculated gradient. In an embodiment useful in DNA mutation detection, a user specifies the base sequence of a wild type DNA molecule, the software calculates a temperature for partially denaturing heteroduplex and homoduplex molecules of the DNA in a mixture, the software calculates a solvent gradient to elute the fragments, and the system performs the chromatographic separation using the calculated gradient and temperature.

27 Claims, 35 Drawing Sheets

OTHER PUBLICATIONS

Cooper et al., An estimate of unique DNA sequence heterozygosity in the human genome, Human Genetics 1985 69:201-205.

Cotton R., "Slowly but surely towards better scanning for mutations", TIG 1997 13:43-46.

Guyer et al., "How is the Human Genome Project doing, and what have we learned so far?", Proc. Natl. Acad. Sci. USA 1995 92:10841-10848.

Hayward-Lester et al., "Accurate and Absolute Quantitative Measurement of Gene Expression by Single-tube RT-PCR and HPLC", Genome Research 1995 5:49499.

Huber et al., "Rapid Analysis of Biopolymers on Modified Non-Porous Polystyrene—Divinylbenzene Particles", Chromatographia 1993 37(11/12):653-658.

Huber et al., "High-Resolution Liquid Chromatography of Oligonucleotides on Nonporous Alkylated Sytrene-Divinylbenzene copolymers", Anal. Biochem. 1993 212:351-358.

Liu et al., "Denaturing high performance liquid chromatography (DHPLC) used in the detection of germline and somatic mutations", Nucleic Acid Res. 1998 26(6):1396-1400.

Underhill et al., "A pre-Columbian Y chromosome-specific transition and its implications for human evolutionary history", Proc. Natl. Acad. Sci. USA 1996 93:196-200.

Underhill et al., "Detection of Numerous Y Chromosome Biallelic Polymorphisms by Denaturing High-Performance Liquid Chromatography", Genome Res. 1997 7:996.

Laboratory Methods for the Detection of Mutations and Polymorphisms, ed. G.R. Taylor, CRC Press 1997.

Baba, J. CHROMATOGER. 618:41-55 (1993).

Dadoo, R. et al. LC-GC 15:630-634 (1997).

Dao, V. et al. J Biological Chemistry 273:9202-9207 (1998).

Davidson, W. et al. J Biological Chemistry 160:13414-13426 (1985).

Dell'Anno, M. et al. Applied and Environmental Microbiology 64:3238-3245 (1998).

Devaney, J.M. et al. Analytical Chemistry 73:620-624 (2001).

Dierick, H. et al. Nucleic Acids Research 21:4427-4428 (1993).

Djordjevic N.M. et al. Analytical Chemistry 70:1921-1925 (1998).

Dolezal, M. et al. Journal of Chromatography 463:409-417 (1989).

Donis-Keller, H., et al. Nucleic Acids Research 4:2527-2538 (1977).

Drager, R.R. et al. Analytical Chemistry, 145:47-56 (1985).

Drylab® The Ultimate Tool for Serious Chromatographers http:\lcresources.com/dlmain.html (1998).

http://www.lcresources.com/dlmain.htm (Jul. 9, 1998).

http://www.nsctoronto.com/700.html (Nov. 10, 1999).

Huber, C.G. et al., Anal. Chem., 67:578-585 (1995).

Issaq et al. J. of Liquid Chromatography 12(11):2067-2082 (1989).

Jones, A. et al. Clinical Chemistry 45:8, 1133-1140(1999).

Kuklin, A et al., Molecular Biotechnology, 11:257-261 (1999).

Kuklin, A et al., Genetic Testing, 1:201-206 (1997/98).

Kuklin et al. Biomedical Products 7: 90-92 (1998).

Lerman, L. et al. Methods in Enzymology 155:483-501(1987).

Li et al. LC-GC, vol. 16 No. 5 (May 1998).

Melander et al. J of Chromatography 185: 99-109 (1979).

Metelev et al, Bioogranicheskaya Khimiya, 23:742-746 (1997).

Oefner, Peter J. et al. Human Genetics, 7.10.1-7.10.12 (1998) (Jul. 9, 1998).

Snyer, Journal of Chromatography B, 689: 105-115, (1997).

Stanford University, CA DHPLC Workshop 32-43 (1997).

Zhu et al, Journal of Chromatography A, 756: 41-50, (1996).

\* cited by examiner

FIG.—40

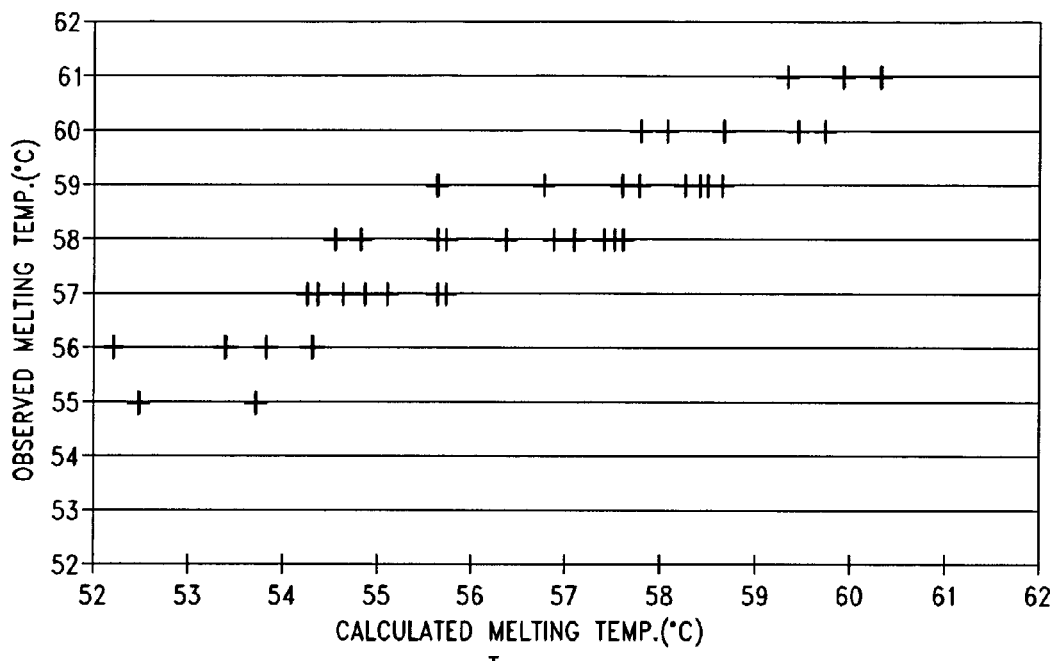
FIG.—47
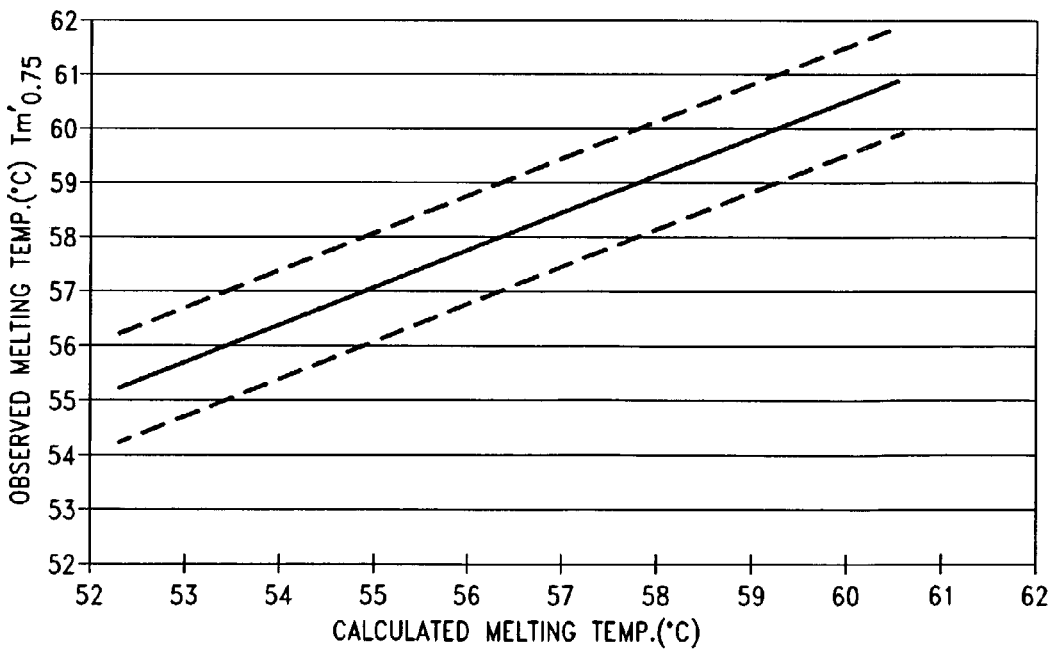
FIG.—48

SYSTEM AND METHOD FOR AUTOMATED MATCHED ION POLYNUCLEOTIDE CHROMATOGRAPHY

CROSS REFERENCE TO RELATED APPLICATIONS

This application is a continuation of application of U.S. patent application Ser. No. 09/469,551, filed Dec. 22, 1999 (now abandoned) which a continuation-in-part of U.S. patent application Ser. No. 09/457,125, filed Dec. 7, 1999 (abandoned), which is a continuation-in-part of U.S. patent application Ser. No. 09/129,105, filed Aug. 4, 1998 (now U.S. Pat. No. 6,287,822). This application is a regular U.S. patent application under 35 U.S.C. §111(a) and 35 U.S.C. §1.53(b) and claims priority from the following, commonly assigned provisional applications, each filed under 35 U.S.C. §111(b), all of which are incorporated herein by reference: 60/140,130 filed Jun. 21, 1999; 60/141,176 filed Jun. 25, 1999; and 60/146,713 filed Jul. 30, 1999.

FIELD OF THE INVENTION

This invention relates to DNA separation systems and methods suitable for effecting a size-based (base pair length) separation of DNA. In particular this invention relates to a highly automated matched ion polynucleotide chromatography (MIPC) system and method which effects size-based separation of DNA and the controls and software for operating the system.

BACKGROUND OF THE INVENTION

DNA molecules are polymers comprising sub-units called deoxynucleotides. The four deoxynucleotides found in DNA comprise a common cyclic sugar, deoxyribose, which is covalently bonded to any of the four bases, adenine (a purine), guanine (a purine), cytosine (a pyrimidine), and thymine (a pyrimidine), referred to herein as A, G, C, and T respectively. A phosphate group links a 3'-hydroxyl of one deoxynucleotide with the 5'-hydroxyl of another deoxynucleotide to form a polymeric chain. In double stranded DNA, two strands are held together in a helical structure by hydrogen bonds between what are called complementary bases. The complementarity of bases is determined by their chemical structures. In double stranded DNA, each A pairs with a T and each G pairs with a C, i.e., a purine pairs with a pyrimidine. Ideally, DNA is replicated in exact copies by DNA polymerases during cell division in the human body or in other living organisms. DNA strands can also be replicated in vitro by means of the Polymerase Chain Reaction (PCR). Sometimes, exact replication fails and an incorrect base pairing occurs. Further replication of the new strand produces double stranded DNA offspring containing a heritable difference in the base sequence from that of the parent. Such heritable changes in base pair sequence are called mutations.

As used herein, double stranded DNA is referred to as a duplex. When a base sequence of one strand is entirely complementary to a base sequence of the other strand, the duplex is called a homoduplex. When a duplex contains at least one base pair which is not complementary, the duplex is called a heteroduplex. A heteroduplex is formed during DNA replication when an error is made by a DNA polymerase enzyme and a non-complementary base is added to a polynucleotide chain being replicated. Further replications of a heteroduplex will, ideally, produce homoduplexes which are heterozygous, i.e., these homoduplexes will have an altered sequence compared to the original parent DNA strand. When the parent DNA has a sequence which predominates in a naturally occurring population, the sequence is generally referred to as a "wild type."

Many different types of DNA mutations are known. Examples of DNA mutations include, but are not limited to, "point mutation" or "single base pair mutations" in which an incorrect base pairing occurs. The most common point mutations comprise "transitions" in which one purine or pyrimidine base is replaced for another and "transversions" wherein a purine is substituted for a pyrimidine (and visa versa). Point mutations also comprise mutations in which a base is added or deleted from a DNA chain. Such "insertions" or "deletions" are also known as "frameshift mutations". Although they occur with less frequency than point mutations, larger mutations affecting multiple base pairs can also occur and may be important. A more detailed discussion of mutations can be found in U.S. Pat. No. 5,459,039 to Modrich (1995), and U.S. Pat. No. 5,698,400 to Cotton (1997).

The sequence of base pairs in DNA is a code for the production of proteins. In particular, a DNA sequence in the exon portion of a DNA chain codes for a corresponding amino acid sequence in a protein. Therefore, a mutation in a DNA sequence may result in an alteration in the amino acid sequence of a protein. Such an alteration in the amino acid sequence may be completely benign or may inactivate a protein or alter its function to be life threatening or fatal. On the other hand, mutations in an intron portion of a DNA chain would not be expected to have a biological effect since an intron section does not contain code for protein production. Nevertheless, mutation detection in an intron section may be important, for example, in a forensic investigation.

Detection of mutations is therefore of great importance in diagnosing diseases, understanding the origins of disease, and the development of potential treatments. Detection of mutations and identification of similarities or differences in DNA samples is also of critical importance in increasing the world food supply by developing diseases resistant and/or higher yielding crop strains, in forensic science, in the study of evolution and populations, and in scientific research in general (Guyer, et al., *Proc. Natl. Acad. Sci. USA* 92:10841 (1995); Cotton, *TIG* 13:43 (1997)).

Alterations in a DNA sequence which are benign or have no negative consequences are sometimes called "polymorphisms". For the purposes of this application, all alterations in the DNA sequence, whether they have negative consequences or not, are defined herein as "mutations". For the sake of simplicity, the term "mutation" is used herein to mean an alteration in the base sequence of a DNA strand compared to a reference strand (generally, but not necessarily, a wild type). As used herein, the term "mutation" includes the term "polymorphism" or any other similar or equivalent term of art.

In the prior art, size based analysis of DNA samples is accomplished by standard gel electrophoresis (GEP). Capillary gel electrophoresis (CGE) has also been used to separate and analyze mixtures of DNA fragments having different lengths, e.g., the digests produced by restriction enzyme cleavage of DNA samples. However, these methods cannot distinguish DNA fragments which have the same base pair length but have a differing base sequence. This is a serious limitation of GEP.

Mutations in heteroduplex DNA strands under "partially denaturing" conditions can be detected by gel based analytical methods such as denaturing gradient gel electrophoresis (DGGE) and denaturing gradient gel capillary electrophoresis (DGGC). The term "partially denaturing" is defined to be the separation of a mismatched base pair (caused by temperature, pH, solvent, or other factors) in a DNA double strand while other portions of the double strand remain intact, that is, are not separated. The phenomenon of "partial denaturation" occurs because a heteroduplex will denature at the site of base pair mismatch at a lower temperature than is required to denature the remainder of the strand.

These gel-based techniques are difficult and require highly skilled laboratory scientists. In addition, each analysis requires a lengthy setup and separation. A denaturing capillary gel electrophoresis analysis can only be made of relatively small fragments. A separation of a 90 base pair fragment takes more than 30 minutes. A gradient denaturing gel runs overnight and requires about a day of set up time. Additional deficiencies of gradient gels are the difficulty of adapting these procedures to isolate separated DNA fragments (which requires specialized techniques and equipment), and establishing the conditions required for the isolation. The conditions must be experimentally developed for each fragment (Laboratory Methods for the Detection of Mutations and Polymorphisms, ed. G. R. Taylor, CRC Press, 1997). The long analysis time of the gel methodology is further exacerbated by the fact that the movement of DNA fragments in a gel is inversely proportional, in a geometric relationship, to the length of the DNA fragments. Therefore, the analysis time of longer DNA fragments can often be untenable.

In addition to the deficiencies of denaturing gel methods mentioned above, these techniques are not always reproducible or accurate since the preparation of a gel and running an analysis can be highly variable from one operator to another.

Separation of double stranded nucleic acid fragment mixtures by GEP or DGGE produces a linear array of bands, each band in the array representing a separated double stranded nucleic acid component of that mixture. Since many mixtures are typically separated and analyzed simultaneously in separate lanes on the same gel slab, a parallel series of such linear arrays of bands is produced. Bands are often curved rather than straight, their mobility and shape can change across the width of the gel, and lanes and bands can mix with each other. The sources of such inaccuracies stem from the lack of uniformity and homogeneity of the gel bed, electroendosmosis, thermal gradient and diffusion effects, as well as host of other factors. Inaccuracies of this sort are well known in the GEP art and can lead to serious distortions and inaccuracies in the display of the separation results.

In addition, the band display data obtained from GEP separations is not quantitative or accurate because of the uncertainties related to the shape and integrity of the bands. True quantitation of linear band array displays produced by GEP separations cannot be achieved, even when the linear band arrays are scanned with a detector and the resulting data is integrated, because the linear band arrays are scanned only across the center of the bands. Since the detector only sees a small portion of any given band and the bands are not uniform, the results produced by the scanning method are not accurate and can even be misleading.

Methods for visualizing GEP and DGGE separations, such as staining or autoradiography are also cumbersome and time consuming. In addition, separation data is in hard copy form and cannot be electronically stored for easy retrieval and comparison, nor can it be enhanced to improve the visualization of close separations.

Separation of double-stranded deoxyribonucleic acids (dsDNA) fragments and detection of DNA mutations is of great importance in medicine, in the physical and social sciences, and in forensic investigations. The Human Genome Project is providing an enormous amount of genetic information and yielding new information for evaluating the links between mutations and human disorders (Guyer, et al., *Proc. Natl. Acad. Sci. USA* 92:10841 (1995)). For example, the ultimate source of disease is described by genetic code that differs from the wild type (Cotton, *TIG* 13:43 (1997)). Understanding the genetic basis of disease can be the starting point for a cure. Similarly, determination of differences in genetic code can provide powerful and perhaps definitive insights into the study of evolution and populations (Cooper, et. al., *Human Genetics* vol. 69:201 (1985)). Understanding these and other issues related to genetic coding requires the ability to identify anomalies, i.e., mutations, in a DNA fragment relative to the wild type.

Traditional chromatography is a separation process based on partitioning of mixture components between a "stationary phase" and a "mobile phase". The stationary phase is provided by the surface of solid materials which can comprise many different materials in the form of particles or passageway surfaces of cellulose, silica gel, coated silica gel, polymer beads, polysaccharides, and the like. These materials can be supported on solid surfaces such as on glass plates or packed in a column. The mobile phase can be a liquid or a gas in gas chromatography. This invention relates to liquid mobile phases.

The separation principles are generally the same regardless of the materials used, the form of the materials, or the apparatus used. The different components of a mixture have different respective degrees of solubility in the stationary phase and in the mobile phase. Therefore, as the mobile phase flows over the stationary phase, there is an equilibrium in which the sample components are partitioned between the stationary phase and the mobile phase. As the mobile phase passes through the column, the equilibrium is constantly shifted in favor of the mobile phase. This occurs because the equilibrium mixture, at any time, sees fresh mobile phase and partitions into the fresh mobile phase. As the mobile phase is carried down the column, the mobile phase sees fresh stationary phase and partitions into the stationary phase. Eventually, at the end of the column, there is no more stationary phase and the sample simply leaves the column in the mobile phase.

A separation of mixture components occurs because the mixture components have slightly different affinities for the stationary phase and/or solubilities in the mobile phase, and therefore have different partition equilibrium values. Therefore, the mixture components pass down the column at different rates.

Since chromatographic separations depend on interactions with the stationary phase, it is known that a separation can be improved by increasing the surface area of the stationary phase.

In traditional liquid chromatography, a glass column is packed with stationary phase particles and mobile phase passes through the column, pulled only by gravity. However, when smaller stationary phase particles are used in the column, the pull of gravity alone is insufficient to cause the mobile phase to flow through the column. Instead, pressure must be applied. However, glass columns can only withstand about 200 psi. Passing a mobile phase through a column packed with 5 micron particles requires a pressure of about 2000 psi or more to be applied to the column. 5 to 10 micron particles are standard today. Particles smaller than 5 microns are used for especially difficult separations or certain special cases). This process is denoted by the term "high pressure liquid chromatography" or HPLC.

HPLC has enabled the use of a far greater variety of types of particles used to separate a greater variety of chemical structures than was possible with large particle gravity columns. The separation principle, however, is still the same.

An HPLC-based ion pairing chromatographic method was recently introduced to effectively separate mixtures of double stranded polynucleotides in general, and DNA in particular, wherein the separations are based on base pair length (U.S. Pat. No. 5,585,236 to Bonn (1996); Huber, et al., *Chromatographia* 37:653 (1993); Huber, et al., *Anal. Biochem.* 212:351 (1993)). These references and the references contained therein are incorporated herein in their entireties. The term "Matched Ion Polynucleotide Chromatography" (MIPC) is defined herein and applied to this method because the mechanism of separation was found to be based on binding and release of the DNA from the separation surfaces rather than traditional partitioning. MIPC separates DNA fragments on the basis of base pair length and is not limited by the deficiencies associated with gel based separation methods.

Matched Ion Polynucleotide Chromatography, as used herein, is defined as a process for separating single and double stranded polynucleotides using non-polar separation media, wherein the process uses a counter-ion agent, and an organic solvent to release the polynucleotides from the separation media. MIPC separations can be complete in less than 10 minutes, and frequently in less than 5 minutes.

The MIPC separation process differs from the traditional HPLC separation processes in that the separation is not achieved by a series of equilibrium separations between the mobile phase and the stationary phase as the liquids pass through the column. Instead, the sample is fed into the column using a solvent strength which permits the sample dsDNA to bind to the separation media surface. Strands of a specific base pair length are removed from the stationary phase surface and are carried down the column by a specific solvent concentration. By passing an increasing gradient of solvent through the sample, successively larger base pair lengths are removed in succession and passed through the column. The separation is not column length or stationary phase area dependent.

This MIPC process is temperature sensitive, and precise temperature control is particularly important in the MIPC separation processes.

As the use and understanding of MIPC developed, it was discovered that when MIPC analyses were carried out at a partially denaturing temperature, i.e., a temperature sufficient to denature a heteroduplex at the site of base pair mismatch, homoduplexes could be separated from heteroduplexes having the same base pair length (U.S. Pat. No. 5,795,976; Hayward-Lester, et al., *Genome Research* 5:494 (1995); Underhill, et al., *Proc. Natl. Acad. Sci. USA* 93:193 (1996); Doris, et al., *DHPLC Workshop*, Stanford University, (1997)). These references and the references contained therein are incorporated herein in their entireties. Thus, the use of Denaturing HPLC (DHPLC) was applied to mutation detection (Underhill, et al., *Genome Research* 7:996 (1997); Liu, et al., *Nucleic Acid Res.*, 26;1396 (1998)).

DHPLC can separate heteroduplexes that differ by as little as one base pair. However, separations of homoduplexes and heteroduplexes can be poorly resolved. Artifacts and impurities can also interfere with the interpretation of DHPLC separation chromatograms in the sense that it may be difficult to distinguish between an artifact or impurity and a putative mutation (Underhill, et al., *Genome Res.* 7:996 (1997)). The presence of mutations may even be missed entirely (Liu, et al., *Nucleic Acid Res.* 26:1396 (1998)).

Important aspects of DNA separation and mutation detection by HPLC and DHPLC include the treatment of materials comprising chromatography system components; the treatment of materials comprising separation media; solvent pre-selection to minimize methods development time; optimum temperature pre-selection to effect partial denaturation of a heteroduplex during MIPC; and optimization of DHPLC for automated high throughput mutation detection screening assays. These factors are essential in order to achieve unambiguous, accurate, reproducible and high throughput DNA separations and mutation detection results.

The application of the Matched Ion Polynucleotide Chromatography (MIPC) under the partially denaturing conditions used for separating heteroduplexes from homoduplexes in mutation detection is hereafter referred to as DMIPC. In DMIPC, precise temperature control is required for maintaining both mobile and stationary phases at a partially denaturing temperature, that is, a temperature at which mismatched DNA present at the mutation site of a heteroduplex strand will denature but at which the matched DNA will remain bound into the double strand.

Certain components and operations of HPLC separation systems have been partially automated to facilitate the traditional partition-based separations. An example is the HSM control system provided by Hitachi with their HPLC chromatography apparatus. In using these controls, a chromatography expert manually inputs detailed instructions to an autosampler to obtain a specific sample for separation, detailed simple instructions to proportioning valves to effect a desired solvent gradient, and specific temperature instructions to a column oven. The control system automatically implements these instructions to effect an HPLC separation.

The MIPC systems have introduced system operation requirements which cannot be satisfied with existing control systems. Sample trays with increased numbers of wells have been introduced, requiring corresponding detailed autosampler instructions for extracting a separation aliquot of each of the samples. More complex and varied solvent concentration and gradient instructions are required. More precise temperature control is essential, and in some operations, aliquots from the same sample are to be separated at different preset temperatures.

The MIPC system can be used to isolate pure fractions, each having a single base pair size; these are needed for PCR or cloning amplification techniques. This requires use of a fragment collector operating in coordination with the MIPC separation process. Furthermore, the expanding application of MIPC separation processes requires the system be operable by a trained technician rather than a chromatography expert.

In addition, a need exists for an HPLC system which can separate DNA fragments based on size differences, and can also separate DNA having the same length but differing in base pair sequence (mutations from wild type), in an accurate, reproducible, reliable manner. Such a system should be automated and efficient, should be adaptable to routine high throughput sample screening applications, and should provide high throughput sample screening with a minimum of operator attention.

These new requirements are not satisfied by the currently available equipment and associated control systems.

SUMMARY OF THE INVENTION

It is an object of the present invention to provide a MIPC separation system and method which can be operated by a trained technician rather than a chromatography expert.

It is a further object of this invention to provide a MIPC separation system and software controls which can, for a wide variety of separation schemes, select a sample from a tray or plate containing multiple samples, set the solvent elution gradients for each separation, set the column temperature or temperatures for each separation, and collect desired fractions without continued supervision and manual control.

In one aspect, the invention concerns a method for effecting a base-pair length based separation of a mixture of DNA fragments with a high pressure liquid chromatography system comprising mobile phase flow control means for controlling the flow of solvent solution and aqueous components of a mobile phase, the flow control means including computer instruction input means; a MIPC separation column; conduit means for directing mobile phase from the mobile phase flow control means to the MIPC separation column; and a computer in communication with the mobile phase flow control means having a software mobile phase flow control module resident therein.

The method includes the computerized steps of receiving the numerical range of base-pair lengths in the mixture of DNA fragments to be separated; calculating the range of solvent concentrations and corresponding solvent gradient which will effect separation of selected fragments from the mixture of DNA fragments; providing said range of solvent concentrations and solvent gradient to the mobile phase flow control module; and conducting the separation, wherein the mobile phase flow control module controls the settings of the mobile phase flow control means to effect the gradients and solvent concentrations required to effect separation of the selected fragments. The mobile phase flow control means can include a set of flow control valves, each with automatic opening controls responsive to control commands from the flow control module. The mobile phase flow control means can include a set of pumps, the flow setting of which are responsive to control commands from the flow control module.

In the method, the base-pair length based separation can be a separation of all of the fragments of the mixture of DNA fragments or can be a separation of one or more fragments of the mixture of DNA fragments. The gradient used in the method can include an isocratic gradient.

In one embodiment of the method the solvent concentration is calculated to begin below the value of % B calculated for the smallest fragment and is calculated to end above the value of % B calculated for the largest fragment, wherein % B is calculated by the following formula:

$$\% B = p_1 + \frac{p_2 \cdot bp}{p_3 + bp}$$

% B is the percentage of an aqueous solution containing organic solvent p1, p2 and p3 are constants obtained by calibration of the chromatography system and separation column for the selected solvent with a standard mixture of DNA fragments.

In another embodiment of the method, the solvent concentration is calculated to begin below the value of % B calculated for the smallest fragment and is calculated to end above the value of % B calculated for the largest fragment, wherein % B is calculated by the following formula:

$$\% B = \frac{1}{k} \ln\left[\frac{\exp(s \cdot d \cdot k) - 1}{\text{void}}\right] + \text{offset}$$

where $$k = p_4 \cdot bp + p_5$$

$$\text{offset} = p_6 + \frac{p_7 \cdot bp}{p_8 + bp}$$

% B is a percentage of an aqueous organic solvent solution used in the mobile phase;

s is the slope of the gradient;

d, void, $p_4$, $p_5$, $p_6$, $p_7$, and $p_8$ are constants obtained by calibration of the chromatography system and separation column for the selected solvent with a standard mixture of DNA fragments.

In another aspect, the invention concerns a high pressure liquid chromatography system including a computerized control means, the chromatography system comprising mobile phase flow control means for controlling the flow of solvent solution and aqueous components of a mobile phase, the flow control means including computer instruction input means; a MIPC separation column; conduit means for directing mobile phase from the mobile phase flow control means to the MIPC separation column; and a computer in communication with the mobile phase flow control means; a software mobile phase flow control module in working association with the computer and the mobile phase flow control means, wherein the mobile phase flow control means are a set of flow control valves, each with automatic opening controls responsive to control commands from the flow control module or the mobile phase control means is a set of pumps, the flow setting of which are responsive to control commands from the flow control module, said computer including solvent concentration and gradient computing software for computing the solvent gradient beginning and ending solvent concentrations.

In one embodiment of the liquid chromatography system, the solvent concentration and gradient computing software includes software means for receiving the range of fragment base pair lengths to be separated in a mixture of DNA fragments and calculating the solvent concentration to begin below the value of % B calculated for the smallest fragment to be separated and to end above the value of % B calculated for the largest fragment to be separated, wherein % B is calculated by the following formula:

$$\% B = p_1 + \frac{p_2 \cdot bp}{p_3 + bp}$$

% B is a percentage of an aqueous organic solvent solution used in the mobile phase;

$p_1$, $p_2$ and $p_3$ are constants obtained by calibration of the chromatography system and separation column for the selected solvent with a standard mixture of DNA fragments.

In another embodiment of the high pressure liquid chromatography system the solvent concentration and gradient computing software includes software means for receiving the range of fragment base pair lengths to be separated in a mixture of DNA fragments and calculating the solvent concentration to begin below the value of % B calculated for the smallest fragment to be separated and to end above the value of % B calculated for the largest fragment to be separated, wherein % B is calculated by the following formula:

$$\% B = \frac{1}{k} \ln \left[ \frac{\exp(s \cdot d \cdot k) - 1}{\text{void}} \right] + \text{offset}$$

where $$k = p_4 \cdot bp + p_5$$

$$\text{offset} = p_6 + \frac{p_7 \cdot bp}{p_8 + bp}$$

% B is a percentage of an aqueous organic solvent solution used in the mobile phase;

s is the slope of the gradient;

d, void, $p_4$, $p_5$, $p_6$, $p_7$, and $p_8$ are constants obtained by calibration of the chromatography system and separation column for the selected solvent with a standard mixture of DNA fragments.

In yet another aspect, the invention concerns a software program including means for receiving a range of base pair lengths to be separated from a mixture of DNA fragments, means for calculating solvent concentrations required to separate the range of base pair lengths to be separated by MIPC, and means for selecting the solvent gradient to be used to separate the range of base pair lengths to be separated by MIPC, wherein the means for calculating said solvent concentrations includes means for calculating the solvent concentration to begin below the value of % B calculated for the smallest fragment to be separated and to end above the value of % B calculated for the largest fragment to be separated, wherein % B is calculated by the following formula:

$$\% B = p_1 + \frac{p_2 \cdot bp}{p_3 + bp}$$

% B is a percentage of an aqueous organic solvent solution used in the mobile phase $p_1$, $p_2$ and $p_3$ are constants obtained by calibration of the chromatography system and separation column for the selected solvent with a standard mixture of DNA fragments.

In another aspect the invention concerns a software program including means for receiving a range of base pair lengths to be separated from a mixture of DNA fragments, means for calculating solvent concentrations required to separate the range of base pair lengths to be separated by MIPC, and means for selecting the solvent gradient to be used to separate the range of base pair lengths to be separated by MIPC, wherein the means for calculating said solvent concentrations includes means for calculating the solvent concentration to begin below the value of % B calculated for the smallest fragment to be separated and to end above the value of % B calculated for the largest fragment to be separated, wherein % B is calculated by the following formula:

$$\% B = \frac{1}{k} \ln \left[ \frac{\exp(s \cdot d \cdot k) - 1}{\text{void}} \right] + \text{offset}$$

where $$k = p_4 \cdot bp + p_5$$

$$\text{offset} = p_6 + \frac{p_7 \cdot bp}{p_8 + bp}$$

% B is a percentage of an aqueous organic solvent solution used in the mobile phase;

s is the slope of the gradient;

d, void, $p_4$, $p_5$, $p_6$, $p_7$, and $p_8$ are constants obtained by calibration of the chromatography system and separation column for the selected solvent with a standard mixture of DNA fragments.

In another aspect, the invention concerns a method for effecting a separation of equal length heteroduplex and homoduplex DNA molecules in a mixture, with a high pressure liquid chromatography system. The system includes a Matched Ion Polynucleotide Chromatography separation column; oven temperature control means for controlling the temperature of mobile phase entering the column, the oven temperature control means including computer instruction input means; and a computer in communication with the oven temperature control means having a oven temperature control software module resident therein. This method includes the computerized steps of performing a temperature titration which includes analyzing the mixture by Denaturing Matched Ion Polynucleotide chromatography in a series of Denaturing Matched ion Polynucleotide Chromatography separations in the temperature range of about 50° C. to about 75° C., each successive separation having a higher temperature than the preceding separation until a mutation separation profile is observed or the absence of any mutation separation profile in the mutation separation temperature range is observed, wherein a mutation separation profile identifies the presence of a mutation and the absence of a mutation separation profile indicates an absence of mutation in the sample.

Alternatively, analyzing the mixture by Denaturing Matched Ion Polynucleotide Chromatography in a series of Denaturing Matched Ion Polynucleotide Chromatography separations in the temperature range of 50° C. to about 75° C., each successive separation having a lower temperature than the preceding separation until a mutation separation profile is observed or the absence of any mutation separation profile in the mutation separation temperature range is observed, wherein a mutation separation profile identifies the presence of a mutation and the absence of a mutation separation profile indicates an absence of mutation in the sample.

In this method, the oven temperature control module controls the settings of the oven temperature control means to effect the temperature during the successive separations. The oven temperature control means in this aspect of the invention can include the following embodiments. First, an air bath oven having a re-circulating air temperature control system; a length of capillary tubing having an inlet end and an outlet end, the outlet end of the capillary tubing being connected with the inlet end of the separation column, and the inlet end of the capillary tubing comprising means for receiving process liquid, the tubing having a fully extended length of from 6 to 400 cm; and the separation column and the coil of capillary tubing being enclosed in the air bath oven and exposed to air therein, the temperature control system responsive to control commands from the oven temperature control module.

Second, a heat conducting block having a first heat transfer surface, a separation column receptacle, and a capillary coil receptacle; a separation column positioned within the separation column receptacle in heat conducting relationship with an inner wall thereof; and a coil of capillary tubing positioned in the capillary coil receptacle, the outer extremities of the coil being in heat conducting relationship with an inner wall of the capillary coil receptacle, the temperature control system responsive to control commands from the oven temperature control module. A Peltier heating and cooling unit can be provided in heat conducting relationship with the first heat transfer surface.

In another aspect, the invention concerns a method for effecting a separation of equal length heteroduplex and homoduplex DNA molecules in a mixture, with a high pressure liquid chromatography system. The system includes a Matched Ion Polynucleotide Chromatography separation column; oven temperature control means for controlling the temperature of mobile phase entering the separation column, the oven temperature control means including computer instruction input means; and a computer in communication with the oven temperature control means having a oven temperature control software module resident therein.

The method includes the following computerized steps: a) receiving a predicted heteromutant site separation temperature; b) heating the mixture of DNA molecules to the predicted heteromutant site separation temperature; c) analyzing the product of step (b) with Denaturing Matched Ion Polynucleotide Chromatography at the predicted heteromutant site separation temperature to identify the presence of any heteromutant site separated components therein.

In the method, the predicted heteromutant site separation temperature can be obtained by the steps of: a) a calculation step for obtaining a calculated heteromutant site separation temperature; b) a prediction step for obtaining the predicted heteromutant site separation temperature; wherein the calculation step comprises calculating the calculated heteromutant site separation temperature according to a first mathematical model; wherein the prediction step comprises adjusting the calculated heteromutant site separation temperature according to a second mathematical model; wherein the second mathematical model is based on a comparison of empirically determined heteromutant site separation temperatures with calculated heteromutant site separation temperatures.

In an embodiment of this aspect of the invention, the predicted heteromutant site separation temperature is calculated by the following formula: $T(hsst)=X+m\cdot T(w)$, wherein $T(hsst)$ is the predicted heteromutant site separation temperature, $T(w)$ is the temperature calculated by software or determined experimentally, at which there is a selected equilibrium between denatured and non-denatured states of the wild type double stranded DNA, X is the Denaturing Matched Ion Polynucleotide Chromatography detection factor, and m is a weighting factor selected between 0 and 2.

In another aspect, the invention relates to a denaturing high pressure liquid chromatography system including a computerized control means, the chromatography system comprising a Matched Ion Polynucleotide Chromatography separation column; oven temperature control means for controlling the temperature of the mobile phase entering the separation column, the temperature control means including computer instruction input means; conduit means for directing mobile phase the MIPC separation column; a computer in communication with the oven temperature control means; a oven temperature control software module in working association with the computer and the oven temperature control means, the computer including temperature computing software for computing the heteromutant site separation temperature for the separation of equal length heteroduplex and homoduplex DNA molecules in a mixture.

In the system, the Matched Ion Polynucleotide Chromatography separation column includes an inlet end, and the oven temperature control means includes: an air bath oven having a re-circulating air temperature control system; a length of capillary tubing having an inlet end and an outlet end, the outlet end of the capillary tubing being connected with the inlet end of the separation column, and the inlet end of the capillary tubing comprising means for receiving process liquid, the tubing having a fully extended length of from 6 to 400 cm; and the separation column and the coil of capillary tubing being enclosed in the air bath oven and exposed to air therein, the temperature control system responsive to control commands from the oven temperature control module.

Alternatively, the oven temperature control means can include: a heat conducting block having a first heat transfer surface, a separation column receptacle, and a capillary coil receptacle; a separation column positioned within the separation column receptacle in heat conducting relationship with an inner wall thereof; and a coil of capillary tubing positioned in the capillary coil receptacle, the outer extremities of the coil being in heat conducting relationship with an inner wall of the capillary coil receptacle, the temperature control system responsive to control commands from the oven temperature control module. A Peltier heating and cooling unit can be provided in heat conducting relationship with the first heat transfer surface.

In yet another aspect, the invention provides a software program including means for receiving the base pair length of equal length heteroduplex and homoduplex DNA molecules in a mixture to be separated, means for calculating a heteromutant site separation temperature required for the separation of the equal length heteroduplex and homoduplex DNA molecules by Denaturing Matched Ion Polynucleotide Chromatography, wherein the heteromutant site separation temperature is calculated by the following formula: $T(hsst)=X+m\cdot T(w)$, wherein $T(hsst)$ is the heteromutant site separation temperature, $T(w)$ is the temperature calculated by software or determined experimentally, at which there is a selected equilibrium between denatured and non-denatured states of the wild type double stranded DNA, X is the Denaturing Matched Ion Polynucleotide Chromatography detection factor, and m is a weighting factor selected between 0 and 2.

In another aspect, the invention concerns a method for effecting a separation of equal length heteroduplex and homoduplex DNA molecules in a mixture, with a high pressure liquid chromatography system. The system includes mobile phase flow control means for controlling the flow of solvent solution and aqueous components of a mobile phase, the flow control means including computer instruction input means; a MIPC separation column; conduit means for directing mobile phase from the mobile phase flow control means to the MIPC separation column; and a computer in communication with the mobile phase flow control means having a software mobile phase flow control module resident therein.

The method includes the computerized steps of (a) receiving the numerical value of the base-pair length of a DNA molecule having the length of a non-denatured homoduplex or heteroduplex molecule in the mixture; (b) calculating a solvent concentration which will effect elution of a molecule having the base-pair length from the column under non-denaturing conditions; (c) calculating a range of solvent concentrations and corresponding solvent gradient which will effect the separation under conditions effective to partially denature the heteroduplexes; (d) providing the range of solvent concentrations and solvent gradient to the mobile phase flow control module; and (e) conducting the separation, wherein the mobile phase flow control module controls the settings of the mobile phase flow control means to effect the gradients and solvent concentrations required to effect separation of the selected fragments. The mobile phase flow control means can be a set of flow control valves, each with automatic opening controls responsive to control commands from the flow control module, or can be a set of pumps, the flow setting of which are responsive to control commands from the flow control module.

In the method, the gradient can be an isocratic gradient. Also in the method, the solvent concentration can be calculated to begin below the value of % B calculated for a DNA molecule having the base-pair length and calculated to end above the value of % B calculated for a DNA molecule of the base-pair length, wherein % B is the percentage of an aqueous solution containing organic solvent, wherein % B is calculated by a linear, hyperbolic, quadratic or cubic formula having constants obtained by calibration of the chromatography system and separation column for the selected solvent with a standard mixture of DNA fragments.

In still another aspect, the invention relates to a denaturing high pressure liquid chromatography system including a computerized control means. The chromatography system includes a mobile phase flow control means for controlling the flow of solvent solution and aqueous components of a mobile phase, the flow control means including computer instruction input means; a MIPC separation column; conduit means for directing mobile phase from the mobile phase flow control means to the MIPC separation column; and a computer in communication with the mobile phase flow control means; a software mobile phase flow control module in working association with the computer and the mobile phase flow control means, wherein the mobile phase flow control means are a set of flow control valves, each with automatic opening controls responsive to control commands from the flow control module or the mobile phase control means is a set of pumps, the flow setting of which are responsive to control commands from the flow control module, the computer including solvent concentration and gradient computing software for computing the solvent gradient beginning and ending solvent concentrations for the separation of equal length heteroduplex and homoduplex DNA molecules in a mixture.

In the system, the solvent concentration and gradient computing software can include software means for receiving the base-pair length of a homoduplex or a heteroduplex molecule in the mixture and calculating the solvent concentration to begin below the value of % B calculated for a DNA molecule having the base-pair length and is calculated to end above the value of % B calculated for a DNA molecule of the base-pair length, wherein the % B is the percentage of an aqueous solution containing organic solvent, wherein the % B is calculated by a linear, hyperbolic, quadratic or cubic formula having constants obtained by calibration of the chromatography system and separation column for the selected solvent with a standard mixture of DNA fragments.

In still yet another aspect, the invention concerns a software program which includes means for receiving the base pair length of equal length heteroduplex and homoduplex DNA molecules in a mixture to be separated, means for calculating a solvent concentration required to elute a DNA molecule having the base-pair length by MIPC, and means for selecting the solvent gradient to be used to separate the heteroduplex and homoduplex DNA molecules under partially denaturing conditions.

The means for calculating the solvent concentration includes means for calculating the solvent concentration to begin below the value of % B calculated for a DNA molecule having the base-pair length and is calculated to end above the value of % B calculated for a DNA molecule of the base-pair length, wherein the % B is the percentage of an aqueous solution containing organic solvent, wherein the % B is calculated by a linear, hyperbolic, quadratic or cubic formula having constants obtained by calibration of the chromatography system and separation column for the selected solvent with a standard mixture of DNA fragments.

In one embodiment of the software % B is calculated by the following formula:

$$\% \ B = p_1 + \frac{p_2 \cdot bp}{p_3 + bp}$$

where $p_1$, $p_2$ and $p_3$ are constants obtained by calibration of the chromatography system and separation column for the selected solvent with a standard mixture of DNA fragments.

In another embodiment % B is calculated by the following formula:

$$\% \ B = \frac{1}{k} \ln\left[\frac{\exp(s \cdot d \cdot k) - 1}{\text{void}}\right] + \text{offset}$$

where $k = p_4 \cdot bp + p_5$ $$\text{offset} = p_6 + \frac{p_7 \cdot bp}{p_8 + bp}$$

s is the slope of the gradient;
d, void, $p_4$, $p_5$, $p_6$, $p_7$, and $p_8$ are constants obtained by calibration of the chromatography system and separation column for the selected solvent with a standard mixture of DNA fragments.

BRIEF DESCRIPTION OF THE DRAWINGS

FIG. 47 is a graph of calculated melting temperature versus empirically determined melting temperature.

FIG. 48 is a graph of calculated melting temperature versus predicted melting temperature.

DETAILED DESCRIPTION OF THE INVENTION

The objects of this invention are provided in an extensive MIPC system and method and the computer programs or software associated therewith. The system provides automated options for sample selection, mobile phase gradient selection and control, column and mobile phase temperature control, and fragment collection for a wide variety of MIPC separation processes of this invention. As described in earlier, copending and commonly assigned U.S. patents or patent applications (U.S. Pat. Nos. 5,772,889; 5,997,742; 5,972,222; U.S. patent application Ser. No. 09/183,123 filed Oct. 30, 1998 (now U.S. Pat. No. 6,066,258); Ser. No. 09/183,450 filed Oct. 30, 1998 (now U.S. Pat. No. 6,056,877); Ser. No. 09/350,737 filed Jul. 9, 1999 (now U.S. Pat. No. 6,030,527); Ser. No. 09/080,547 May 18, 1998 (now U.S. Pat. No. 6,017,457), each of which is incorporated by reference in its entirety herein) MIPC separation processes can be applied to effect size-based separation of DNA fragments, mutation detection, DNA fragment purification, PCR process monitoring and other novel processes. This invention is directed to the system and software which automates many of these procedures, facilitating use of the system to achieve complex separation methods.

Figure 1:
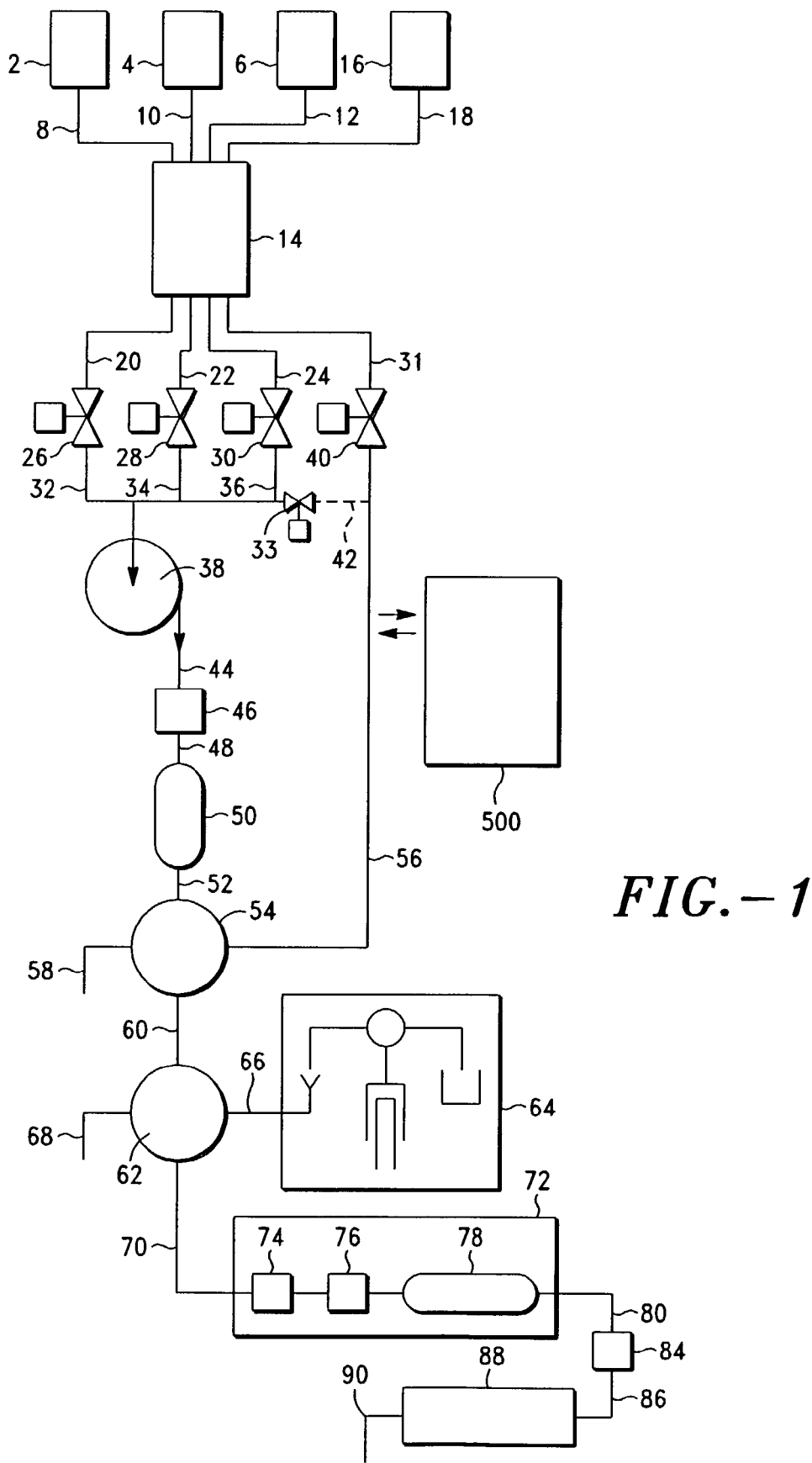
FIG. 1 is a schematic representation of a single column MIPC system using valves and valve controls to establish elution solvent gradients.

FIG. 1 is a schematic layout of the system in accordance with one embodiment of the present invention. A plurality of containers can be used as reservoirs for solutions which make up the mobile phase. For example, container 2 can contain an aqueous component of a mobile phase such as an aqueous solution of counter ion agent (e.g., triethylammonium acetate (TEAA)), and container 4 can contain an aqueous solution of counterion agent plus organic (driving) solvent (e.g., TEAA plus acetonitrile).

For purposes of simplifying the description of the invention, and not by way of limitation, the aqueous solution in container 2 will be referred to as solution A and the solution containing organic solvent in container 4 will be referred to as solution B. An auxiliary liquid (e.g., a co-solvent) can be held in container 6. These solutions are mixed to achieve a selected concentration of organic solvent in the mobile phase during a separation. Other examples of these solutions are provided in the Examples herein and in the commonly assigned patent indicated hereinabove. The containers have respective transport tubing such as counter-ion solution transport tubing 8, solvent solution transport tubing 10 and auxiliary liquid transport tubing 12 communicating therewith and leading to degasser 14.

The term polynucleotide is defined as a linear polymer containing an indefinite number of nucleotides, linked from one ribose (or deoxyribose) to another via phosphoric residues. The present invention can be used in the separation of double- or single-stranded DNA or RNA. For purposes of simplifying the description of the invention, and not by way of limitation, the separation of double-stranded DNA will be described in the examples herein, it being understood that all polynucleotides are intended to be included within the scope of this invention.

The degasser 14 removes dissolved gases from the liquids. An example of a suitable degasser is the Degassit Model 6324. Removal of dissolved oxygen is particularly important because its presence increases the risk of oxidizing ferrous or other oxidizable metals in the system components and thus introducing the corresponding cations into the mobile phase liquid.

Figure 2:
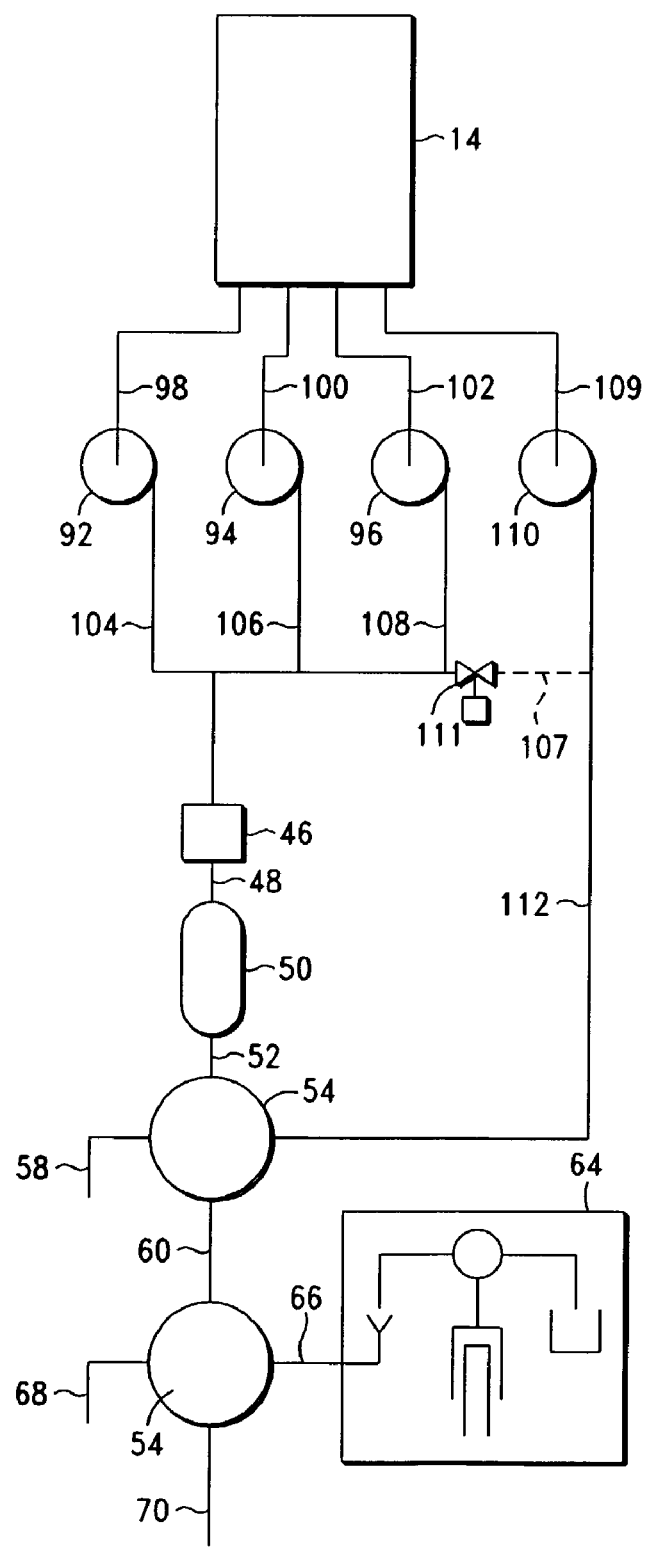
FIG. 2 is a partial schematic representation of a pump system for establishing elution solvent gradients.

Column cleaning solution is contained in cleaning solution container 16 which likewise has a cleaning solution transport conduit 18 communicating therewith leading to the degasser 14. In this embodiment, the cleaning solution can flow by gravity pressure if the container 16 is elevated above the degasser and injection valve 54. Alternatively, a pump 110 as shown in FIG. 2 can be provided to achieve cleaning solution flow.

The system of the invention incorporates conventional mobile phase flow control means which controls flow of solvent solution and aqueous components of an mobile phase.

In one embodiment, the mobile phase flow control means comprises a set of flow control valves, each with automatic opening controls under computer control as described hereinbelow.

In another embodiment the mobile phase flow control means comprises a set of pumps, the flow setting of which are responsive to computer control as described hereinbelow.

The system illustrated in FIG. 1 utilizes one embodiment of a mobile phase flow control means which includes a set of flow control valves. Degassed counterion solution conduit 20, degassed solvent solution conduit 22, and degassed auxiliary liquid conduit 24 leading from the degasser 14 communicate with respective aqueous component proportioning valve 26, solvent solution proportioning valve 28, and auxiliary liquid proportioning valve 30. The settings for these proportioning valves are set and changed by valve operators such as stepper motors associated therewith, and these valve operators respond to establish a desired set of settings in response to commands from the mobile phase flow control software module described in greater detail hereinbelow. The flow control valves 26, 28, and 30 comprise an embodiment of a mobile phase flow control means which controls the flow of solvent solution and other components of the mobile phase. The settings for these valves control the ratio of liquids (co-solvents, solvent solution, etc.) through the injector valve and the separation column. Conduits 32, 34, and 36 lead from respective proportioning valves 26, 28 and 30 to the intake of pump 38.

The cleaning solution transport conduit 31 leads to a cleaning solution valve 40. An optional cleaning solution conduit 42 leads from the valve 40 and communicates with the inlet of pump 38. Valve 33 controls flow through conduit 42.

The openings of valves 26, 28 and 30 accurately set the relative ratios of the organic solvent, and other components, within the mobile phase, a most important part of this system because the size-based DNA separation by MIPC is a function of solvent concentration. As will be described in regard to the various DNA fragment separation processes, the slope of the organic solvent gradient as a function of time is changed during the separation process, and the most critical phase may require a very precise gradient, or for some processes, a highly precise isocratic (constant solvent concentration) composition. The settings of the valves 26, 28 and 30 are established by conventional valve actuators which can be remotely set by signals to a conventional valve control device. As will be described in greater detail hereinbelow, the Instrument Control Software of the instant invention provides computer controlled instructions which establish the settings of valves 26, 28 and 30 to precise flow values at appropriate times during the operation of the system.

In a similar manner, the Instrument Control Software of the instant invention provides computer controlled instructions to establish the operational parameters of the pump 38, such as the off/on status of the pump and the pressure or flow rate settings of the pump.

Pump outflow conduit 44 communicates with the in-line mixer 46, directing the liquid flow through the mixer 46 for thorough mixing of the components. Mixed liquid outflow conduit 48 communicates with optional guard column 50 to treat the mixed liquid to remove multivalent metal cations and other contaminants which would interfere with the separation of DNA fragments. Guard column 50 can contain a cation exchange resin in sodium or hydrogen form for removal of multivalent metal cations by conventional ion exchange. Conduit 52 communicates with the outlet of the guard column and an inlet port of a cleaning solution injector valve 54. Cleaning solution supply conduit 56 connects valve 40 with the cleaning solution injector valve 54, and waste outlet conduit 58 leads to waste. Conduit 60 leads from valve 54 to the sample injection valve 62.

Sample aliquot selector 64 communicates with injector valve 62 through sample conduit 66. Waste conduit 68 leads from the injector valve and removes waste liquids. Details about the sample aliquot selector 64 are provided in greater detail hereinbelow with respect to FIG. 3, and details about the cleaning solution and sample injector valves 54 and 62 and their operation are presented in greater detail hereinbelow with regard to FIGS. 4-8.

In the injector valve 62, the sample is introduced into a stream of solvent and carrier liquid passing through the valve from conduit 60. Sample conduit 70 communicates with an outlet port of injector valve 62 and with the column prefilter 74 in the air bath oven 72. The capillary tubing coil 76 communicates with the prefilter 74 and the inlet of separation column 78. The extended length of the capillary coil 76 allows ample heat to pass from the heated oven air into the liquid passing through the coil, bringing the liquid within ±0.05° C. of a selected temperature. The oven 72 establishes this temperature uniformity in the prefilter 74, coil 76, and separation column 78.

The separation column 78 is packed in a conventional column construction with beads having a unique separation surface which effects a size-based separation of DNA fragments in the presence of a counter-ion by the MICP process. The separation process and details about the beads are described in detail hereinbelow. A stream of mobile phase containing base pair length size-separated DNA fragments passes from the separation column 78 through conduit 80.

Conduit 80 communicates with a detector 84. The detector can be a conventional UV transmission device which measures the UV transmission of the DNA fragment structures in the liquid mobile phase. The absorbance is a function of the concentration of the DNA fragments in the liquid being tested.

Alternatively, if the DNA can be labeled with a fluorescent marker, the detector can be a fluorescence detector which can continuously measure the level of the fluorescent marker in the liquid by detecting the emission level at the frequency most appropriate for the marker. It will be readily apparent that any detecting system capable of continuously measuring a characteristic of the liquid which is a function of the concentration of the DNA fragments therein is suitable and intended to be within the scope of this invention.

Conduit 86 removes the tested liquid. Examples of suitable detectors include the L-7420 UV-Vis detector, and the L-7480 Fluorescence detector available from Hitachi. The electrical output from the detector preferably is converted to a digital form by an A/D converter and recorded in standard digital format to a digital storage device such as a disk drive in computer 500.

Then, the mobile phase passes to the fragment collector 88 described in greater detail hereinbelow with respect to FIGS. 14-24. In the fragment collector 88, selected portions of the mobile phase containing a separated DNA fraction are collected in vials for later processing or analysis. Uncollected fractions are removed through waste conduit 90.

The DNA separation process is impaired by the presence of multivalent cations. In the above description, the liquid flow system is described as a series of conduits. The conduits are capillary tubing selected to avoid introduction of multivalent cations into the liquids. The preferred capillary tubing materials are titanium and PEEK. For similar reasons, the other components of the system are preferably made of titanium or PEEK or have the surfaces exposed to the liquid coated with PEEK to protect them from oxidation and prevent the introduction of multivalent cations into the liquid. Stainless steel can also be used provided it has been treated to remove all oxidized surface materials and the solutions contacting the stainless steel surfaces are free of dissolved oxygen.

Illustrating another embodiment of a mobile phase flow control means, FIG. 2 is a partial schematic representation of a pump system for establishing mobile phase composition. This system relies on proportioning pumps to control the ratio of aqueous component and solvent solution, such as solutions A and B described hereinabove. The inlets of proportioning pumps 92, 94 and 96 by way of their respective supply conduits 98, 100, and 102 communicate with the degasser 14, and by way of their respective outlet conduits 104, 106 and 108 communicate with the inline mixer 46. The operational speed for these proportioning pumps are calibrated to flow rates therethrough and are controlled by a flow control software module described in greater detail hereinbelow. The settings for these proportioning valves control the liquid flow speed and the ratio of liquids (co-solvents, driving solvents, etc.) through the injector valve and the separation column.

A pump 110 can supply cleaning solution to the system through optional conduit 112. An optional conduit 107 leads from conduit 112 and communicates with the in-line mixer 46. Valve 111 controls flow through conduit 107.

Examples of suitable mobile phase control means for use in the invention include the programmable dual piston pump Model L-7100 available from Hitachi and the Model 2690 Separations Module available from Waters.

Figure 3:
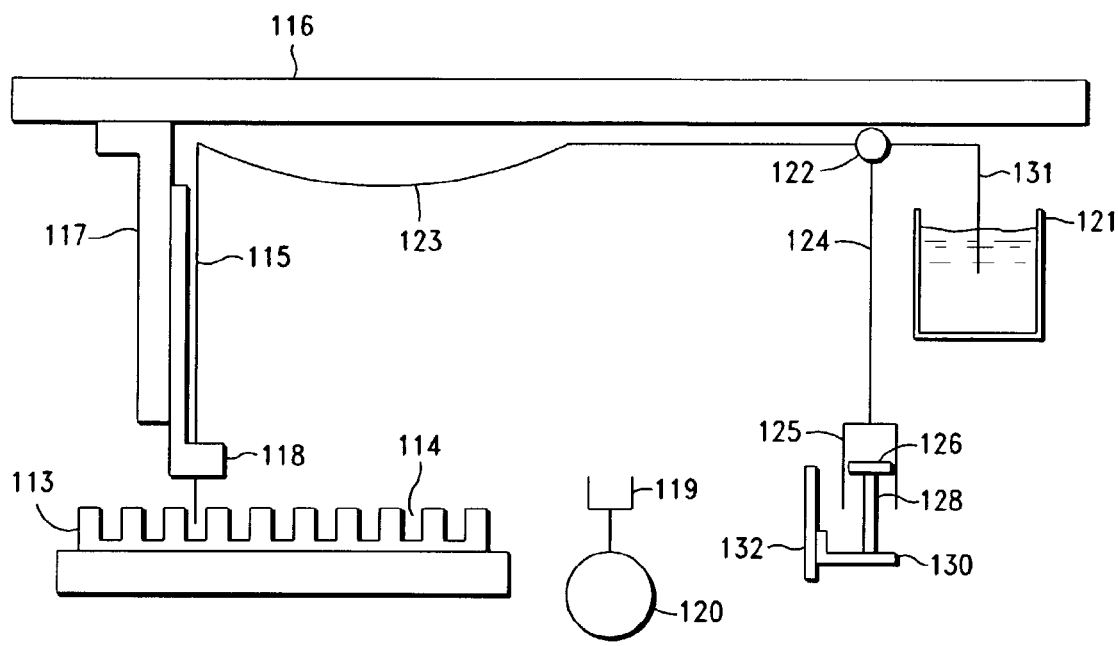
FIG. 3 is a schematic representation of an autosampler subsystem used in the MIPC system.

FIG. 3 is a schematic representation of an autosampler subsystem used in the MIPC system. This autosampler removes an aliquot having a predetermined volume from a selected well or vial (e.g., micro-centrifuge tube) supported in a multi-well 113. Microwell plates can have any predetermined number of wells 114 having a precise dimensional position for each well, such as the standard 96 well multi-well plate. The sampling needle 115 is supported on a sampling carriage 116. The sampling carriage 116 has a needle support 118 mounted for vertical movement on vertical support 117. Vertical support 117 is mounted for lateral movement on carriage 116. Lateral movement of the support 117 positions the needle above a selected well or the injector port 119 of injection valve 120. The flexible tubing 123 is mounted in sealed engagement with the needle 115 at one end and with the syringe needle 124 at the other end.

The syringe needle 124 communicates with the inner volume of the syringe cylinder 125. The piston 126 is mounted on the syringe actuator rod 128 and forms a sealed engagement with the inner wall of the cylinder 125.

In operation, vertical upward movement of the syringe actuator rod 128 displaces liquid in the cylinder 125, and vertical downward movement of the syringe actuator rod 128 pulls liquid into the syringe. Rod 128 is attached to clamp 130 which is supported for movement along guide element 132. When valve 122 is positioned to provide communication between the needle 124 and the tubing 123, the downward movement of the piston 126 pulls sample into the needle 115 from a well 114. When needle 115 is positioned above injector valve port 119, upward movement of the piston 126 discharges sample from needle 115 into port 119.

Conduit 131 extends from valve 122 to the cleaning solution reservoir 121. When valve 122 is in the position providing communication between the needle 124 and the conduit 131, the downward movement of the piston 126 draws cleaning solution into the needle. When the needle 115 is positioned above the injector port 119 and valve 122 is positioned to provide communication between the needle 124 and the conduit 123, upward movement of the piston 126 discharges cleaning solution into the injector port 119. Examples of suitable auto-samplers include the HITACHI Model L-7250 Programmable Autosampler and the HTS PAL High Throughput Autosampler (Shimadzu, Columbia, Md.).

The autosampler operation includes the following control sequences:
1. Move the sampling needle 115 to the programmed X-Y coordinate of the center of a selected well 114.
2. Lower the sampling needle 115 a programmed distance to lower the needle into liquid in a selected well 114.
3. Downward vertical movement of the syringe rod 128 a programmed distance to draw a predetermined volume of sample into the needle 115.
4. Raising the needle 115 to a distance above the top of the microtiter plate 113.
5. Moving the needle 115 to the position of the injector port 119.
6. Lowering the needle 115 to the injector port 119.
7. Upward vertical movement of the syringe rod 128 to dispel the sample from the needle 115 into the injector port 119.
8. Movement of valve 122 to connect the needle 124 to the cleaning solution 121.
9. Downward movement of the piston 126 to draw cleaning solution into the syringe.
10. Movement of valve 122 to connect the needle 124 to the conduit 123.
11. Upward movement of the piston 126 to discharge cleaning solution into the injection port 119.
12. At the beginning of the next DNA separation, Steps 1-11 are repeated.

Figure 4:
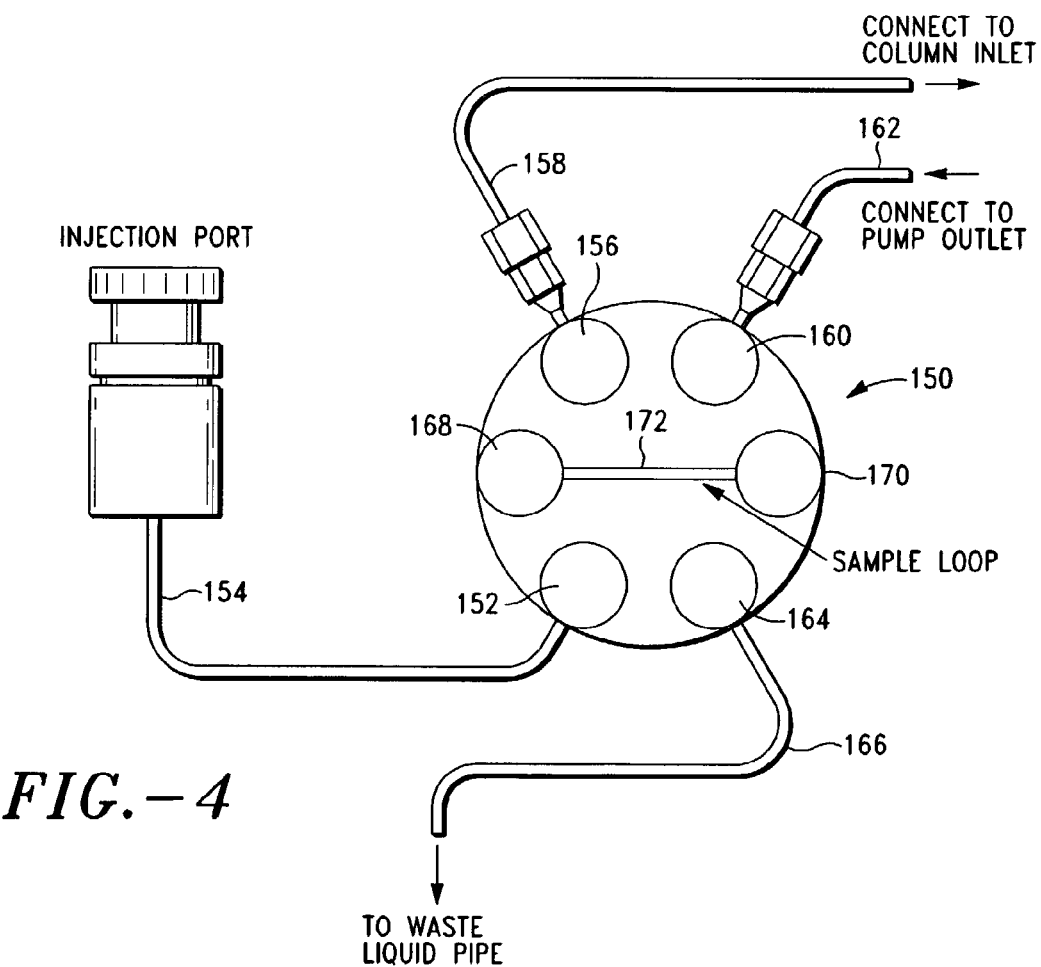
FIG. 4 is schematic representation of an injection valve used in the MIPC system.

FIG. 4 is schematic representation showing the structure of the sample injection valve and cleaning solution injection valve for use in the MIPC system. The same valve structure can be used for both the sample injection and cleaning solution injection. The injection valve 150 is a six-port, rotary valve operated by a conventional valve motor such as a stepper motor (not shown). Exemplary valves include the LabPRO valves available from RHEODYNE (Cotati, Calif.). The valve has six external ports permanently connected to inlet and outlet conduits. External port 152 is connected with an injection line 154 for receiving a sample to be analyzed. External port 156 is connected with a column supply conduit 158 communicating with the separation column 78 (FIG. 1). External port 160 is connected with an inlet conduit 162 communicating with the outlet of pump 38 (FIG. 1). External port 164 is connected with a waste conduit 166. Opposed outlet ports 168 and 170 communicate with the opposed sample inlet and outlet ends of a sample loop 172.

During the injection of cleaning solution, the valve injects a block of cleaning solution into the solvent stream, regenerating and cleaning the separation column and other components downstream of the injection, removing from the surfaces accumulated residues and any residual DNA remaining from prior separations.

The connections between the external ports and internal passages, and their operation in the cleaning solution injector valve 54 and sample injector valve 62 in FIG. 1 is described in FIGS. 5-8. The description hereinbelow is presented for the sample injection valve 62, but the same relationships and operation apply to the cleaning solution injection valve with the exception of the liquids being injected and their source.

Figure 5:
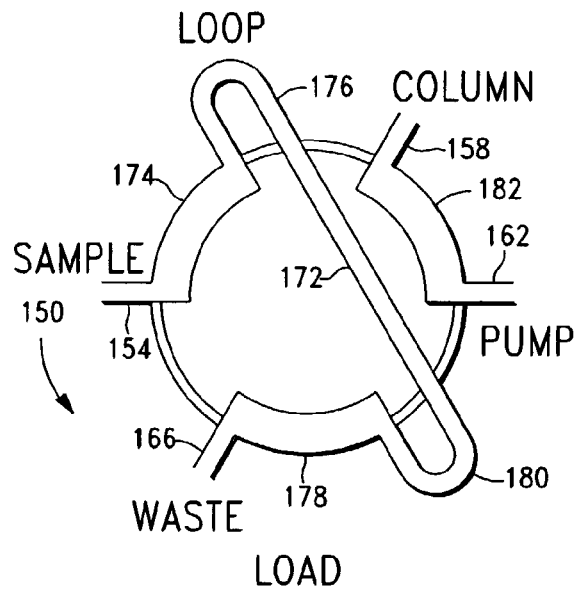
FIG. 5 is a schematic representation of an injection valve in the filled loop load position.
Figure 6:
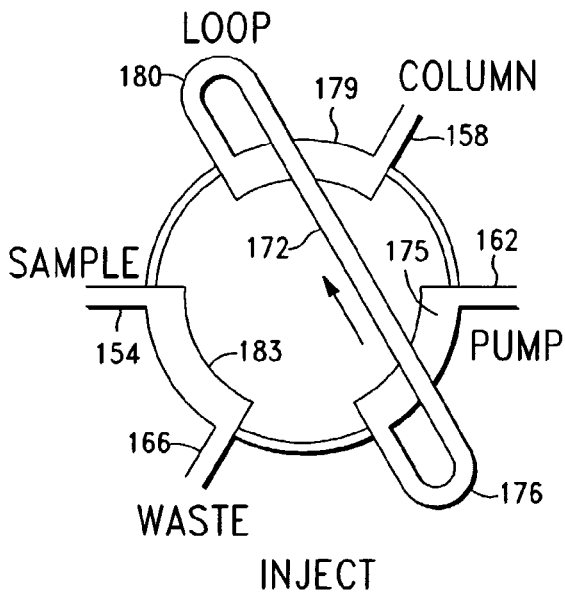
FIG. 6 is a schematic representation of an injection valve in the filled loop injection position.

FIGS. 5 and 6 describe the use of the valve for filled loop injection, the mode used when a larger volume of sample (or cleaning solution) is to be injected. FIG. 5 is a schematic representation of an injection valve in the sample load position, and FIG. 6 is a schematic representation of the injection valve in the injection position. In the load position shown in FIG. 5, a first internal passageway 174 of the valve connects the first end 176 of loop 172 with the sample injection line 154, and a second internal passageway 178 connects the second end 180 of loop 172 with the waste conduit 166. A third internal passageway 182 connects the pump outlet conduit 162 with the conduit 158 to the separation column 78. While sample from the injection port 154 is introduced into the sample loop 172 through passageway 174, any surplus or liquid in the loop 172 is expelled to the waste conduit 166 through passageway 178. Simultaneously, mobile phase solutions flow from the pump conduit 162 to the separation column 78 through third conduit 182.

Rotation of the valve in the direction of arrow 150 to the injection position shown in FIG. 6 moves the internal passageways to establish a different set of connections with the inlet and outlet conduits. Passageway 179 connects one end 180 of the loop 172 with the conduit 158 leading to the separation column, and passageway 175 connects the other end 176 of the loop 172 with the inlet conduit 162 leading to the pump. Mobile phase solution from the pump enters passageway 175 and passes through the loop 172, expelling sample solution into the conduit 158 leading to the column and continues to rinse the loop, carrying any residue into the column conduit 158. Meanwhile, passageway 183 connects the sample injection conduit 154 to waste, permitting passage of cleaning solution, if desired, through passageway 183. This procedure provides a reliable injection of a measured volume of sample solution into the conduit leading to the separation column 78 (FIG. 1), the liquid passing through the prefilter 74 and temperature regulating coil 76 before it reaches the separation column.

Features of an improved column cleaning system employing multi-port valves as described hereinabove with respect to FIGS. 1-8 are described in greater detail in commonly owned, copending U.S. patent application Ser. No. 09/285,331 filed Apr. 2, 1999 (now U.S. Pat. No. 6,136,195), the entire contents of which is hereby incorporated by reference.

Figure 7:
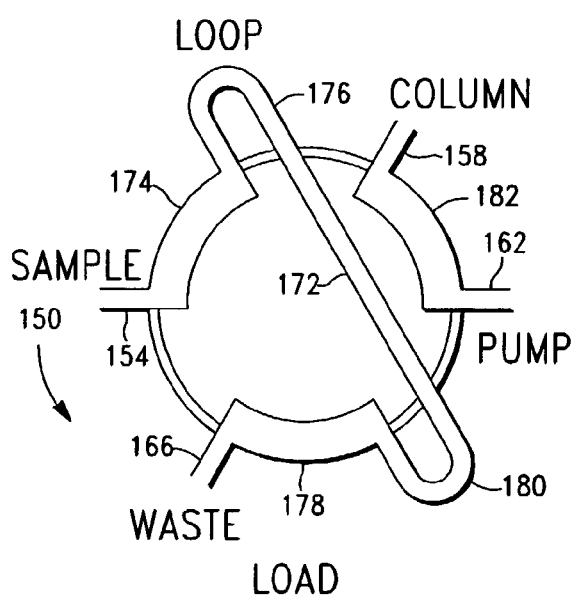
FIG. 7 is a schematic representation of an injection valve in the partial loop load position.
Figure 8:
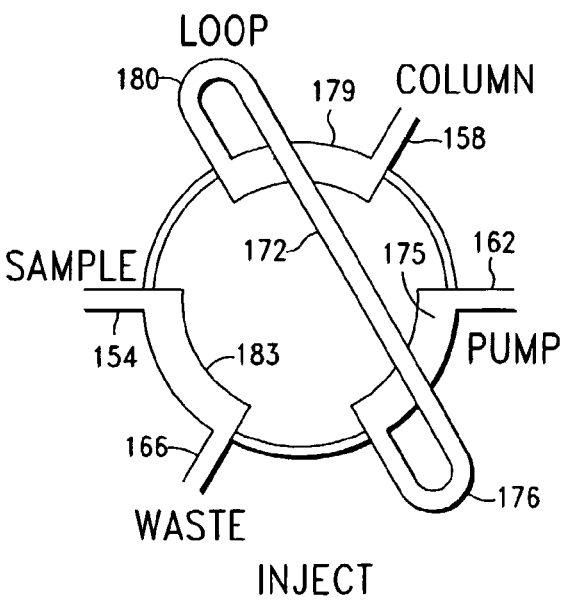
FIG. 8 is a schematic representation of the injection valve in the partial loop injection position.

FIGS. 7 and 8 show the same operational sequence as described with respect to FIGS. 5 and 6 but with a partial loop injection of sample solution or waste liquid.

The system of the invention incorporates oven temperature control means for controlling the temperature of the separation column and the mobile phase entering the column.

Figure 9:
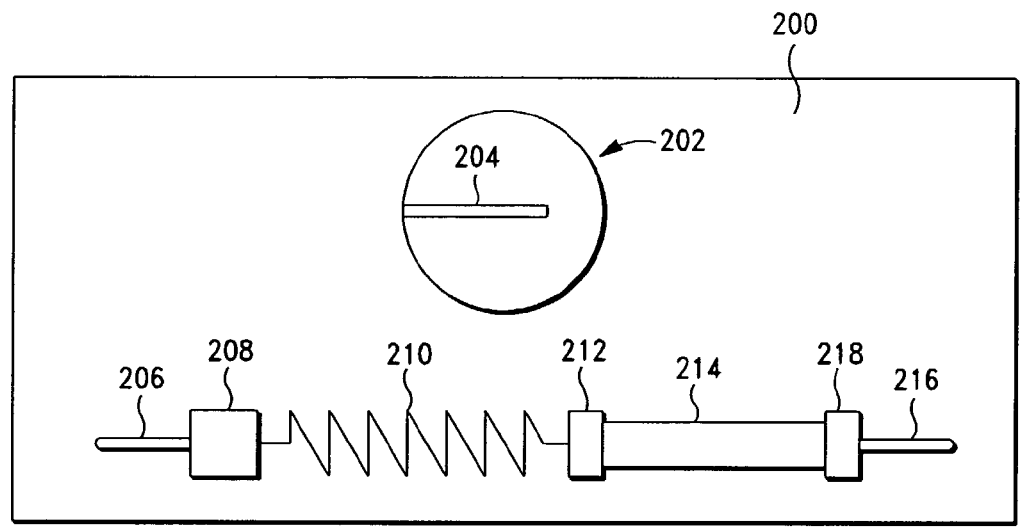
FIG. 9 is a front view of the separation compartment of an improved HPLC DNA analyzer column oven according to this invention.
Figure 10:
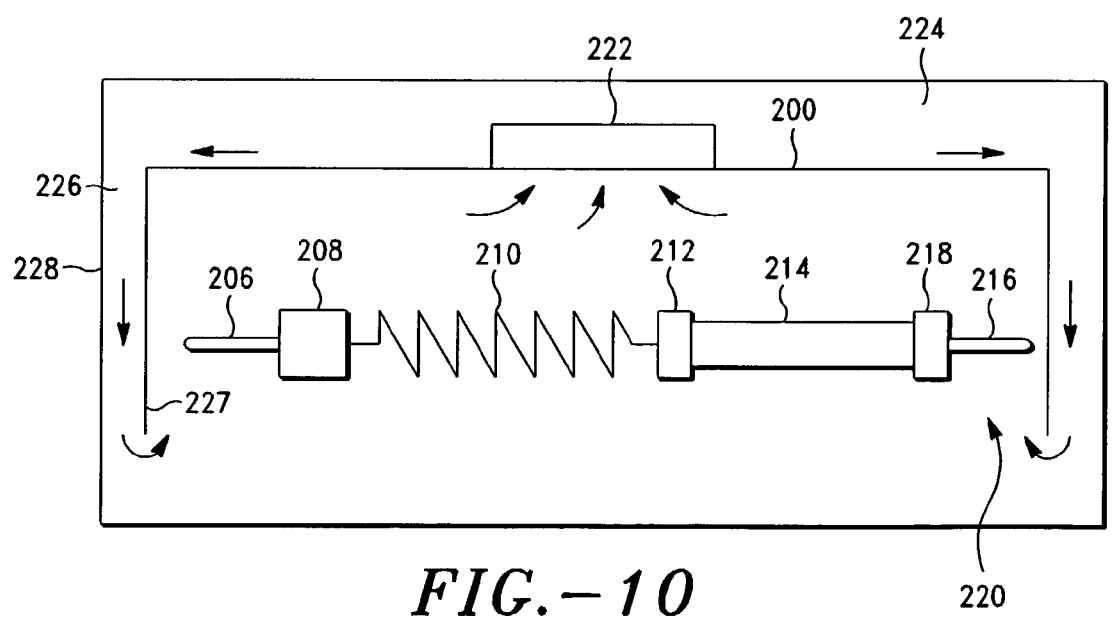
FIG. 10 is a top view of the HPLC DNA analyzer column oven shown in FIG. 9.

FIGS. 9 and 10 illustrate one embodiment of a temperature control means. FIG. 9 is a front view of the process compartment of an HPLC DNA analyzer column oven, and FIG. 10 is a top view of the HPLC DNA analyzer column oven shown in FIG. 9. The process compartment in the embodiment shown in FIGS. 9 and 10 is divided from the heating compartment by backwall 200 in which air exhaust port 202 is positioned. A metal bar 204 enclosing a temperature sensor such as a thermocouple or thermister is positioned in the port 202 to measure the temperature of the air passing through the port. Capillary tubing 206 leads from the sample injector (not shown) to a prefilter 208. Prefilter 208 is an inline filter or guard cartridge, such as described in U.S. Pat. No. 5,772,889, which removes contaminants from the incoming liquid. An elongated coil 210 of capillary tubing has an inlet end in communication with prefilter 208 for receiving mobile phase liquid therefrom. The elongated coil 210 has an outlet end communicating with the inlet end 212 of a separation column 214. Separation column 214 preferably contains MIPC separation media. Outlet tubing 216 leads from the outlet end 218 of the separation column 214 to detector 84 (FIG. 1). Coil 210 is a liquid heating coil made of a DNA compatible, multivalent cation free tubing such as titanium or PEEK. The length and diameter of tubing used is any length which is sufficient to enable liquid mobile phase passing therethrough to reach the equilibrium temperature of air in the processing compartment. A tubing length of from 6 to 400 cm and a tubing ID of from 0.15 to 0.4 mm is usually sufficient. Since the length of tubing 210 does not degrade the separation of components achieved by the system, the length can be selected based on the length required to achieve effective heating of the process liquids.

Referring to FIG. 10, air from the processing compartment 220 passes through the opening 202 in wall 200, through a heater/fan system 222 for temperature adjustment. The adjusted air received by the heating compartment 224 recycles back to the processing compartment 220 along the passageways 226 defined by the spacing between the sidewalls 227 and the outer oven wall 228. The heating coil in the embodiment shown in FIGS. 9 and 10 provides a temperature accuracy to within the range of ±0.2° C. and reduces the temperature equilibrium time between temperature settings to below 5 minutes for temperature changes of 5° C. and below 2 minutes for temperature changes of up to 1° C.

Figure 11:
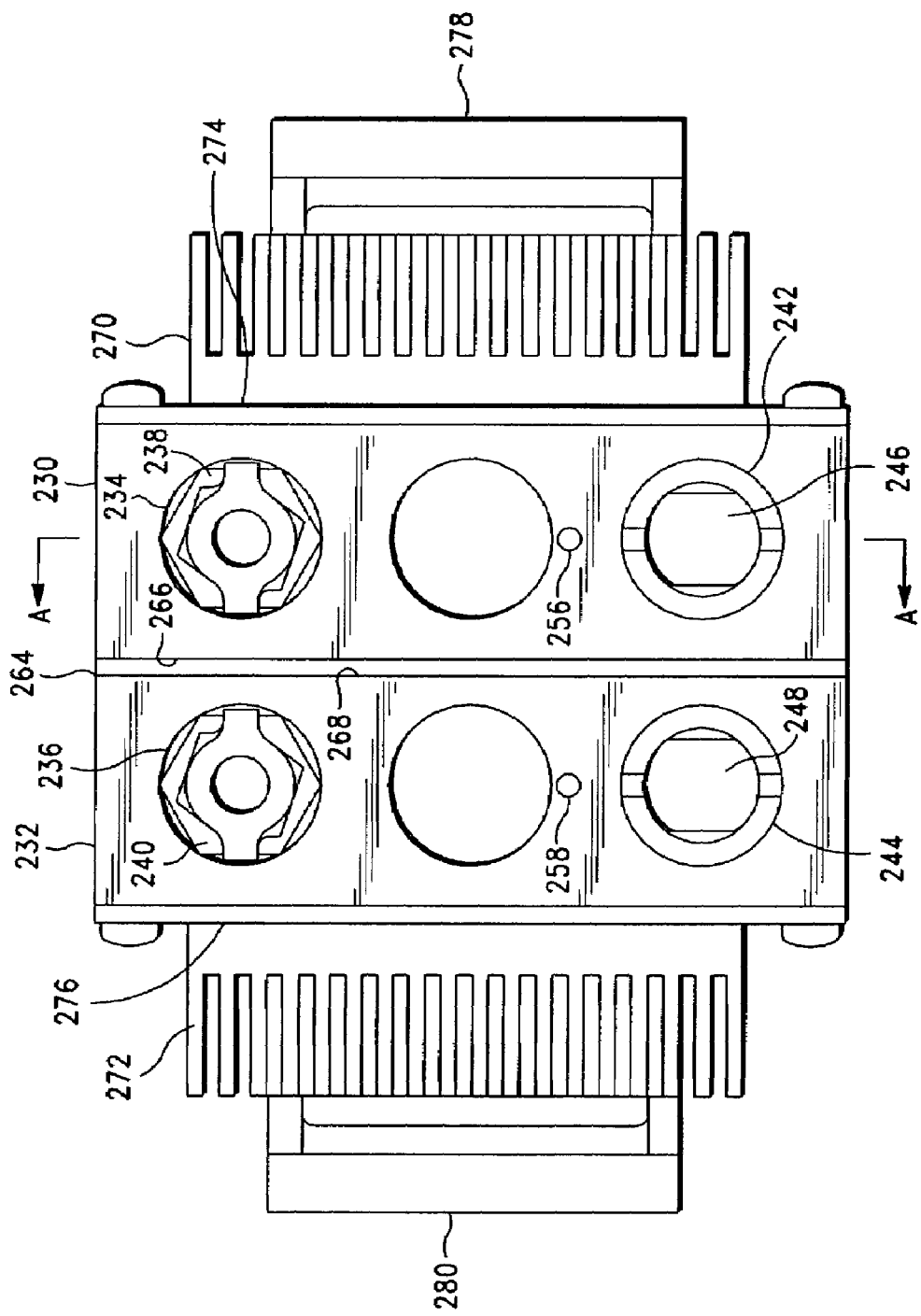
FIG. 11 is an end view of the compact column heater embodiment of this invention.
Figure 12:
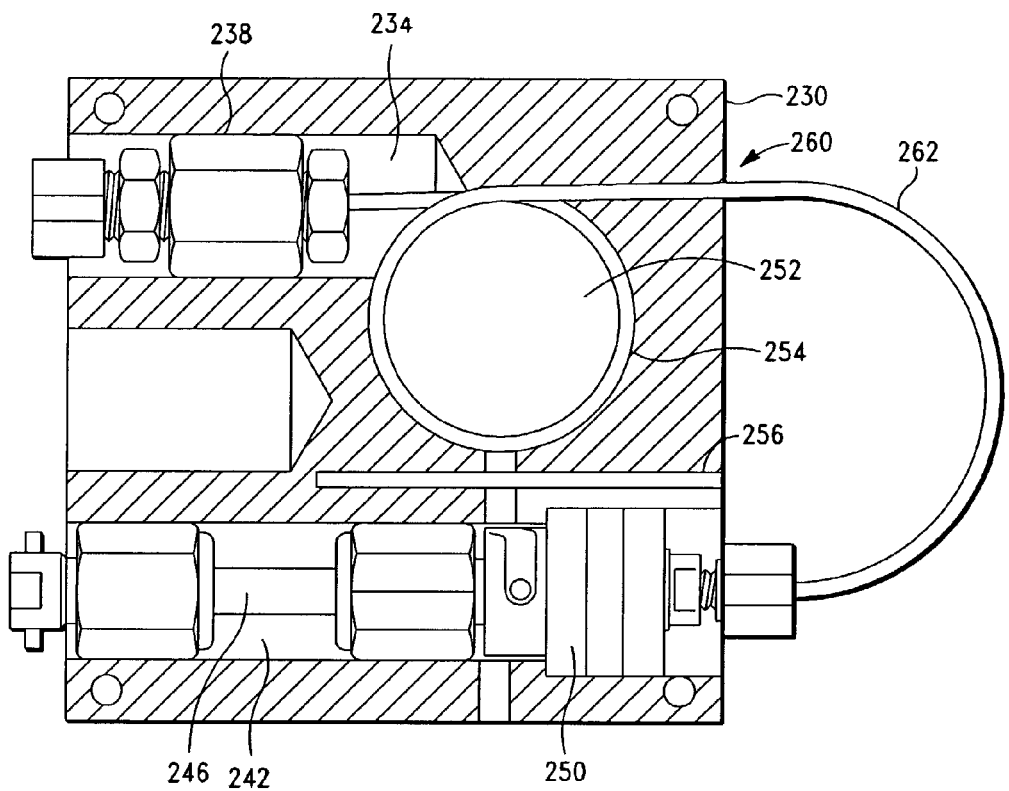
FIG. 12 is a cross-sectional view taken along the line A-A in FIG. 11.

FIGS. 11 and 12 illustrate another embodiment of a temperature control means. FIG. 11 is an end view of a compact column heater, and FIG. 12 is a cross-sectional view taken along the line A-A in FIG. 11. This embodiment relies on direct metal-to-metal conduction of heat to and from the system components and does not depend upon an air bath to achieve temperature changes and accuracy. This embodiment is shown for a two column system, although it could be used for a single column, if desired. It comprises heat conducting blocks (230,232) having receptacles sized and shaped to receive the system components. Filter cavity or prefilter receptacles (234,236) have inner surfaces which are sized to receive prefilters (238,240) and establish heat transfer contact with the outer surfaces thereof. Separation column receptacles (242,244) have inner surfaces sized to receive respective separation columns (246,248) and separation column couplers (250) (one is shown in FIG. 12) which connect capillary tubing to the respective separation columns. Receptacles (242,244) are sized and shaped to establish heat transfer contacts between the inner heat transfer surfaces of blocks (230,232) and the separation column components received therein. Capillary coil receptacles 252 (one is shown in FIG. 12) have an inner surface which is shaped to receive a coils of capillary tubing 254 (one is shown in FIG. 12) and to establish heat transfer contact with the outer surface thereof.

In the embodiment shown in these figures, receptacles (234,236) and (242,244) can be cylindrical holes with approximately parallel central axes lying in a common plane. It would be readily apparent to a person skilled in the art that other configurations are equally suitable and all configurations are considered to be within the scope of this invention.

Temperature sensor receptacles (256,258) are provided in heat conducting blocks (230,232). Capillary receptacle passageways 260 for receiving connecting tubing 262 in a heat-conducting relationship are also provided in the heating-conducting block (230,232). The capillary coil receptacles 252 are shown in this figure to be cylindrical cavities with their axes perpendicular to the axes of receptacles (234,236) and (242,244). Optionally, a conductive metal cylinder (not shown) can be positioned within the capillary coils in heat conducting contact with the inner surfaces thereof to increase heat transfer area between the metal block heating assembly and the liquid in the coils. A KAPTON resistance heater or other type of heating unit 264 is positioned between and in heat-conducting contact with surfaces 266 and 268 of heating blocks (230,232) to transfer heat to the heat-conducting blocks. Heat sinks (270,272) are positioned in heat-conducting relationship with opposed cooling surfaces (274,276) of the heat conduct blocks (230, 232) to remove heat therefrom. Cooling fans 278 and 280 are in a heat removal relationship with the heat sinks 270 and 272 and are activated to accelerate heat removal therefrom.

The heat conducting blocks 230 and 232, and the heat sinks 270 and 272 are made of a material having high heat conductivity such as aluminum or copper, although they can be made of other heat-conducting solids such as ferrous metals or any other solid material having the requisite heat conductivity. Heat pipes can also be used as heat sinks.

The capillary tubing can be made of PEEK or titanium, although titanium is preferred for maximum heat transfer efficiency. With this improved heat transfer, the capillary coil can have a fully extended length as short as 5 cm although a minimum coil length of 10 cm is preferred. A longer coil of PEEK tubing would be required to achieve the same heat transfer as titanium capillary tubing.

The system shown in FIGS. 11 and 12 comprises two systems in mirror image. It will be readily apparent that for a single column, half the system would be sufficient and is intended to be included within the scope of this invention. The position, alignment and spacing of the receptacles are not a critical feature of this invention. Any alignment and configuration which provides a compact and heat-transfer efficient result is intended to be included within the scope of this invention.

The embodiments of the invention shown in FIGS. 11 and 12 provide a compact heater which is more responsive to heater controls, provides rapid changes from one temperature platform to another, and maintains a temperature accuracy within ±0.5° C. of a set temperature. The heat transfer rate obtained with the metal-to-metal contact between the heating block and the elements being heated is far greater than can be obtained in an air bath system, providing the more rapid response to a changed temperature and greater temperature accuracy. It also allows process liquid temperature adjustment with a shorter capillary tubing coil.

Figure 13:
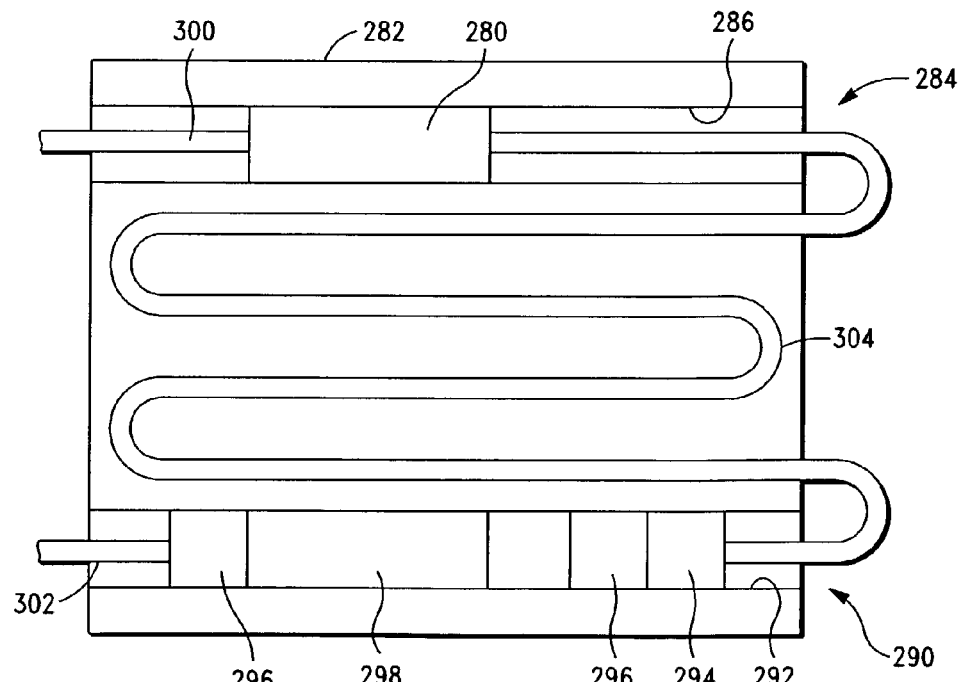
FIG. 13 is a schematic view of a Peltier heater/cooler embodiment of this invention.

In yet another illustration of a temperature control means, FIG. 13 shows a schematic view of a preferred Peltier heater/cooler embodiment of this invention. Heating block 282 is in conductive contact with a Peltier heating element (not shown) for heating or cooling required to reach and maintain a desired temperature. Channel 284 is a prefilter receptor having an inner surface 286 in heat conductive relationship with prefilter 288. Channel 290 is a column and column guard receptor having an inner surface 292 in heat conductive relationship with coupler 294 and end nut elements 296 of separation column 298. Capillary tubing 300 communicates with the prefilter 288 and the sample and solution sources (not shown). Capillary tubing 302 from the outlet of the separation column 288 communicates with an analyzer 84 (FIG. 1). Capillary tubing 304 connects the outlet end of the prefilter 288 with the coupler 294, which in turn communicates with the separation column 298. Capillary tubing 304 is received in a labyrinth-like configuration of channels in the heating block 282 to provide increased capillary length and surface contact between the capillary tubing 304 and the heating block 282.

The configuration of the labyrinth and tubing can be any configuration which provides an adequate capillary length and surface contact, including additional loops and capillary placement of more than one pass per channel. The capillary tubing 304 can be PEEK or titanium, titanium being preferred because of its high heat conductivity. The heating block 282 can be any heat conductive metal. Aluminum or copper are preferred because of their higher heat conductivity, although ferrous metals such as steel can be used. The Peltier heater is controlled with a conventional temperature and control system (not shown) such as the systems used in Peltier thermocyclers. As with the embodiment shown in FIGS. 11 and 12, the temperature accuracy achieved by the Peltier heated block is ±0.5° C.

Features of improved air bath oven and solid block heating systems described hereinabove with respect to FIGS. 9-13 are described in greater detail in commonly owned, copending U.S. patent application Ser. No. 09/295,474 filed Apr. 19, 1999 (now U.S. Pat. No. 6,103,112), the entire contents of which are hereby incorporated by reference.

Figure 14:
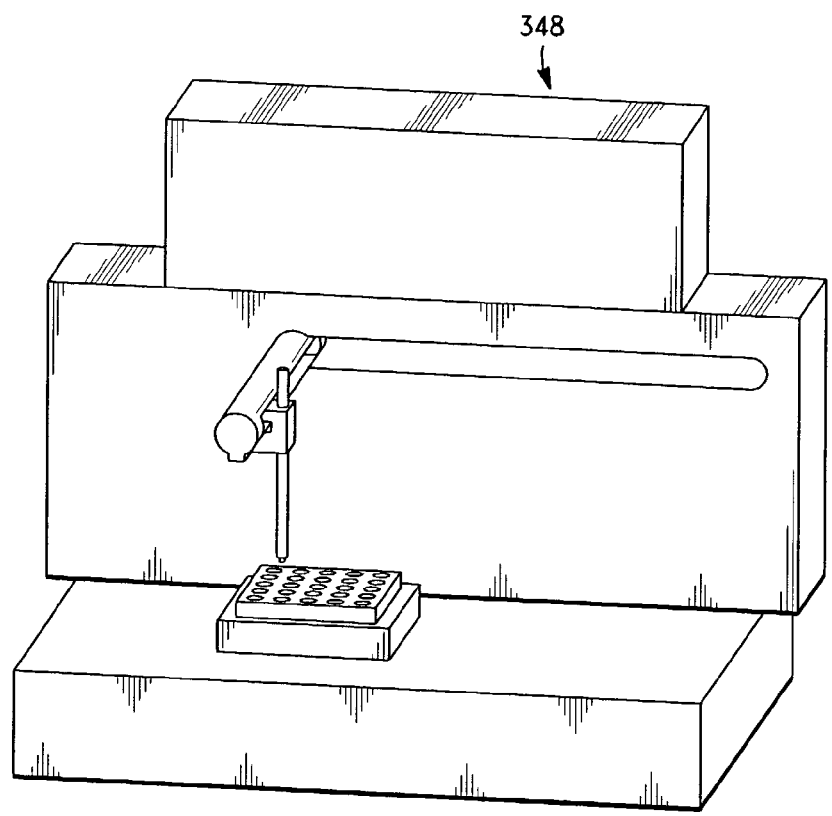
FIG. 14 is a perspective view of a fragment collector.
Figure 15:
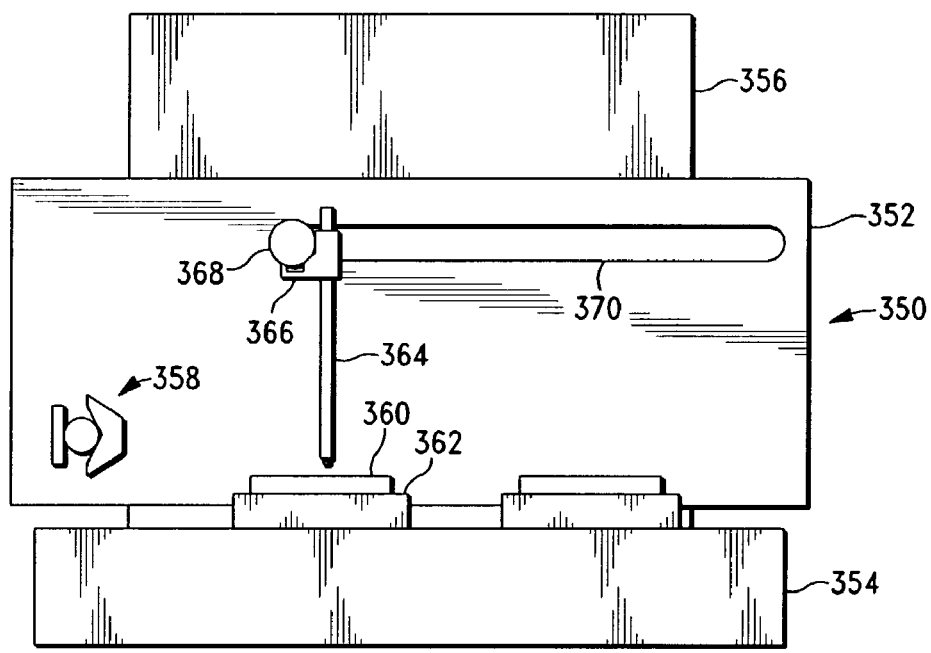
FIG. 15 is a front view of the fragment collector of this invention.
Figure 16:
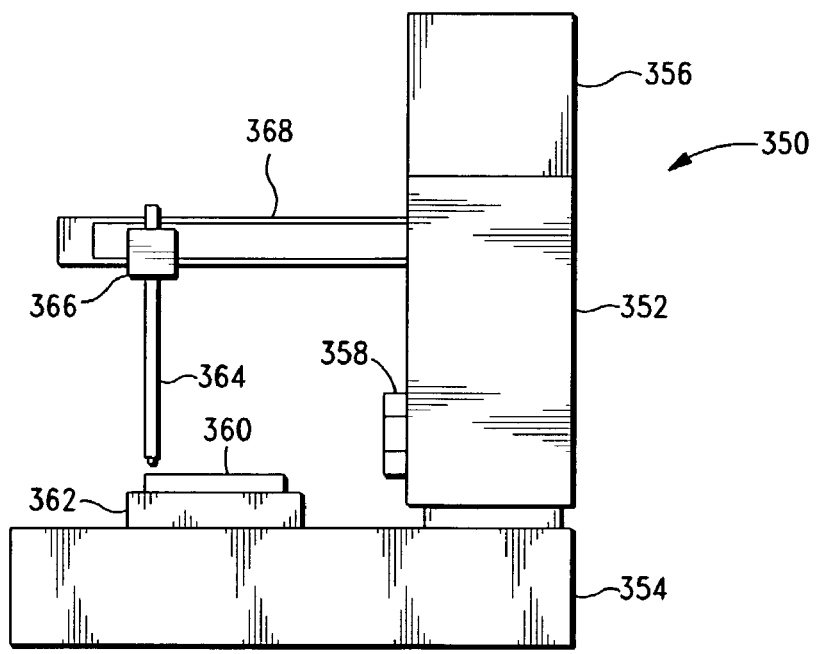
FIG. 16 is an end view of the fragment collector shown in FIG. 15.

FIG. 14 is a perspective view of a preferred fragment collector 348 of this invention, FIG. 15 is a front view thereof, and FIG. 16 is an end view thereof. These illustrate details of the X-axis movement control system. The fragment collector 350 has a controller housing 352, a sample tray support 354 and a puff controller housing 356. A pinch valve 358 is mounted on the front of the controller housing 352 for terminating flow of fluid. The multiwell plates 360 are supported on Peltier cooled chill pads 362. A fragment dispenser 364 is supported on dispenser support carriage 366. The dispenser support carriage 366 is supported for Y-axis movement on the Y-axis movement controller 368. The Y-axis movement controller 368 extends through slot 370 to an X-axis movement control system 372 shown in FIG. 17. The X-axis and Y-axis movement control systems move the dispenser support 366 to a X-Y coordinate corresponding to the central axis of a well in plate 360 into which a fraction is to be dispensed, maintain the dispenser in this position until the fraction is dispensed and them move the dispenser to the X-Y coordinate corresponding to the central axis of the next well into which a fraction is to be dispensed.

Figure 17:
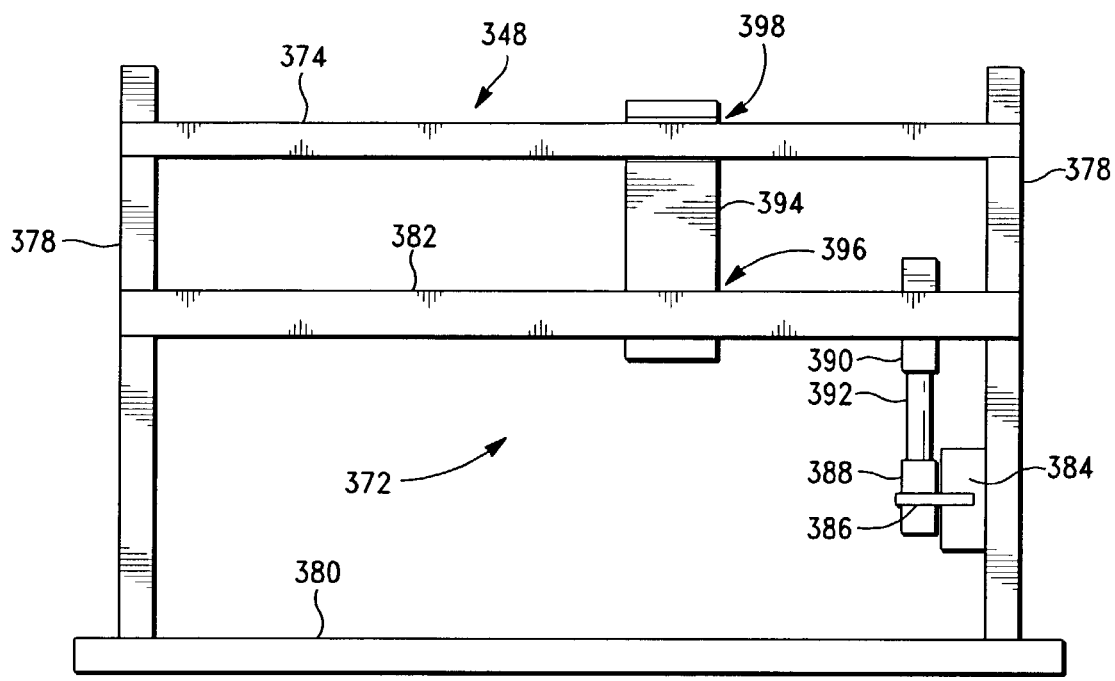
FIG. 17 is a partial front view of the fragment collector of FIG. 15 with a front panel removed to show details of the worm gear drive assembly for X-axis movement of the fragment dispenser.

FIG. 17 is a partial front view of the fragment collector of FIG. 15 with a front panel removed to show details of the worm gear drive assembly for X-axis movement of the fragment dispenser. A guide rod 374 is supported at its ends by the left and right support panels 376 and 378. Support panels 376 and 378 are mounted on horizontal support plate 380. An externally threaded worm gear 382 is mounted for rotation about its central axis on conventional bearings (not shown) supported on the left and right support panels 376 and 378. Stepper motor 384, mounted on the right support panel 378, has an axle 386 upon which a first drive pulley 388 is mounted. A second drive pulley 390 is mounted on the worm gear 382 in a position aligned with the first drive pulley 388. Drive belt 392 engages pulleys 388 and 390 to translate rotary motion of the motor axle 386 to the worm gear 382.

The Y-axis movement controller 368 is supported on the X-axis movement carriage 394 (FIG. 17). The X-axis movement carriage 394 has an internally threaded bore 396 which engages the external threads of the worm gear 382. A channel 398 in the X-axis movement carriage 394 is positioned for sliding engagement with the guide rod 374 for sliding movement in the X-axis direction. The guide rod 374 stabilizes the X-axis movement carriage against rotation about the axis of the worm gear 382 when the worm gear turns. Stepped activation of the stepper motor 384 is translated to a stepped rotation of the worm gear 382, moving the X-axis movement carriage to the left or right along the X-axis to a position which places the dispenser in alignment with the X-axis coordinate of a well into which a fraction is to be dispensed.

Figures 18, 19:
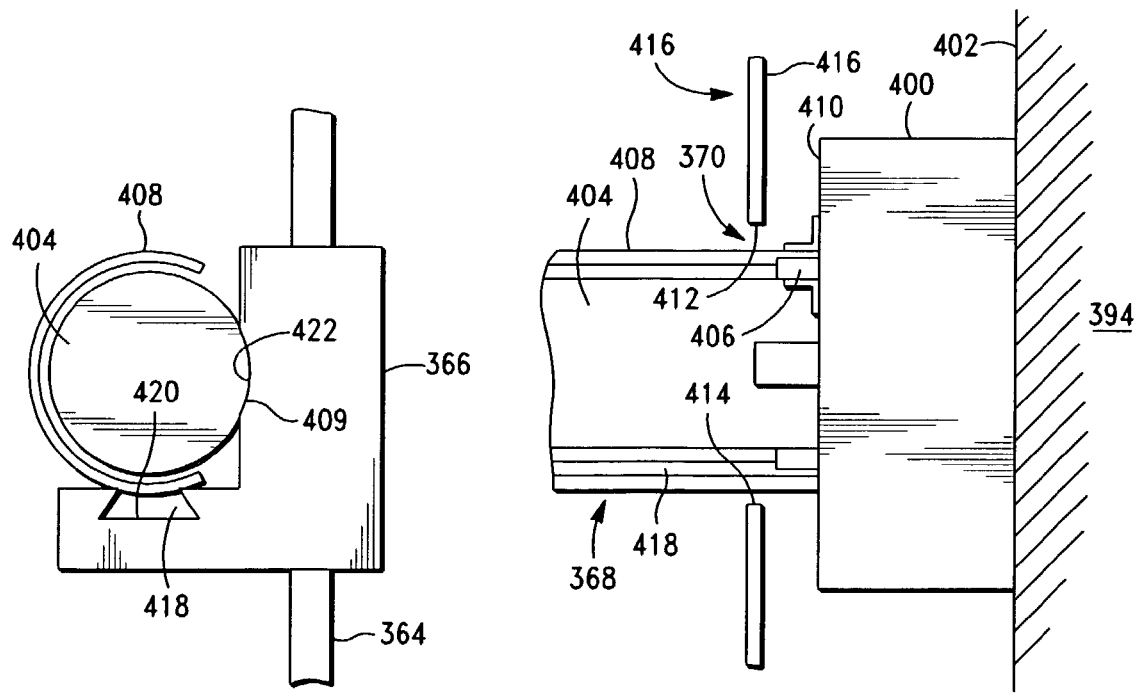
FIG. 18 is a fragmentary view of the motor and worm gear assembly of the drive assembly for Y-axis movement of the fragment dispenser.
FIG. 19 is an end view of the drive assembly for Y-axis movement of the fragment dispenser.

FIG. 18 is a fragmentary view of the motor and worm gear assembly of the drive assembly for Y-axis movement of the fragment dispenser. A Y-axis stepper motor 400 is supported on a support surface 402 of the X-axis movement carriage 394. A Y-axis worm gear 404 is mounted on the stepper motor drive 406. The Y-axis worm gear 404 is partially enclosed in an outer sheath 408. The outer sheath 408 can be mounted on the surface 410 of the housing of the stepper motor 400 or alternatively, it can be attached to the carriage 394. The slot 370 is defined by opposed edges 412 and 414 of the front panel 416. A guide 418 is mounted on the undersurface of the sheath 408 in an axially parallel alignment with the sheath 408 and the worm gear 404.

FIG. 19 is an end view of the drive assembly shown in FIGS. 17 and 18. This shows further details of the drive assembly for Y-axis movement of the fragment dispenser. The sheath 408 has a lateral opening which exposes the threaded engaging surfaces 409 of the worm gear 404. The dispenser support 416 is supported by mutual engagement of the guide 418 and a matched dispenser support groove 420. The inwardly sloped edges of the guide 418 engage the correspondingly outwardly sloped opposed edges of the support groove 420. The dispenser support 366 has a grooved surface 422 which engages the engaging surfaces 409 of the worm gear 404. Rotation of the worm gear 404 effects a Y-axis movement of the dispenser support 366. The groove 420 engagement with the guide 418 stabilizes the dispenser support 366 against rotary movement about the axis of the worm gear 404 when it rotates. Stepped activation of the stepper motor 400 is translated to a stepped rotation of the work gear 404, moving the dispenser support 366 to the backward or forward along the Y-axis to a position which places the dispenser in alignment with the Y-axis coordinate of a well into which a fraction is to be dispensed.

It will be readily apparent to a person skilled in the art that the matched engaging surfaces of the guide 418 and the groove 420 can be other arrangements which provide the guide and stabilizing function of the guide and groove engagement. Examples of suitable fragment collectors include the Model ASW100 available from Transgenomic and the Model FC 203/204 Fraction Collectors from Gilson (Middleton, Wis.).

Figure 20:
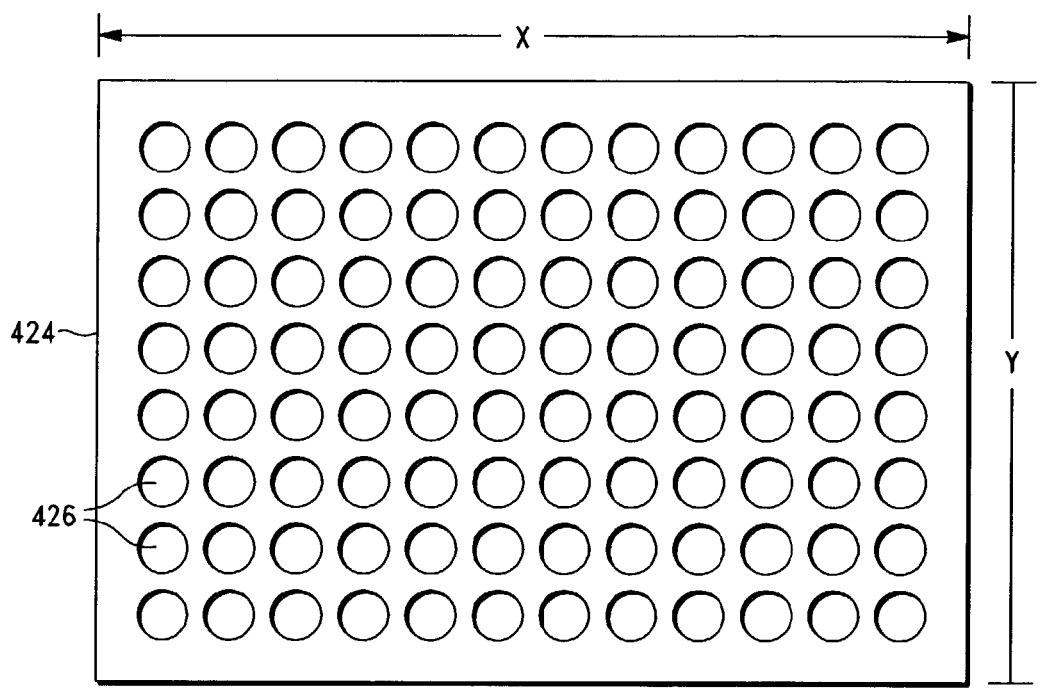
FIG. 20 is a top view of a standard 96 well multiwell plate.

FIG. 20 is a top view of a standard 96 well multiwell plate. The plate 424 has sample wells 426, the center axis of each well having exact repeated spacings along the X and Y axes from the central axes of next adjacent wells. The number of wells and the well spacings can be selected to have any value desired. The shape, size and distribution of wells can be standardized for 96, 384, and 1536 well microtiter plates, for example, and each or all of these can be used in conjunction with the fragment collector of the instant invention. The wells can be used as shown or they can be protected from sample contamination by use of individual sample vial liners or a conventional overlay plate liner containing sample vials which have outer dimensions corresponding to the inner dimensions of the microtiter plate wells.

Figure 21:
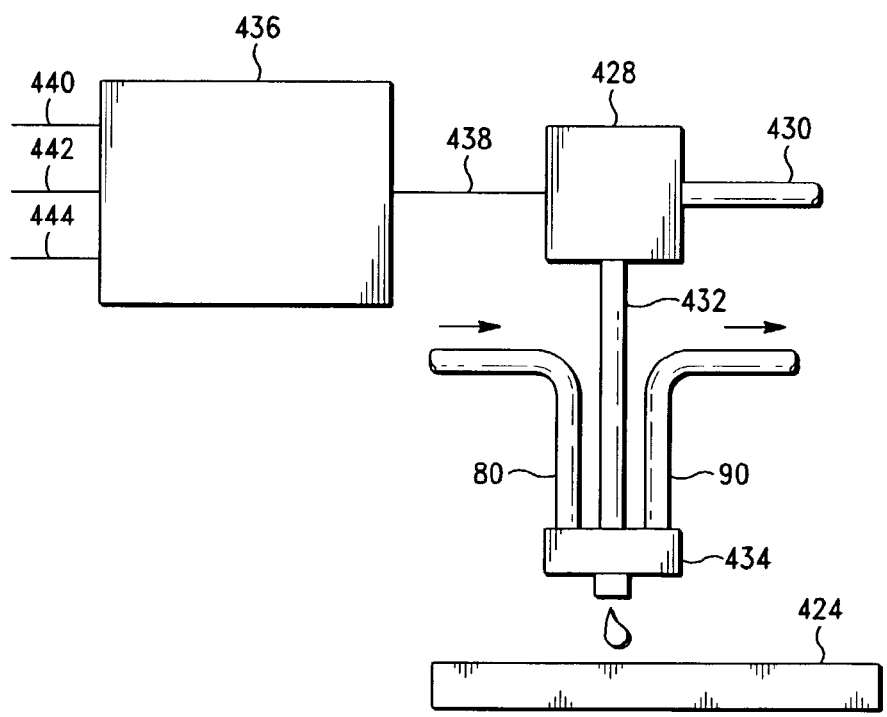
FIG. 21 is a schematic view of an air-puff dispenser embodiment of this invention.

FIG. 21 is a schematic view of an air-puff dispenser embodiment of this invention. Features of the dispenser are described in copending, commonly assigned U.S. patent application Ser. No. 09/143,456 filed Aug. 28, 1998 (now U.S. Pat. No. 6,074,880), the entire contents of which are hereby incorporated by reference. Pressurized gas is fed to the puff valve 428 through conduit 430 from a source of pressurized gas (not shown). Conduit 432 communicates with the puff valve 428 and with the sample dispenser 434. Conduit 80 communicates with the separation system shown in FIG. 1 and with the dispenser 434. The puff valve 428 is connected with the fragment collector controller 436 by communication line 438 for receiving operating valve open and valve close signals from the controller. The valve open signal is given to the puff valve 428 when a sample is to be dispensed into a well or vial in the multiwell plate 424, and the valve closed signal is given to the puff valve 428 when the sample collection is completed or when the vial is full, whichever is earlier. The collection controller 436 provides the valve open and valve closed signals in response to data and instructions received through communication lines 440, 442 and 444, for example.

Figure 22:
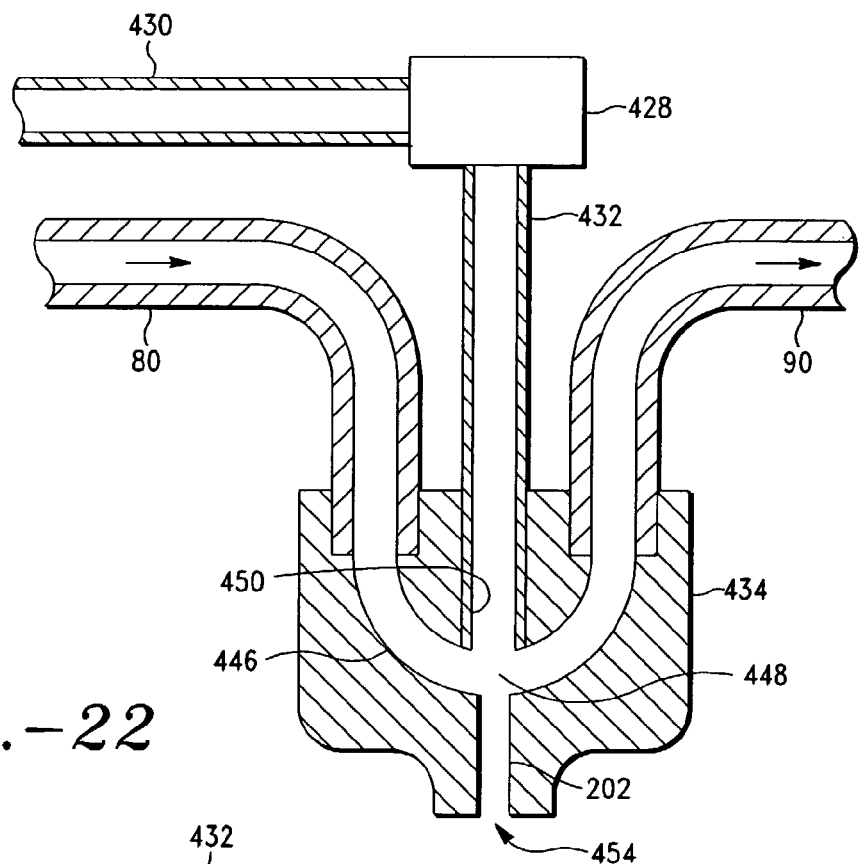
FIG. 22 is an enlarged cross-sectional view of the air-puff dispenser embodiment of FIG. 21.

FIG. 22 is an enlarged cross-sectional view of the air-puff dispenser embodiment of FIG. 21 showing the elements thereof when the puff valve 428 is in a closed position. The sample supply conduit 80 communicates with the inlet end of a curved passageway 446 of the dispenser 434. Conduit 90 to waste communicates with the outlet end of the curved passageway 446. The center 448 of the curved passageway 446 communicates with the air puff conduit 432 through an opening in the passageway. The air puff conduit 432 is received in a cylindrical recess 450 of the dispenser 434, positioned to place its outlet in communication with the curved passageway 446. The central portion of the curved passageway 446 has a further opening communicating with a dispensing passageway 452. When the puff valve 428 is closed, sample fluid passes through the conduit 80, central passageway 446 and to the waste conduit 90. The dispensing passageway has a capillary size, so fluid in this passageway is stationary when the puff valve 428 is closed.

Figure 23:
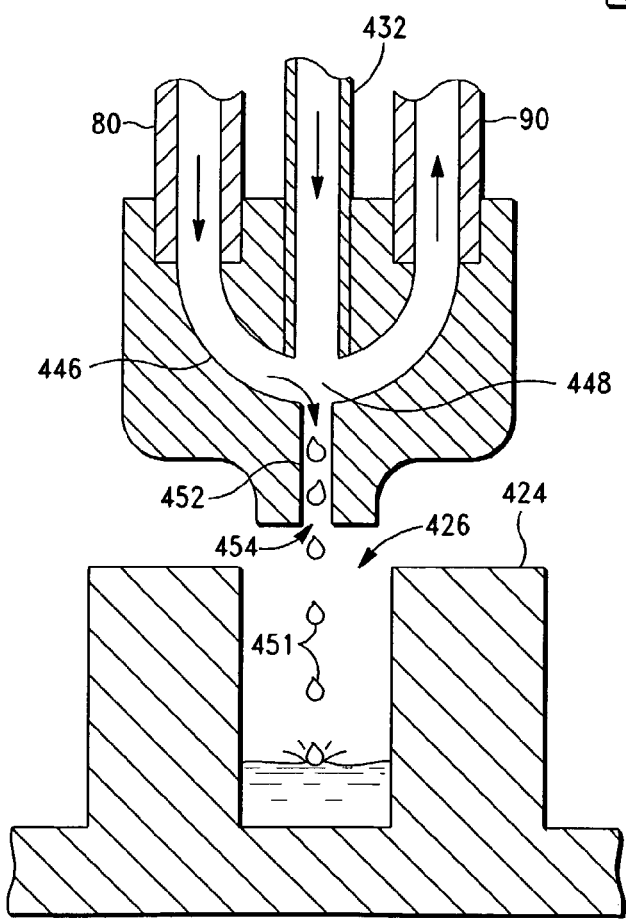
FIG. 23 is an enlarged cross-sectional fragmentary view of the dispenser tip and well of a multiwell plate show in FIG. 22.

FIG. 23 is an enlarged cross-sectional fragmentary view of the dispenser tip shown in FIG. 22 when the puff valve 428 is opened to expel a droplet of sample into a well of the multiwell plate. In this view, the sample continues to flow through inlet conduit 80. When the puff valve 428 is opened, a puff of air passes through the conduit 432 into the central portion 448 of the curved chamber 446, increasing the pressure in the chamber 448, and expelling a drop 451 of liquid from the tip 454 of the passageway 452 into well 426. The puff valve 428 can be opened and closed to create a quick succession of bursts, expelling a series of drops into the well 426 until either the sample collection is complete or the well 426 is filled.

Figure 24:
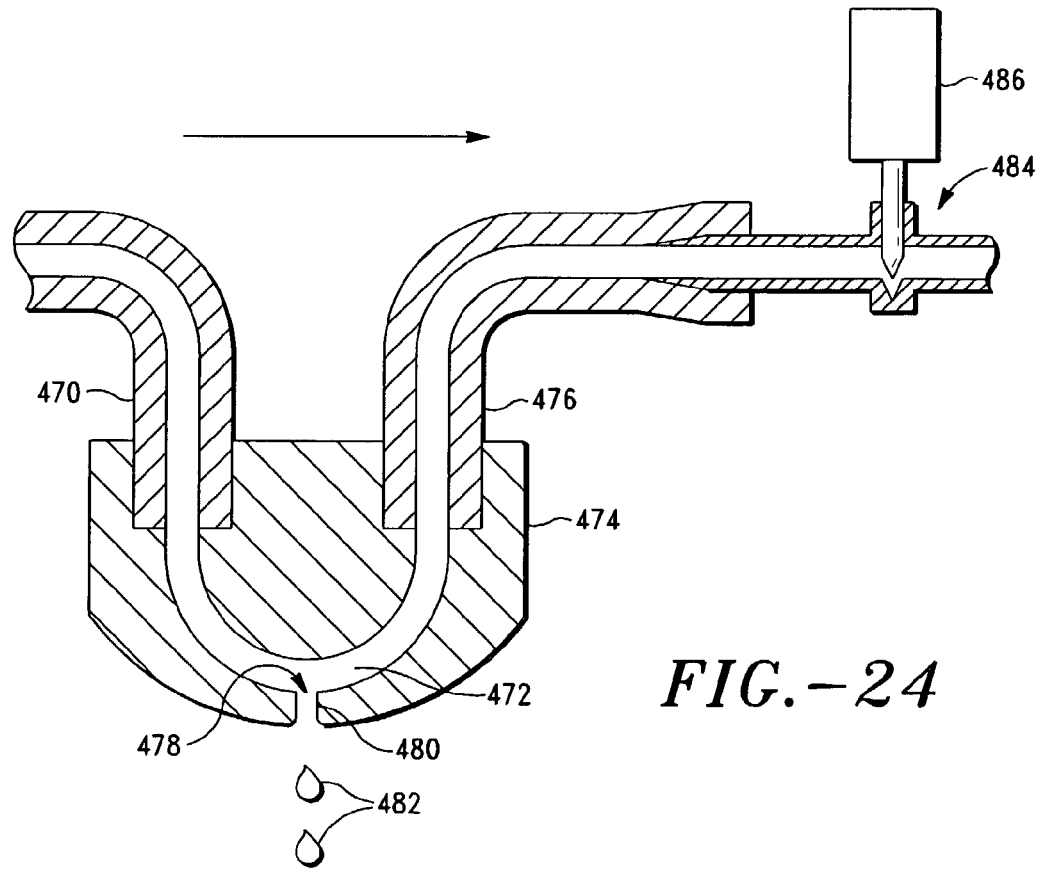
FIG. 24 is a cross-sectional view of an alternate embodiment of a dispenser tip according to this invention with a flow restriction in the outlet line.
Figure 25:
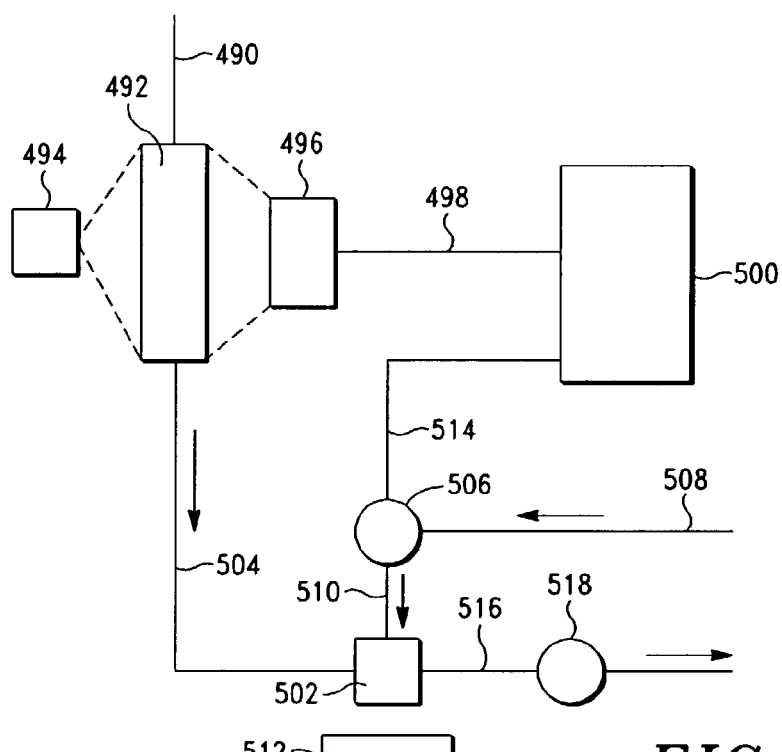
FIG. 25 is a schematic view of the combination of the detector, central controller and air puff drop size control system.

FIG. 24 is a cross-sectional view of an alternate embodiment of a dispenser tip according to this invention with a flow restriction in the outlet line. The mobile phase inlet conduit 470 through which the mobile phase containing the sample fractions leads to an ejection chamber 472 in the ejector tip 474. The ejection chamber 472 communicates with an outlet waste conduit 476 and a droplet ejection port 478 with a capillary-size droplet forming opening 480. Droplets 482 falling from the opening 480 are collected in a sample vial (not shown). A flow restriction 484 having a restriction actuator 486 is positioned in the outlet conduit 476. The restriction actuator can be a conventional solenoid. A signal voltage to the restriction actuator 486 and restriction 484 can be constructed to provide the desired degree of restriction in flow through the conduit 476. It will be readily apparent to a person skilled in the art that the flow restriction can be achieved by any adjustable flow-through valve including pinch valves, gate valves and the like, and the invention is intended to cover the use of all adjustable restriction valves which provide the desired degree of restriction FIG. 25 is a schematic view of the combination of a conventional detector, a central controller and a drop size control system of this invention. The mobile phase stream containing the polynucleotide fractions passes through conduit 490 to the detection cell 492. A light source 494 directs light through the cell 492. Light emitted from the cell is collected and measured by the detector 496, producing an outlet voltage which is a function of the transmission at the selected wavelength. UV light having a wavelength of 268 nm is conventionally used for polynucleotide level measurements. If the polynucleotides have a fluorescent moiety bound thereto, the detector can be a fluorescent detector which measures the emissions at a wavelength which matches the principal emission wavelength of the fluorescent moiety.

The output voltage signal from the detector 496 is fed by line 498 to the central controller unit 500 where the signal is amplified and analyzed. The mobile phase stream exiting the measurement cell 492 is directed to the drop former 502 by the conduit 504. In this embodiment, the drop former 502 can be an air puff system shown in greater detail in FIGS. 21, 22, and 23, for example. The ejection chamber of the drop former 502 is supplied with air puffs from the puff valve 506 which received compressed gas through conduit 508. The air puffs are fed to the ejection chamber through air puff conduit 510 communicating with the puff valve 506 and the ejection chamber 502 to form fraction droplets which are collected in sample containers in plate 512. The puff valve 506 opens in response to an open valve signal from the controller 500 through line 514. The mobile phase remaining after drop formation is fed to waste through conduit 516, which includes a restriction valve 518.

Figure 26:
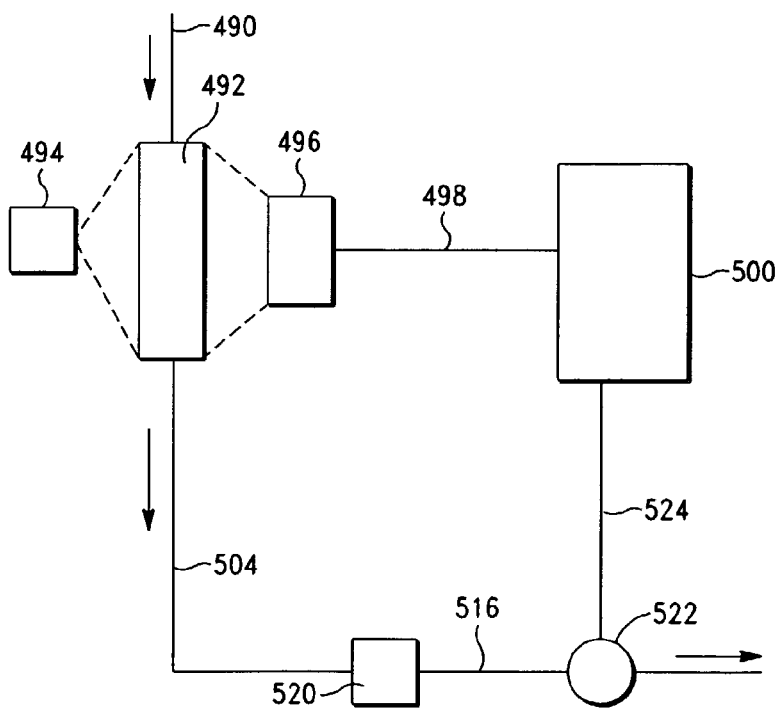
FIG. 26 is a schematic view of the combination of the detector, central controller and flow restriction control system.

FIG. 26 is a schematic view of the combination of the detector, central controller and flow restriction control system. The schematic representation in FIG. 26 has many of the same elements as the schematic representation in FIG. 25, and where the same numbers are used in both views for the same elements. The drop former 520 can be the same as described in FIG. 24. The restriction means 522 includes a restriction activator which responds to an activate restriction command through line 524 from the central controller 500, thereby increasing the pressure in the ejection chamber. Referring to FIG. 24, the increased pressure required is sufficient to overcome the interfacial tension of the liquid in the ejection chamber 472 and cause liquid to flow through the capillary-size opening 480.

Figure 27:
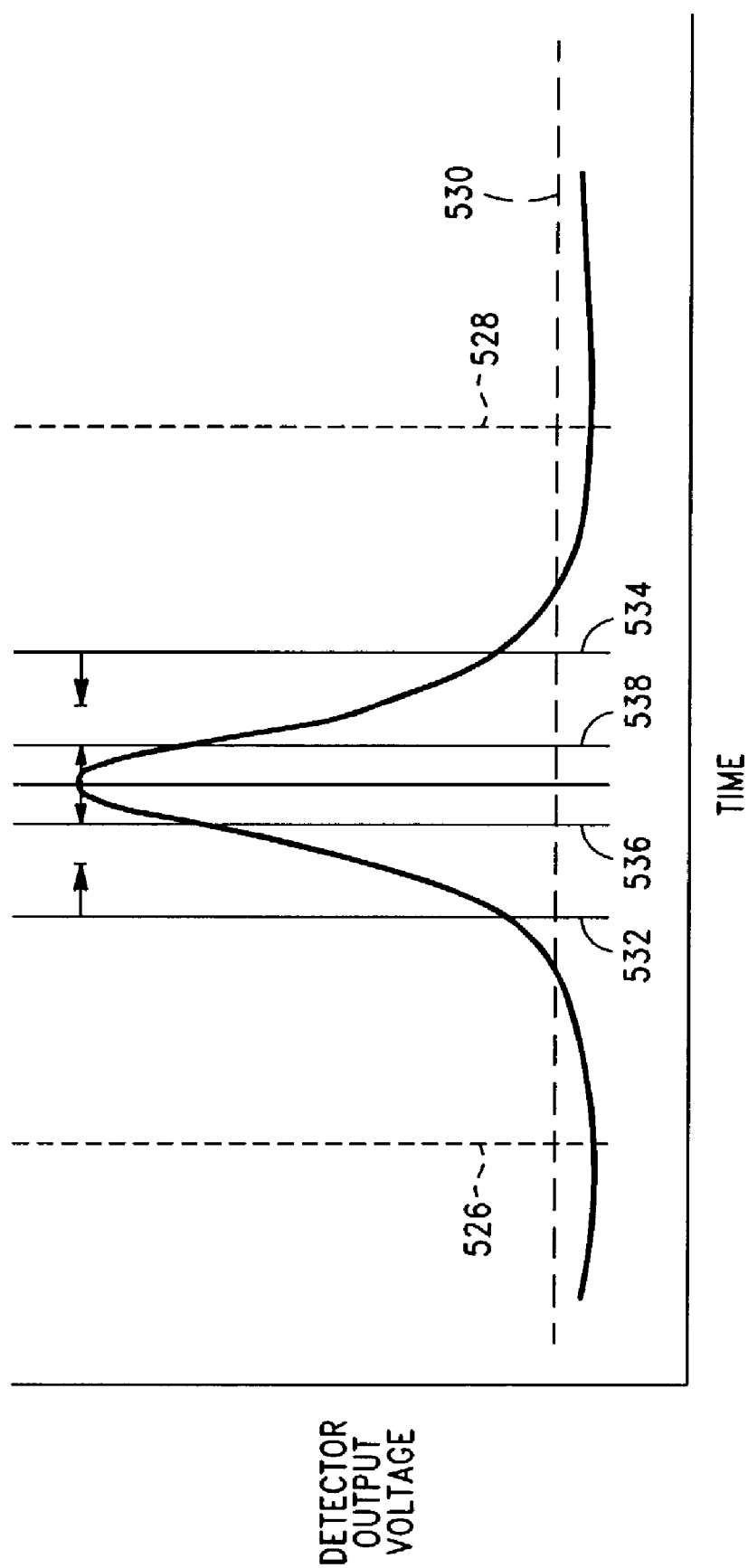
FIG. 27 is a representation of a chromatogram illustrating criteria for fraction collection based on time interval, threshold and slope.

FIG. 27 is a representation of a chromatogram illustrating criteria for fraction collection based on time interval, threshold and slope. A fraction is collected by opening the puff valve 428 shown in FIG. 21 or closing a flow restriction 484 as shown in FIG. 24 or both if both are provided in a system. The open puff valve or close restriction commands can be sent to the respective collection activators during a time window with or without confirmation of the presence of a peak indicating the presence of a fraction. In other words, the collection can be made blind at a selected time window (shown by the vertical lines 526 and 528) which is known to contain a target polynucleotide, if the polynucleotide is present. This is particularly useful if the sample contains only a trace quantity of a desired base-pair length fraction of a polynucleotide. This method collects the widest fraction range, and the product may include portions of another fractions. Blind Collection is described in commonly assigned U.S. patent application Ser. No. 09/311,116 filed May 13, 1999 (now U.S. Pat. No. 6,218,153) (incorporated by reference herein in its entirety).

Alternatively, the open puff valve or close restriction commands can be sent to the respective collection activators during an interval when the detector signal is above an absolute threshold value shown by the broken line 530. This method collects a narrower fraction range, eliminating other fractions if the peak is distinct. However, if the peak is not clearly defined, other fractions may be included in the sample collected.

In a third alternative, the open puff valve or close restriction commands can be sent to the respective collection activators during an interval when the slope of the leading edge is above a certain selected value and when negative of the trailing edge is above a selected value. The slope values can be selected to collect most of the fraction by selecting lower slope values (shown by the vertical lines 532 and 534). Alternatively, the slope values can be selected to be a higher value (shown by the vertical lines 536 and 538) in order to collect only the central, purest portion of the fraction.

It will be appreciated that each system component as shown in FIGS. 1 and 2 preferably includes a conventional computer instruction input means which acts as a communication interface between the physical device and the software which controls the device. For example, preferred injection valves as described hereinabove include an RS-232 port and provisions for TTL and contact closure control.

In a preferred embodiment, all of the system components share a standard communication interface. As an example, the Model L-7100 pump (Hitachi) includes D-Line network communications for interaction and integration with other system components. Preferred system components also incorporate integrated circuitry for processing signals sent and received from the central controller 500.

Figure 28:
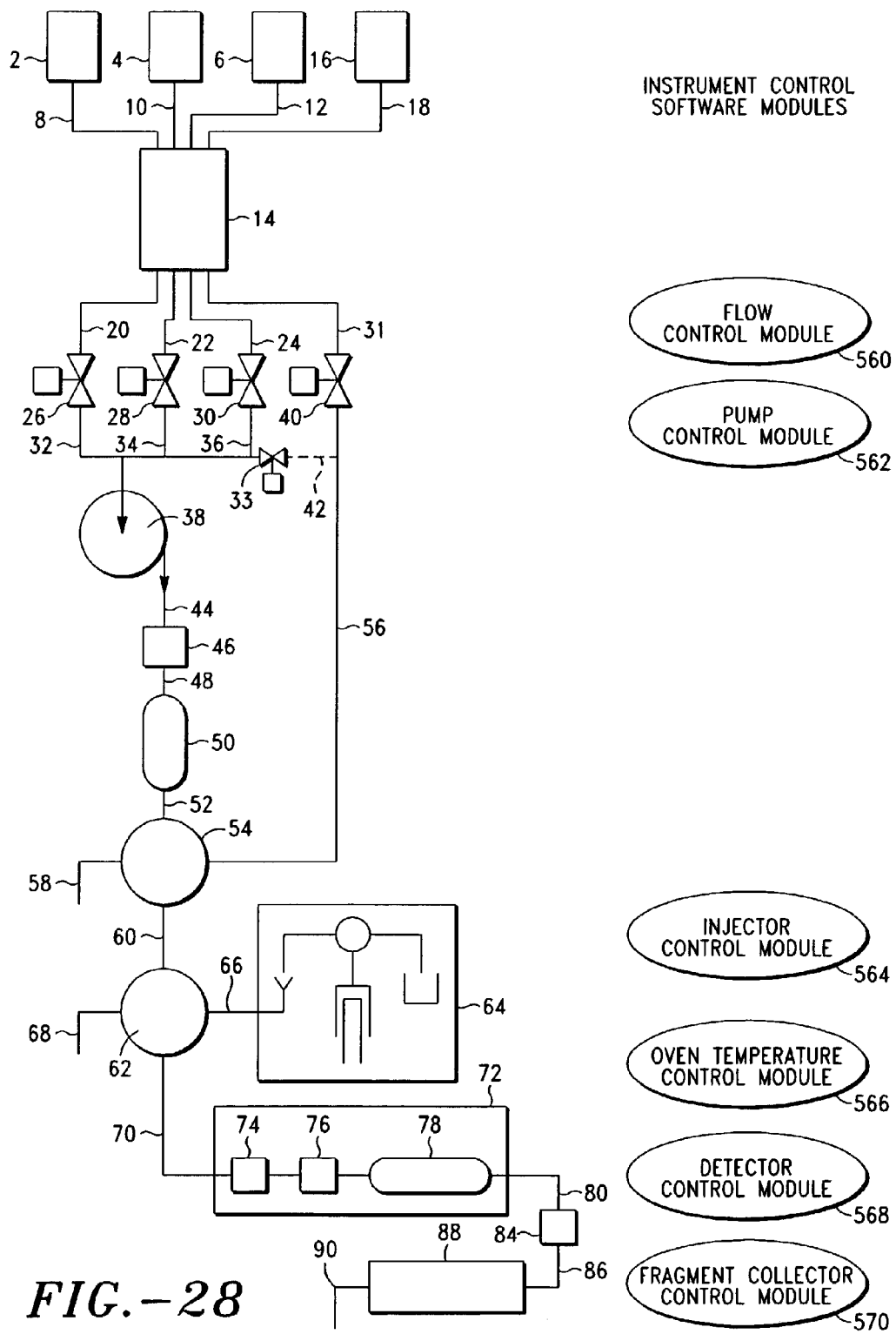
FIG. 28 is a schematic representation of the MIPC system of FIG. 1 together with the control modules associated with each component thereof.

FIG. 28 is a schematic representation of the MIPC system of FIG. 1 together with the control software modules associated with each component thereof. Components of an Instrument Control Software are shown on the right side of FIG. 28. The Instrument Control Software consists of several modules each responsible for controlling a specific component or group of components of the chromatography system.

One of these modules, the Mobile Phase Flow Control Module 560, controls the aqueous component proportioning valve 26, solvent solution proportioning valve 28, the auxiliary liquid proportioning valve 30 and the cleaning solution valve 40. Module 560 controls the action of valves 26 and 28 (and possibly 30) to provide specific solvent concentration gradients during the separation process by changing valve settings on one or more of the valves 26, 28, and 30 throughout the separation process. The settings of the proportioning valves 26, 28, 30, and 40 can be changed by operation of corresponding stepper motors (not shown) or the like. In order to change the concentration of the solvent, the Module 560 sends instructions to the stepper motors of the valves 26, 28, and 30, and the valves 26, 28, and 30 close or open by the prescribed number of increments. The Module 560 preferably instructs the valves to close and/or open simultaneously to provide constant flow rate through the pump 38.

Also, Module 560 can provide column cleaning between separations by instructing a stepper motor, associated with the cleaning solution valve 40, to open the valve 40 and thereby flush the injection valve 54, capillary tubing 76, in-line system components, and the separation column 78 with cleaning solution from cleaning solution container 16. Valve 33 is preferably closed during the cleaning process.

Alternatively, if the system includes flow control pumps 92, 94, 96 (FIG. 2), the Mobile Phase Flow Control Module 560 translates volume flow instructions received from the central controller 500 into pump settings delivering the desired volumes. Instructions sent to Module 560 to establish a specified gradient can include flow instructions corresponding to the desired ratio of solutions A and B, for example.

An optional cleaning solvent cleanup phase with the system shown in FIG. 2 is effected by sending timed instructions to the Mobile Phase Control Software Module 560 to open pump 110 and pass cleaning solution through the injection valve 54, the capillary tubing 76, in-line system components, and the separation column 78. Preferably, valve 111 is closed during the cleaning process.

Pump Control Module 562 controls operational parameters of the pump 38, such as an on/off status of the pump 38 and a flow rate or liquid pressure level. The Pump Control Module 562 monitors the flow rate through pump 38 during the separation process and adjusts the pump to maintain the flow rate at the prescribed level.

Injector Control Module 564 controls the operation of the sample aliquot selector 64 and the injector valve 62 to effect the injection of a selected sample into the stream of solution flowing to the separation column 78. The Injector Control Module 564 can respond to a variety of instructional codes. These codes include useful injector module functions with which the injector system 64 and the injector valve 62 can be controlled. Examples include commands for aspirating a sample, dispensing, tube identification, needle height, needle moving speed, valve position settings, timer settings, and other commands.

Oven Temperature Control Module 566 controls the operation of the air bath oven 72. The oven temperature is determined by the heat control system such as shown in FIGS. 9-13. The Oven Temperature Control Module activates the air bath oven 72 and continuously controls the temperature level in the oven 72 through the whole run time of a separation process. The Oven Temperature Control Module 566 sends instructions to the heating means controller with the desired process temperature. The heating means controller, in turn, sends a command to the heating/cooling means which actuate the desired temperature change. The Oven Temperature Control Module 566 receives feedback data from a calibrated temperature sensor such as the sensor 204 (FIG. 9). It provides information about the air temperature in the air bath oven 72. If the absolute difference between the desired process temperature and the air temperature is above the allowed margin, the Oven Temperature Control Module 566 instructs the heating means controller to adjust the settings of the heating/cooling means in accordance with the difference between the desired process temperature and the temperature sensor 204 reading.

Optionally, the Oven Temperature Control Module 566 receives temperature reading off the temperature sensor positioned directly on the coil tubing 76, for more accurate reading of the process temperature, and adjusts the settings for heating/cooling means accordingly.

Other software modules include a Detector Control and Data Collection Module 568 which control operation of the detector 84; a Fragment Collector Module 570 which controls the fragment collector system. A Sample Analysis Module which presents the user with a list of available Sample Tables, listing available preset Methods that can be used to analyze the specified sample. Alternatively, the user can define his own method by inputting required information at the Sample Analysis Module 550 prompt. Such information will include temperature conditions, gradient conditions, injection mode, etc.

Figure 29:
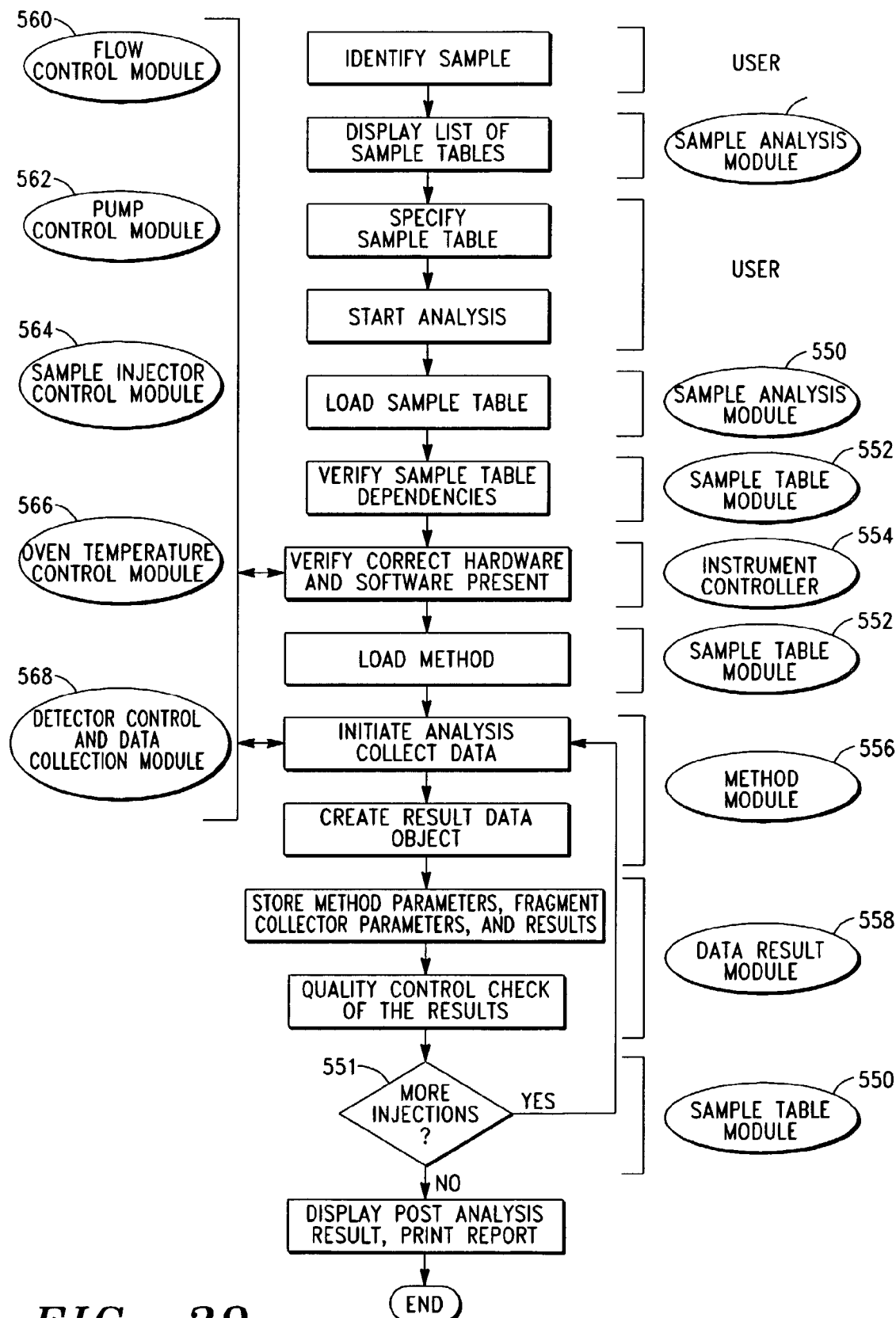
FIG. 29 is a schematic representation of an embodiment of the MIPC system computerized control process and the modules associated with each portion of the process.

FIG. 29 is a schematic representation of an embodiment of the MIPC system computerized control process and the modules associated with each portion of the process.

First, a sample to be analyzed is identified by a user. A Sample Analysis Module 550 receives the sample identity in the form of the number of a vial containing the sample to be analyzed, or X-Y coordinates of such vial.

A list of Sample Tables is displayed by the Sample Analysis Module 550, listing available preset Methods that can be used to analyze the specified sample.

The Sample Table, which includes a method to be effected, is then specified by the user. Alternatively, the user can define his own method by inputting required information at the Sample Analysis Module's 550 prompt. Such information can include temperature conditions, gradient conditions, injection mode, etc.

If fragment collection is desired, the user also specifies fragment collection parameters. The user can select one of the predefined methods of fragment collection or specify his own. In the case of Blind Collection, the user specifies time intervals for the collection. In the case of Threshold Collection, the user specifies the threshold at which the collection starts. In the case of Slope Collection the user specifies the angle of the intensity curve at which the collection starts. Based on this information a Fragment Collection Table is created, containing instructions to The Fragment Collector Control Module 570.

The analysis process is initiated by the user. Loading of a Sample Table is then performed by The Sample Analysis Module 550. The Sample Table includes a selected method for each sample. The Sample Table dependencies are verified by a Sample Table Module 552.

A hardware and software check is initiated by The Sample Table Module 552. The Sample Table Module 552 instructs the Instrument Controller 554 to check if all hardware and software required by specified method is available and operational. Flow Control Module 560 verifies that the solvent proportioning valve 26, carrier liquid proportioning valve 28, auxiliary liquid proportioning valve 30, and cleaning solution valve 40 are present and operating properly. Pump Control Module 562 checks if the pump 38 is present and operating properly. Injector Control Module 564 verifies that the sample aliquot selector 64 and the injector valve 62 are present and operating properly. Oven Temperature Control Module 566 verifies that the air-bath oven 72, pre-filter 74, and column 78 are present and operating properly. If fragment collection is a part of the chosen method, the Fragment Collector Module 570 verifies if the fragment collector 88 is present in the system and operates properly.

If the Instrument Controller 554 finds an error, i.e. equipment or software required for this particular method is not available in the present system configuration, the Sample Table Module aborts analysis and reports an error to the user.

Otherwise, the specified Method is loaded on the system. The Sample Table Module 552 initiates calculation of the specific parameters for the selected method into a Method Table. Such parameters include number or coordinates of the vial containing the sample to be analyzed, volume of the sample to be analyzed, method of injection of the sample, speed of injection, solvent flow rate, injection solvent concentration, solvent concentration gradient details, temperature of the air bath oven, allowed discrepancy between the desired process temperature and the actual process temperature, reading frequency of the analyzer, etc. The mobile phase gradient details can be in a form of a table specifying times when the % B should be changed and the magnitude of the change. Alternatively the table can contain specific times at which the % B is to be changed and absolute % B to be established at these times. Alternatively the table can contain a frequency of mobile phase concentration updates and a formula for calculating the desired % B based on the time. In this case, instructions to Flow Control Module 560 are calculated in real time during a separation process.

Then the analysis is initiated by the Method Module 556. The Method Module 556 instructs the Instrument Controller 554 to start the run. The Instrument Controller in turn effects the following pre-analysis procedures by the Instrument Control Software Modules:

The Oven Temperature Control Module 566 instructs the temperature control means to bring the oven temperature to the level prescribed by the selected method by sending instructions to the heating/cooling means controller. These instructions contain desired process temperature. The Oven Temperature Control Module 566 verifies that the air-bath oven 72 reached the desired temperature by comparing the data from the temperature sensor 204 with the desired process temperature. If the difference between the prescribed and the actual temperatures is more than an allowed margin of error provided in the Method Table, the Oven Temperature Control Module instructs the heating/cooling means controller to raise or lower the oven temperature accordingly. This process is repeated until the actual oven temperature is within the desired parameters.

The Flow Control Module 560 sets the valves 26, 28, and 30 by operation of corresponding stepper motors to achieve the injection solvent concentration as set in the Method Table. This solvent concentration is reached by balancing flow rates of solvent, carrier liquid and auxiliary liquid. The initial solvent concentration preferably effects binding of the DNA fragments in the sample to the non-polar separation media.

Pump Control Module 562 sets the pump 38 to the desired pumping speed to facilitate the flow rate prescribed in the Method Table. Then the Method Module 556 instructs the Instrument Controller 554 to begin analysis. The Instrument Controller 554 in turn effects the following actions by the Instrument Control Software Modules:

The Injector Control Module 564 facilitates an injection of the sample by the sample aliquot selector 64 from a selected well such as at 114 as specified in the Method Table. The sample is injected in the manner specified by the Method Table. The DNA fragments in the injected sample bind to the non-polar separation media. In the case of gradient separation, at prescribed time intervals, the Flow Control Module 560 changes the setting of the valves 26, 28, 30 to increase the solvent concentration to the level prescribed by the Method Module table. The ratio of the solutions A and B is continuously changed to maintain the solvent ratio in the desired gradient. For isocratic flow, the ratio of solutions A and B is maintained at a constant value.

In separating a mixture of DNA fragments by base-pair size, several different mobile phase gradients may be used. An increasing mobile phase gradient is a step-wise or continuous increase of the concentration of solution B, and one or more portions of the gradient may be flat or a phase of constant % B (isocratic solvent flow). DNA fragments are deposited on the non-polar surfaces of the separation media in the separation column 78 with a mobile phase stream containing low % B. DNA fragments are separated from the column in a relatively narrow range of % B.

Figure 30:
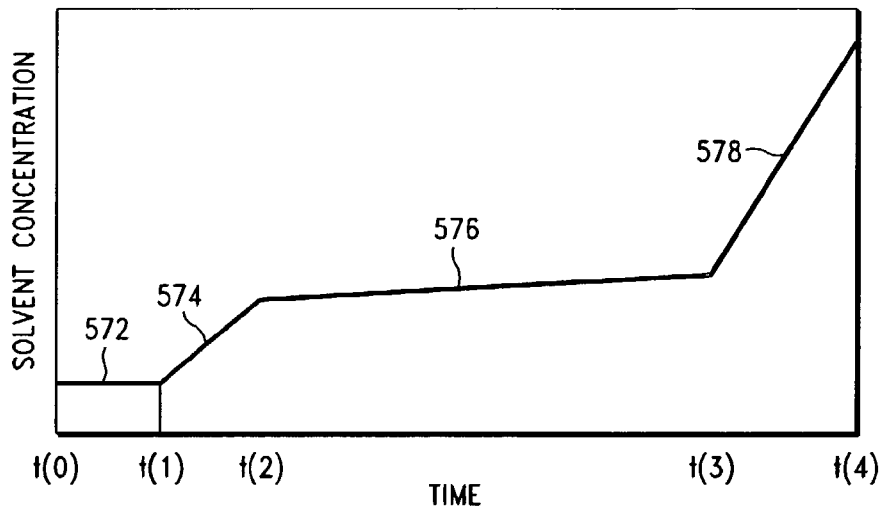
FIG. 30 is a graphical representation of the solvent concentrations during a basic separation of nucleic acid fragments in the MIPC process.

FIG. 30 is a graphical representation of the solvent concentrations in the mobile phase during a basic separation of nucleic acid fragments in the MIPC process. Referring to FIG. 30, a flat solvent concentration 572 which binds DNA fragments to the separation media in column 78 is from t(0) to t(1). This can be followed by a steep solvent gradient elevation 574 to the beginning of the separation phase at t(2). At this point the solvent gradient is changed to a DNA separation gradient 576 which begins at t(2) and continues to a solvent concentration level at which all DNA fragments of interest have been released from the column at t(3). The driving solvent gradient then changes to a steeper gradient 578 which continues to a level at t(4) which removes all remaining nucleic acids from the separation column 78 and prepares the column for the next separation procedure.

During these phases, the settings of valves 26 and 28 are continuously adjusted to effect the desired mobile phase composition in the liquid which is passed through the separation column 78. Since the valve adjustments are incremental, they can also be viewed as microstep adjustments, and the gradients can be viewed as microstep gradients.

The Flow Control Module 560 includes the translation formulas for converting specific volumes and volume ratios to the corresponding valve control settings. Instructions to the Flow Control Module 560 to establish a specified gradient include ratio parameters for solutions A and B.

Throughout the analysis, the Oven Temperature Control Module 566 monitors the oven temperature and adjusts the oven temperature control means settings if the oven temperature deviates from the prescribed level for more than the allowed margin of error.

When the analysis begins, a Detector Control and Data Collection Module 568 is activated by the Instrument Controller 554 and in turn activates the detector 84. The Instrument Controller 554 provides the Module 568 with specific instructions on the detector 84 operation mode. Such instructions can include, in the case of UV detector, a base level of UV transmission to be detected, a range of transmission level to be detected, and the frequency of readings to be obtained by the detector. The analyzer starts analyzing the passing liquid and passes the collected data to Module 568. For each reading by the detector 84 the Module 568 records a level of transmission detected and a time of the reading. Module 568 decodes and collects the obtained information and also passes this data in analog format to the Sample Analysis Module 550 for real-time display.

If fragment collection is a part of the chosen method, a Fragment Collector Module 570 is activated by the Instrument Controller 554. The Fragment Collector Module 570 gives commands to the fragment collector 88 in accordance with the Fragment Collector Parameter Table. The information collected by the Module 568 can also be passed to the fragment collector 88 and used for threshold or slope collection of the mobile phase.

The Fragment Collector Module 570 receives instructions on a time frame for the collection from the Instrument Controller 554. In case of Blind Collection, the instructions will be in the form of specific times to begin and to end collection for a specific fraction or a start time and a length of collection interval. A confirmation of the presence of the actual peak from the analyzer 84 is not required.

For Threshold Collection, the Fragment Collector Module 570 receives the level of intensity generated by the analyzer 84 at which collection should start. When the level of intensity falls below this threshold or the vial specified for the collection of this fragment is full, the Fragment Collector Module 570 gives the fragment collector a command to terminate collection.

For Slope Collection, the Fragment Collector Module 570 receives a Slope Threshold, i.e., the level of speed of growth of the intensity generated by the UV detector 326 at which the collection should begin. When the slope of the curve exceeds a specified threshold, the controller 330 gives the fragment collector 88 an instruction to start collection. The collection can be interrupted at any point if the vial specified for the collection of the fragment is full. Otherwise the collection proceeds until the slope turns negative, i.e. passes the peak value of the intensity. The collection is interrupted when the absolute value of the slope of the curve falls below the specified level.

These methods of fragment collection can also be used in combination. For instance, the Blind Collection may only take place when confirmation of the fragment present is received by threshold or slope method.

The Sample Analysis Module 550 displays the progress of the analysis as the results are being acquired by the Detector Control and Data Collection Module 568. Once the analysis is completed, a Result Data Module 558 is created and the method parameters are stored there. The Result Data Module 558 receives information collected by the Detection Control and Data Collection Module 568 and analyzes the results. Then the Result Data Module 558 stores the results of the run. The Sample Table Module 552 initiates quality control check and post analysis of the run by the Result Data Module 558. Then the Sample Analysis Module 550 displays post processing results of the run and the Sample Table Module 552 prints a report.

Figure 31:
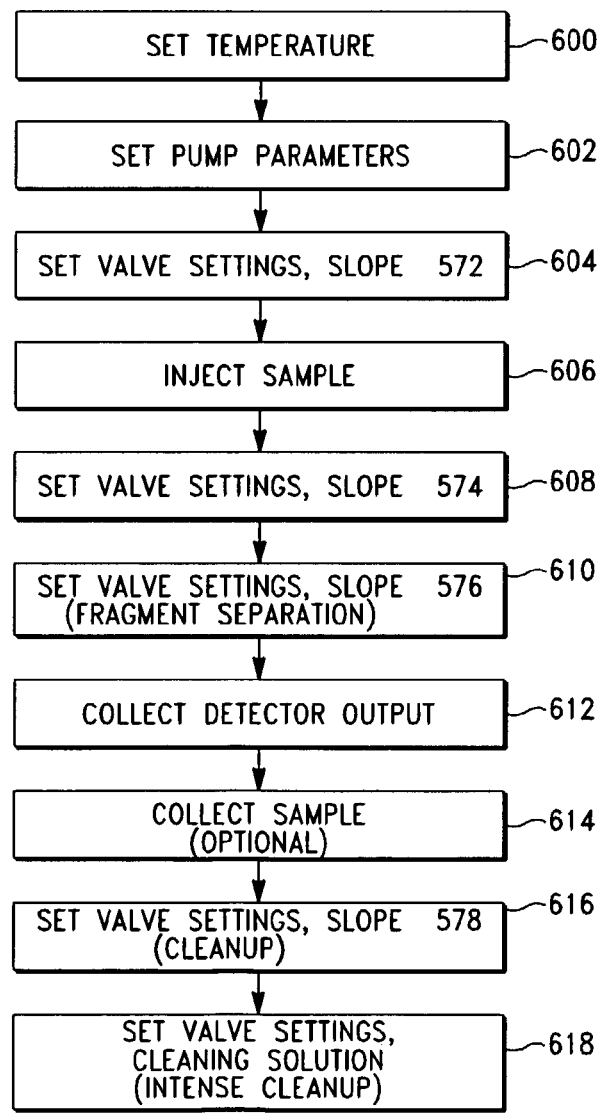
FIG. 31 is a flow diagram illustrating an embodiment of the separation method of the invention.

FIG. 31 illustrates the steps in a separation process as carried out using the system of the invention.

In step 600, the air-bath oven 72 is heated to the process temperature prescribed by the Method Table. Heating procedure is controlled by the Oven Temperature Control Module.

In step 602, the pump parameters are set in accordance with the parameters in the Method Table, and the pump 38 is turned on. The flow rate of the mobile phase through the pump, is attained. The process of establishing the prescribed mobile phase flow rate through the pump is controlled by the Pump Control Module 562.

The valves 26, 28, and 30 are set to achieve the initial mobile phase composition as prescribed by the Method Table. This stage, indicated at 604, is shown on FIG. 30 as slope 572 between t(0) and t(1). The process of establishing initial solvent concentration is controlled by the Flow Control Module 560.

After the settings of valves 26, 28, and 30, the rate of the pump 38, and the temperature of the air-bath oven 72 are established, the injector 64 injects the sample into the flow of solvent, as indicated at step 606. The process of sample injection is controlled by Injector Control Module 564. After the sample is injected into the system and DNA fragments of the sample attach themselves to the separation media of the column 78, the settings of the valves 26, 28, 30 are changed to effect a rapid solvent gradient. This stage 608 of the process is shown on FIG. 30 as slope 574 between t(1) and t(2). This rapid gradient washes out the shorter DNA fragments separation of which is not desired.

After the shorter DNA fragments are eluted from the column, the gradient slope is changed to a slower rate. This stage of the process is indicated at 610 and is shown on FIG. 30 as slope 576 between t(2) and t(3). During this period between t(2) and t(3) the separation process takes place, i.e. the DNA fragments are eluted from the system depending on their base-pair length proportional to the solvent concentration. The solvent gradient and associated operations of the valves 26, 28, and 30 are controlled by the Flow Control Module 560.

While the separation process takes place, detector 84 constantly detects the presence of eluted DNA fragments in the outflow of the separation column 78 and records the amounts of DNA material present at any particular moment of time. The operation of the detector 84 is controlled by the Detector Control Module 568. The detector output is collected as indicated at step 612, converted to a digital format, and stored on a data storage device.

If fragment collection is desired, the fragment collector 88 collects separated material from the outflow of the detector 84 as shown in optional step 614. The methods of fragment collection, such as Blind Collection, Threshold Collection, and Slope Collection are described hereinabove (see FIG. 27). The operation of the fragment collector 88 is controlled by the Fragment Collector Control Module 570.

After the separation process is concluded and all DNA fragments of interest are eluted from the column, the solvent concentration is increased again. The concentration of the organic solvent is rapidly increased to reach the concentration high enough to elute all remaining DNA fragments from the separation column 78. This stage 618 of the process is shown as slope 578 between t(3) and t(4). The mobile phase solvent gradient and associated operations of the valves 26, 28, and 30 are controlled by the Flow Control Module 560.

From time to time, intense cleanup is required to adequately maintain the condition of the system and particularly the separation media. In these instances the last part of the separation process will be flushing the system with the cleaning solution from cleaning solution container 16 by opening cleaning solution valve 40, preferably with simultaneous closure of valve 33, and pumping the solution through the system to remove any residue.

Multiple injections of the same sample can be performed by the system of the invention. For example, the volume per injection and the number of injections can be specified for a particular vial, as indicated in a row of a Sample Table. Additional injections can be made based on the status of decision branch 551 (FIG. 29).

Figure 32:
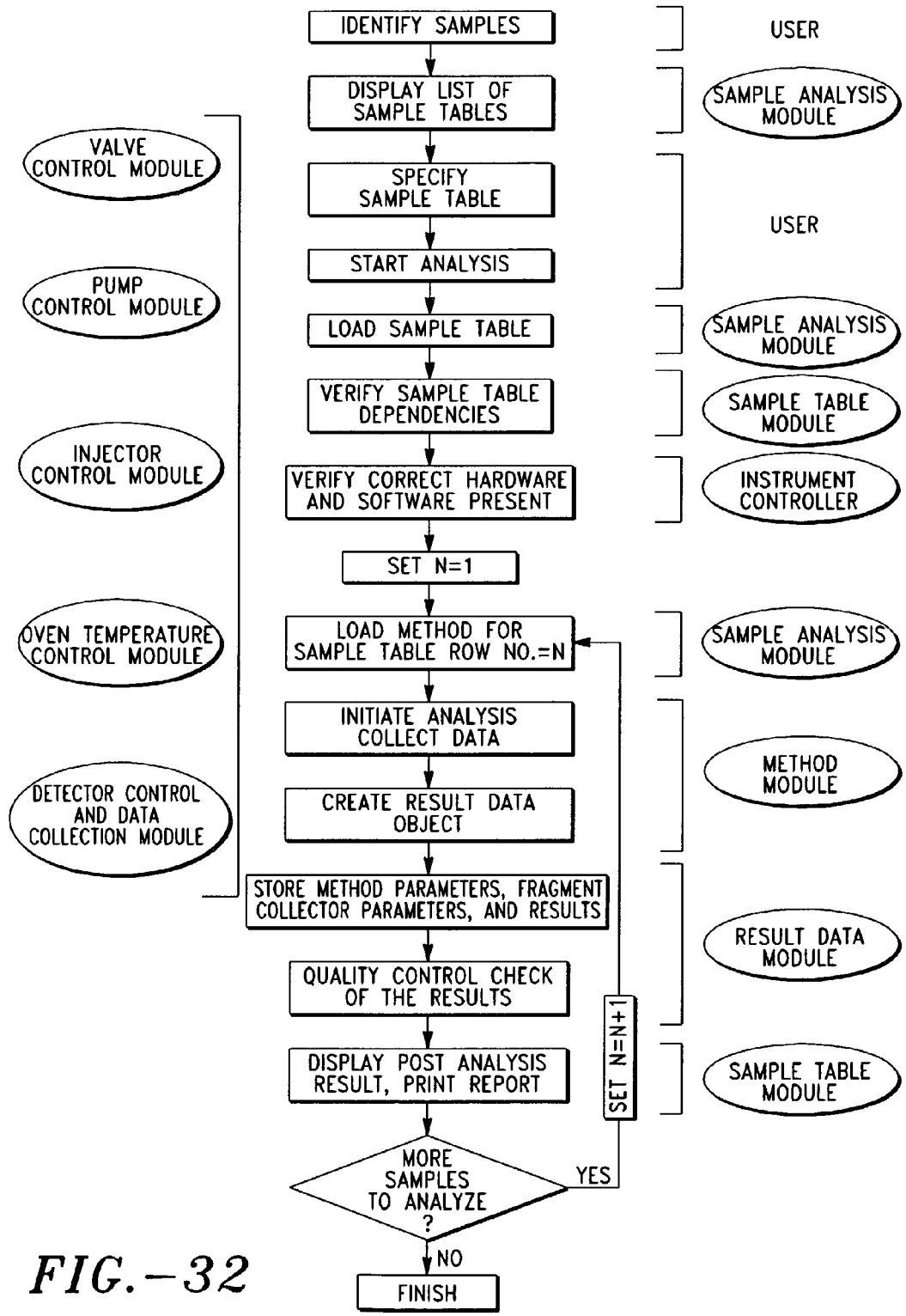
FIG. 32 is a schematic representation of another embodiment of the MIPC system computerized control process and the modules associated with each portion of the process.

Also, a plurality of different samples can be analyzed. FIG. 32 is a flow chart representation of an embodiment of the MIPC system which can perform analysis of a plurality of different samples, e.g., by including a counter routine in the software. In this case, each individual sample can contain a different range of fragment lengths of interest, for example. Prior to the injection of a particular sample, the column is equilibrated, such as shown at 572 in FIG. 30, with a mobile phase having an organic solvent concentration low enough so that the DNA, to be later eluted, collects at the head of the column when the injection is made.

As shown in FIG. 30, a separation cycle consists of three major steps: deposition phase 574, separation phase 576, and cleaning phase 578. All DNA fragments which a user is interested in must be eluted during the separation phase 576 of the mobile phase gradient. In order to achieve a high resolution separation, a gradient slope of the separation phase 576 must have a very low growth speed. On the other hand, in order to shorten a cycle time of a DNA separation process, the separation phase 576 of the solvent gradient should be as short as possible. In order to achieve these objectives, the computerized HPLC system of the instant invention determines a % B at which the shortest DNA fragment of interest will be eluted and a % B at which the longest DNA fragment of interest will be eluted. The system then starts separation phase 576 of a separation cycle closely before % B at which the shortest DNA fragment of interest is eluted and starts the cleaning phase 578 of the separation cycle closely after % B at which the longest DNA fragment of interest is eluted.

The system has several options for establishing a mobile phase gradient for DNA fragment separation process. A user can provide all gradient information in a form of a table with time points (or intervals) and corresponding levels of solution B. Alternatively, a user can provide a level at which a separation phase 576 of the gradient begins (% $B_2$), a level at which the separation phase 576 ends (% $B_3$), and a speed of the gradient growth. The shape of the gradient, such as linear, concave, convex or other shape, can also be selected. This data will fully define the separation gradient.

Alternatively, the computer 500 includes solvent concentration and gradient computing software for computing the solvent gradient beginning and ending solvent concentrations.

In a preferred embodiment, the invention provides solvent concentration and gradient computing software for computing the solvent gradient beginning and ending solvent concentrations to be used in the separation.

In one embodiment, a Universal Gradient is available as described in Example 1. In a preferred embodiment the system includes software that provides preferred levels for % $B_2$ and % $B_3$ in the mobile phase for the separation gradient based on the base pair lengths of the DNA fragments of interest. When analyzing a mixture of DNA fragments, the user enters the bp values of the shortest and the longest of DNA fragments of interest, or the base pair lengths of the fragment(s) of interest in the mixture, and these values are used in the calculation of preferred mobile phase composition. When analyzing a single fragment, only one bp length need be entered, and the software calculates a gradient to begin below a % B that will elute the fragment, and to end above a % B that will elute the fragment.

In one embodiment, corresponding solvent concentrations are calculated based on the base pair lengths of the DNA fragments in accordance with the hyperbolic formula (i) for a constant slope separation gradient:

$$\% B = p_1 + \frac{p_2 \cdot bp}{p_3 + bp} \quad (i)$$

where
% B is a percentage of an aqueous organic solvent solution used in the mobile phase;
bp is a base pair length of the DNA fragment of interest;
$p_1$, $p_2$, $p_3$ are system dependent coefficients.

Figure 33:
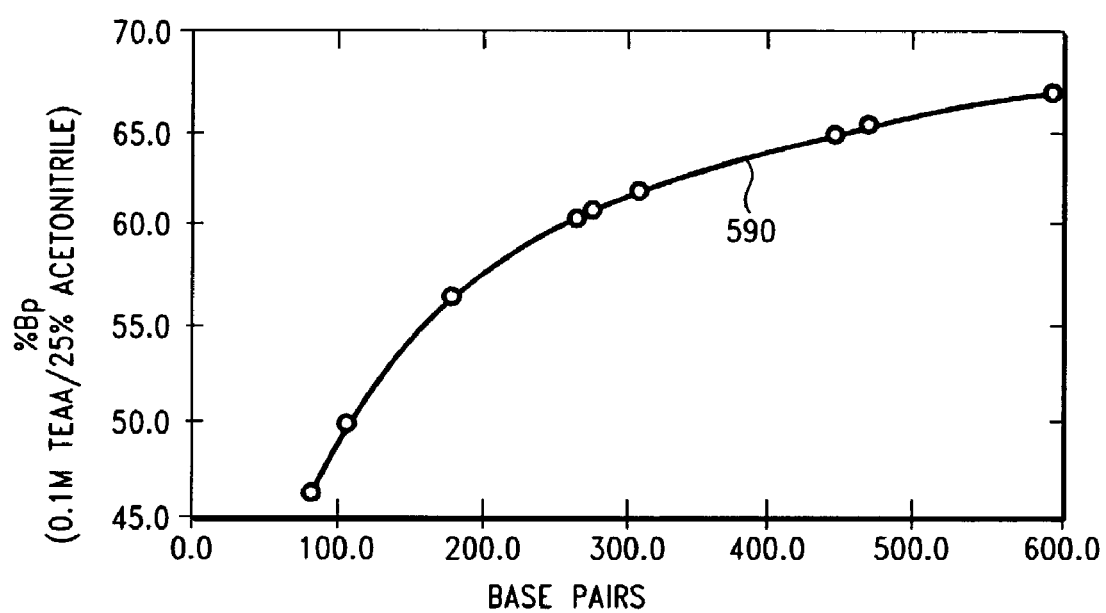
FIG. 33 is a reference chart showing percent of a solution B vs. base pair length for a standard mixture containing DNA fragments of known base pair length.

From analyses of standard mixtures of DNA fragments of known lengths, Applicants have determined the following values for the system dependent coefficients under the conditions described in Example 2 (and as shown in FIG. 33) using acetonitrile as organic solvent:
$p_1$=19.24
$p_2$=53.6
$p_3$=78.5

Formula (i) presumes a linear gradient of solvent concentration and is preferred when the same gradient is used for the calibration and for the actual run. Any slope can be used. However, the system dependent coefficients will then be different and must be determined by a calibration process which includes curve fitting of experimental data to an equation having the form of formula (i).

When using Equation (i), the retention time (Rt) for a fragment can be calculated from the following equation:

$Rt$=dead time+loading time+(% $B_{(calculated)}$-% $B_{(at\ start\ of\ gradient)}$)/slope where
% $B_{(calculated)}$ is the % B calculated from Equation (i);
dead time is determined as described in Example 3;
loading time corresponds to the time for gradient 574.

In other embodiments of the invention, other equations were fitted to the empirical data, and were used for prediction of mobile phase composition as described herein. For example, a linear equation having the form % B=$a_1$(bp)+$a_2$; a quadratic equation having the form % B=$a_1$(bp)$^2$+$a_2$(bp)+$a_3$; and a cubic equation having the form % B=$a_1$(bp)$^3 a_2$(bp)$^2$+ $a_3$(bp)+$a_4$ (with $a_1$, $a_2$, $a_3$, and $a_4$ being empirically determined constants) were used. In other embodiments, any equation having the appropriate shape within the range of interest can be used.

An essential, and heretofore unrecognized feature of the instant invention, is the discovery by Applicants that, under non-denaturing conditions, DNA fragments elute from an MIPC column based on their size, independently of base pair composition, at a particular organic solvent concentration for each size, and independently of the value of slope of the organic solvent gradient, and that this elution is highly reproducible using MIPC. Therefore, it is not necessary to calibrate a MIPC column for each sample analysis. Daily or even weekly calibrations are usually not necessary. Once a solvent concentration has been determined for a given base pair length, the % B to elute that size of fragment will be constant, not only from day to day on the same column, but also from one column to another. It is this surprising discovery that makes it possible to create a reference relating solvent concentration to base pair length and to predict a solvent concentration for eluting a DNA fragment of known base pair length without any additional methods development.

Although good results can be obtained with default values (obtained by previously analyzing a standard DNA mixture) and no calibration, preferred practice is to calibrate when a new column or eluant (buffer or mobile phase) is installed on the instrument. Highly accurate results can be obtained without the use of internal standards. The method can be used to predict when a fragment of known length will elute in a particular gradient, and can also be used to ascertain the molecular weight of an unknown fragment from its retention time in a particular solvent gradient. The predictability of the elution of DNA fragments facilitates optimization of a gradient for speed and resolution.

In another embodiment of a separation gradient formula, equation (ii) represents the % B that would be reached in the course of a linear gradient of slope s at which a specific fragment of a specific base pair length would elute:

$$\% B = \frac{1}{k} \ln\left[\frac{\exp(s \cdot d \cdot k) - 1}{\text{void}}\right] + \text{offset} \quad (ii)$$

where
$k = p_4 \cdot bp + p_5$ $$\text{offset} = p_6 + \frac{p_7 \cdot bp}{p_8 + bp}$$

% B is a percentage of an aqueous organic solvent solution used in the mobile phase;
s is a speed of concentration growth (i.e. the slope);
d, void, $p_4$, $p_5$, $p_6$, $p_7$, and $p_8$ are system dependent coefficients.

From statistical curve fitting analysis of standard mixtures of DNA fragments of known lengths, Applicants have determined the following preferred values for the system parameters to be used with an MIPC system equipped with a DNASEP column (50 mm×4.6 mm i.d.) available from Transgenomic, Inc. (San Jose, Calif.) under the elution conditions indicated in Example 2:
d=2.0;
void time=1.95;
$p_4$=9.596×10$^{-4}$;
$p_5$=0.417;
$p_6$=25.4;
$p_7$=45.2; and
$p_8$=85.0.

In Equations (i) and (ii), other system parameters will be obtained, after curve-fitting, for chromatography systems which employ different reverse phase separation columns, different separation conditions, or different system components. For example, system components from a variety of vendors are available (e.g., Hewlett-Packard, Varian, Beckman Coulter, Waters, Shimadzu) and can be used in the present invention. However, the general form of the equations will be unchanged.

Figure 34:
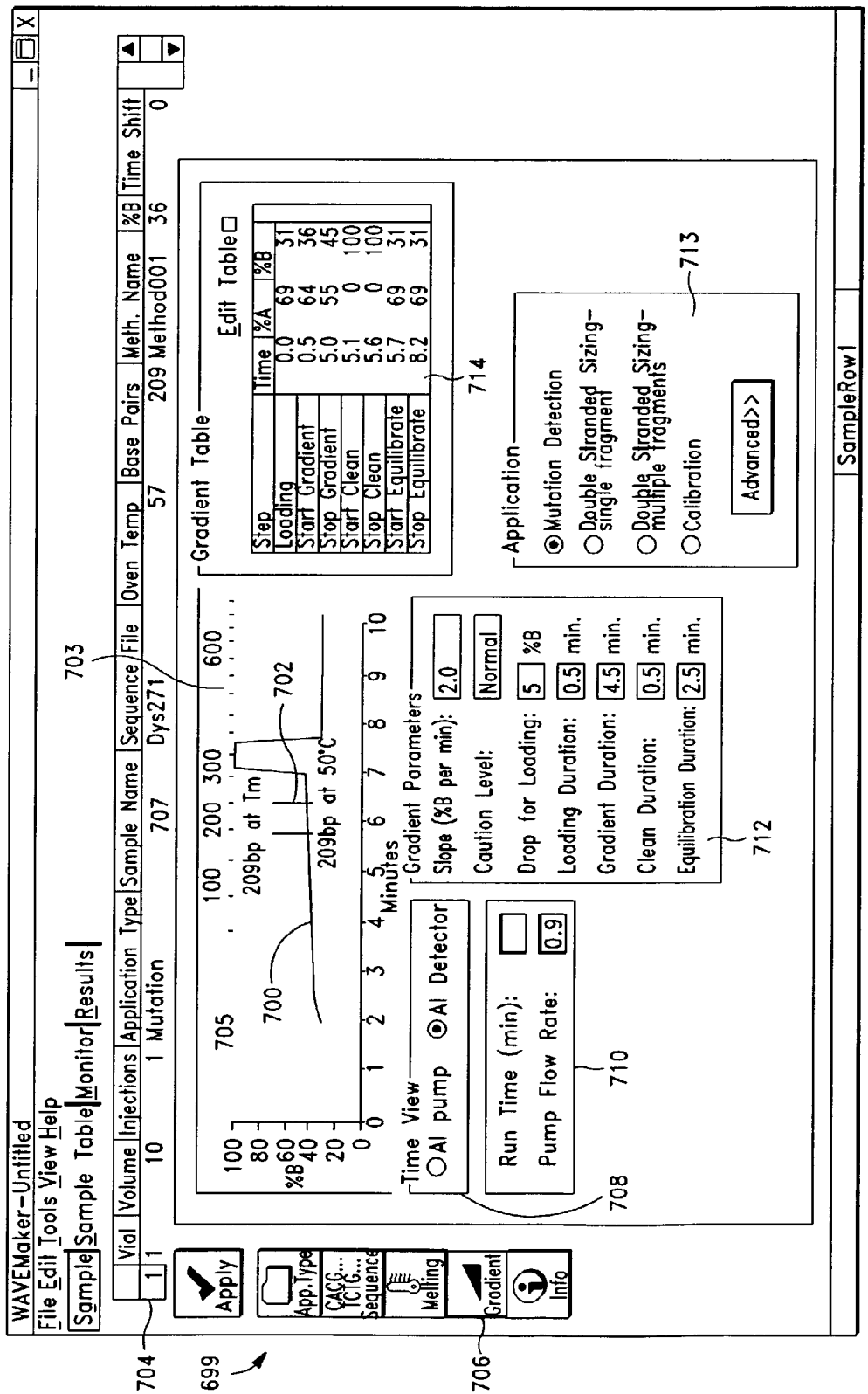
FIG. 34 illustrates an embodiment of a graphical user interface for viewing the mobile phase gradient profile.

The preferred software of the instant invention provides a user interface for entering the fragment length, in base pairs, of the DNA to be separated. The software generates a graphical user interface on a display device such as a crt or flat panel monitor. An example of a user interface is a Gradient Template 699 as illustrated in FIG. 34. Based on the fragment length in base pairs, the software sets the following: the slope of the linear gradient, the duration and change in % B of the loading step, the duration of the gradient, the duration of the clean off, the duration of the post clean-off equilibration, and the start and finish of the gradient.

In the example illustrated, the slope of the linear gradient is shown at 700 and a predicted Rt for a DNA fragment at 50° C. is shown by vertical bar 702. The interface includes a table 704 for entering or viewing sample data such as vial number, injection volume, number of injections, application type, sample name, sequence file, oven temperature, base pairs, method name, % B at the start of the separation gradient, and time shift. The interface includes a click button 706 for calculating the mobile phase gradient. The interface also includes a panel 708 for determining the location of the gradient to be displayed, either at the pump or at the detector; a panel 710 for viewing or entering the run time and plump flow rate. When displaying the gradient at the detector, two features are preferably included. The first is two vertical dashed lines, 705 and 707, that represent the beginning and end of the section of the gradient where the Equation (e.g., Equation (ii)) applies. The second is numbered hash marks 703 that indicate the times at which fragments of defined size would elute past the detector.

A panel 712 shows various gradient parameters: Gradient Slope in % B per minute; panel 712 includes a Caution Level having settings such as Cautious, Normal and Fast, which place predefined values in other fields (excluding the slope field) which are consistent with these setting names, as an alternative to editing each of the other fields; Drop for Loading indicates a drop in the % B for loading the DNA onto the column for allowing non-retained components (typically dNTPs, primers, buffers etc. when PCR products are injected) to pass through so that they do not influence the separation in an unpredictable manner; Loading Duration which provides the duration over which the Drop for Loading rises to the start of the linear gradient (typically 0.1 or 0.5 minutes); Gradient Duration which defines the length of time over which the % B will rise linearly at a % B per minute selected by the Slope option; Clean Duration which indicates the time for which the % B will remain at 100% to clean high molecular weight DNA from the column (The rise to 100% and drop from 100% occur in 0.1 min., for example.); Equilibration Duration which indicates the time for which the % B remains constant to equilibrate for the next injection.

The Gradient Template can also include a Fast Clean setting which is used if the clean-off portion of the gradient will be performed by the optional cleaning solution injector valve 54, as described hereinabove. When selecting the Fast Clean option, the clean-off portion of the gradient is eliminated because this function is performed by the valve 54 instead, allowing higher sample throughput. A field 714 displays a gradient table which can be edited by the user. A field 713 displays options for selecting an Application such as Mutation Detection, Double Stranded Sizing for a single fragment, Double Stranded Sizing for multiple fragments, and Calibration.

After calculation of the minimum and maximum solvent concentrations required, based on the provided lengths of DNA fragment(s) of interest, the Sample Analysis Module 550, through an interface such as the Gradient Table 699, displays these gradient parameters to the user who can either accept the system's suggestions or adjust the gradient parameters. After the gradient parameters are approved by the user, the parameters are stored in digital memory in a Method file, and Sample Analysis Module 550 forms a Sample Table which associates each sample with a Method.

If fragment collection of DNA fragments of the selected base pair lengths is desired, then the time of elution of such fragments will be calculated by the Sample Analysis Module 550 in accordance with the above-presented formulas. The Sample Analysis Module 550 calculates mobile phase compositions corresponding to elution of the DNA fragments of interest. Then, the corresponding retention time can be viewed in the Gradient Template. The resulting retention time is adjusted for system delay between elution of the DNA fragment from the column and its arrival at the fragment collector 88. These times for Blind Collection can be then presented to the user who can accept or adjust them. Based on this data a Fragment Collection Table is calculated by the Sample Table Module 552.

In mutation detection, in contrast to the situation where multiple fragments of differing size are present, only a single base pair length is entered by the user. Resolution of heteroduplexes from homoduplexes requires a gradient elution at a temperature which is just starting to melt the DNA. The heteroduplexes are destabilized by the mismatched bases and therefore are slightly more melted than the homoduplexes at this temperature. Retention time decreases as the DNA denatures and hence the more denatured heteroduplexes appear ahead of the homoduplexes. As described herein, the Sample Analysis Module 550 calculates the mobile phase gradient based on the base pair length, using Equation (i) for example. In a preferred embodiment, the calculation can also determine a gradient which reduces the time for analysis without loss of resolution, for example, by starting the gradient just below the % B at which the fragment elutes and stopping the gradient just after the peak of interest is past the detector. The Sample Analysis Module 550 can calculate a gradient which "brackets" the mobile phase composition associated with the single base pair length.

In one embodiment, the Sample Analysis Module 550 calculates optimized gradient parameters to place the DNA fragment just at the end of the linear gradient under non-denaturing conditions. If the % B required to do this is called X, then the gradient below can be calculated as shown:

| Time (min) | % B | Flow (mL/min) |
|---|---|---|
| 0 | X − 12% | 0.9 |
| 0.1 | X − 7% | 0.9 |
| 4.6 | X + 2% | 0.9 |
| 7.2 | 100 | 0.9 |
| 7.7 | 100 | 0.9 |
| 7.8 | X − 12% | 0.9 |
| 9.8 | X − 12% | 0.9 |

When analyzing multiple DNA fragments, the software can calculate optimized gradient parameters by placing the largest DNA fragment just at the end of the linear gradient and placing the smallest DNA fragments just at the beginning of the linear gradient. For example, the % B required to elute the smallest and the largest fragments can be determined. These values of % B determine a preliminary "fragment bracketing range". The fragment bracketing range has an initial % B and a final % B. The initial % B contains an organic solvent concentration up to an amount required to elute the first eluting DNA molecule in the mixture. The final % B contains an organic solvent concentration sufficient to elute the last eluting DNA fragment in the mixture. In a preferred embodiment, the initial % B of an optimized fragment bracketing range is less than or equal to about 15 percentage units below the initial % B. The final % B is at least about 5 percentage units higher than the final % B. Although the procedure described above is widely applicable in practice, it will be appreciated that initial and final solvent concentrations can be adjusted for specific applications.

Improved separation of mixtures of dsDNA fragments, and of mixtures of homoduplex and heteroduplex dsDNA fragments, can be achieved using MIPC under isocratic mobile phase conditions. The following equation (iii) can be used to determine the preferred mobile phase composition for separation of dsDNA fragments:

$$P = \frac{\text{void}}{\text{void} + \exp(-k(\% \ B - \text{offset}))} \quad \text{(iii)}$$

where $$k = p_4 \cdot bp + p_5$$

$$\text{offset} = p_6 + \frac{p_7 \cdot bp}{p_8 + bp}$$

P is a Partition fraction
% B is a percentage of an aqueous organic solvent solution used in the mobile phase; and where void, $p_4$, $p_5$, $p_6$, $p_7$, and $p_8$ are system dependent coefficients obtained from curve fitting such as described in relation to Equation (ii). In a preferred embodiment, these parameters have the same values as indicated in relation to Equation (ii).

Partition fraction is proportional to the velocity of the DNA fragment through the column. At P=0 the DNA is stationary, while at P=1, the DNA is moving with the maximum velocity (equal to that of the void peak).

Figure 35:
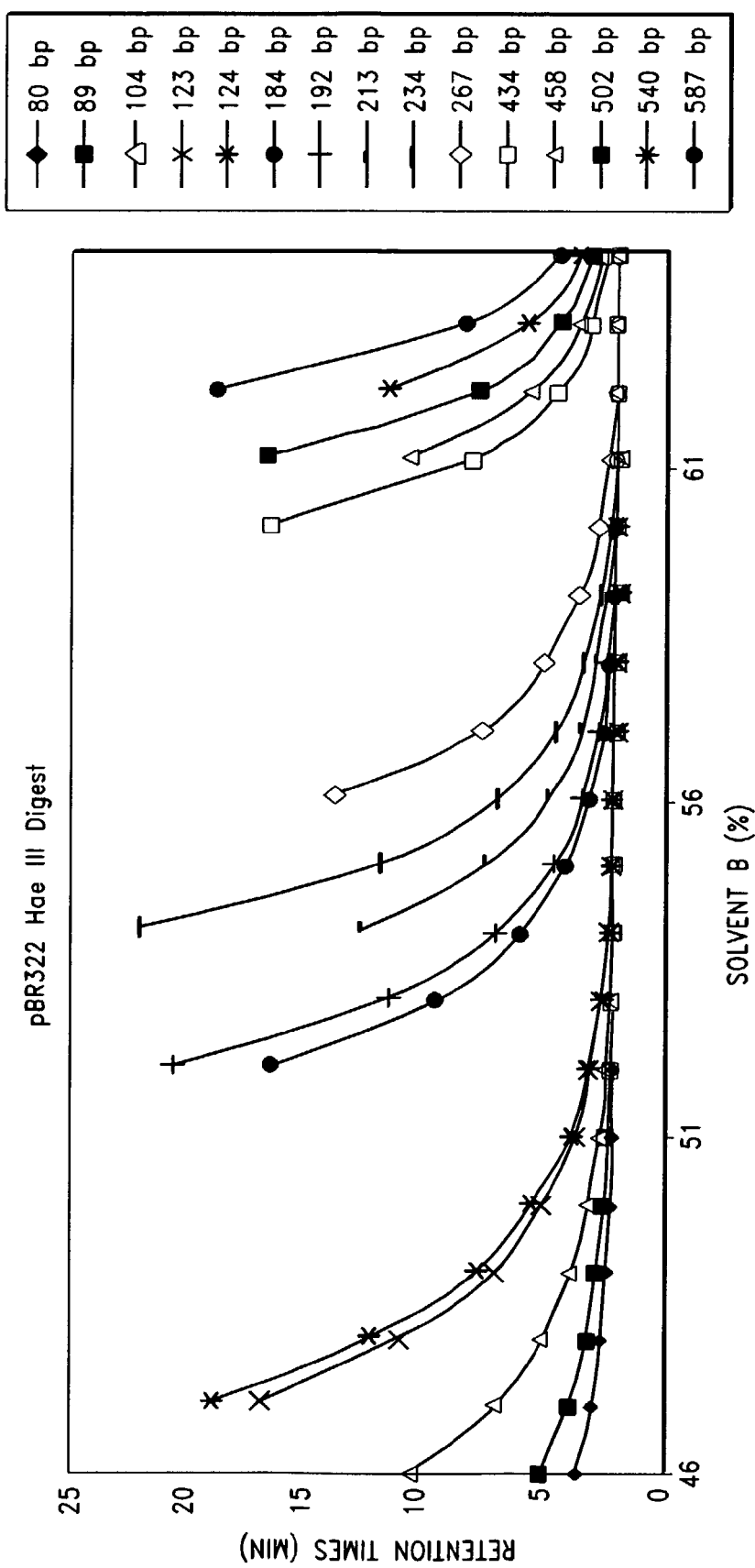
FIG. 35 shows a plot of Rt vs. % B for DNA fragments from a pBR322 HaeIII digest.
Figure 36:
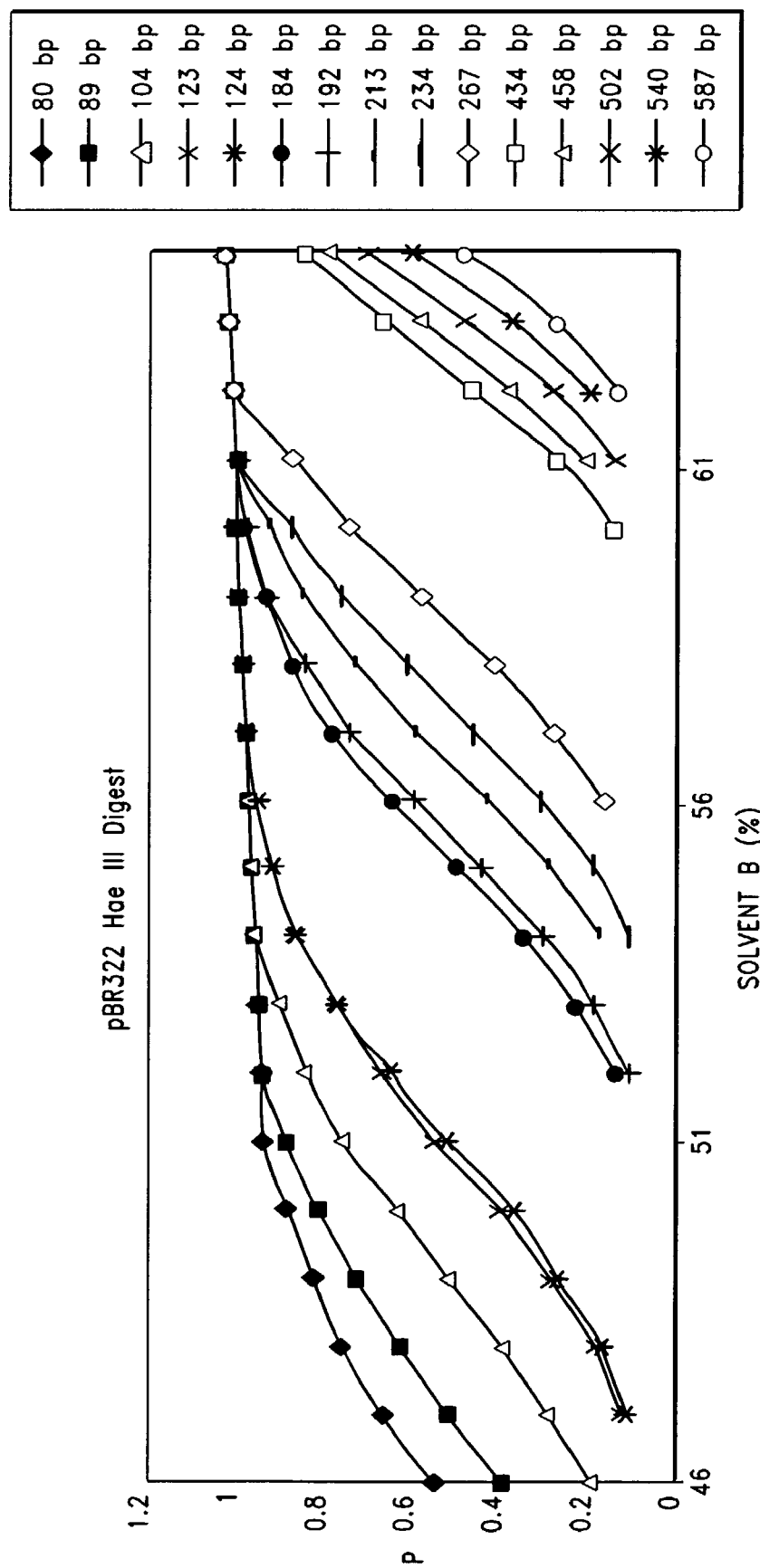
FIG. 36 shows a plot of P vs. % B for DNA fragments from a pBR322 HaeIII digest.

In order to derive equation (iii), a series of isocratic elutions of the mixture of fragments from a pBR322 HaeIII digest, were performed under conditions described in Example 1 except that the column was eluted with an isocratic mobile phase at every integer % B from 50 to 65%. A plot of Rt vs. % B was prepared (FIG. 35). Using the observed value of the void time (1.95), the data from FIG. 35 were recalculated and plotted in FIG. 36. Calculated curves using Equation (iii) were generated as shown in FIG. 37.

Figure 37:
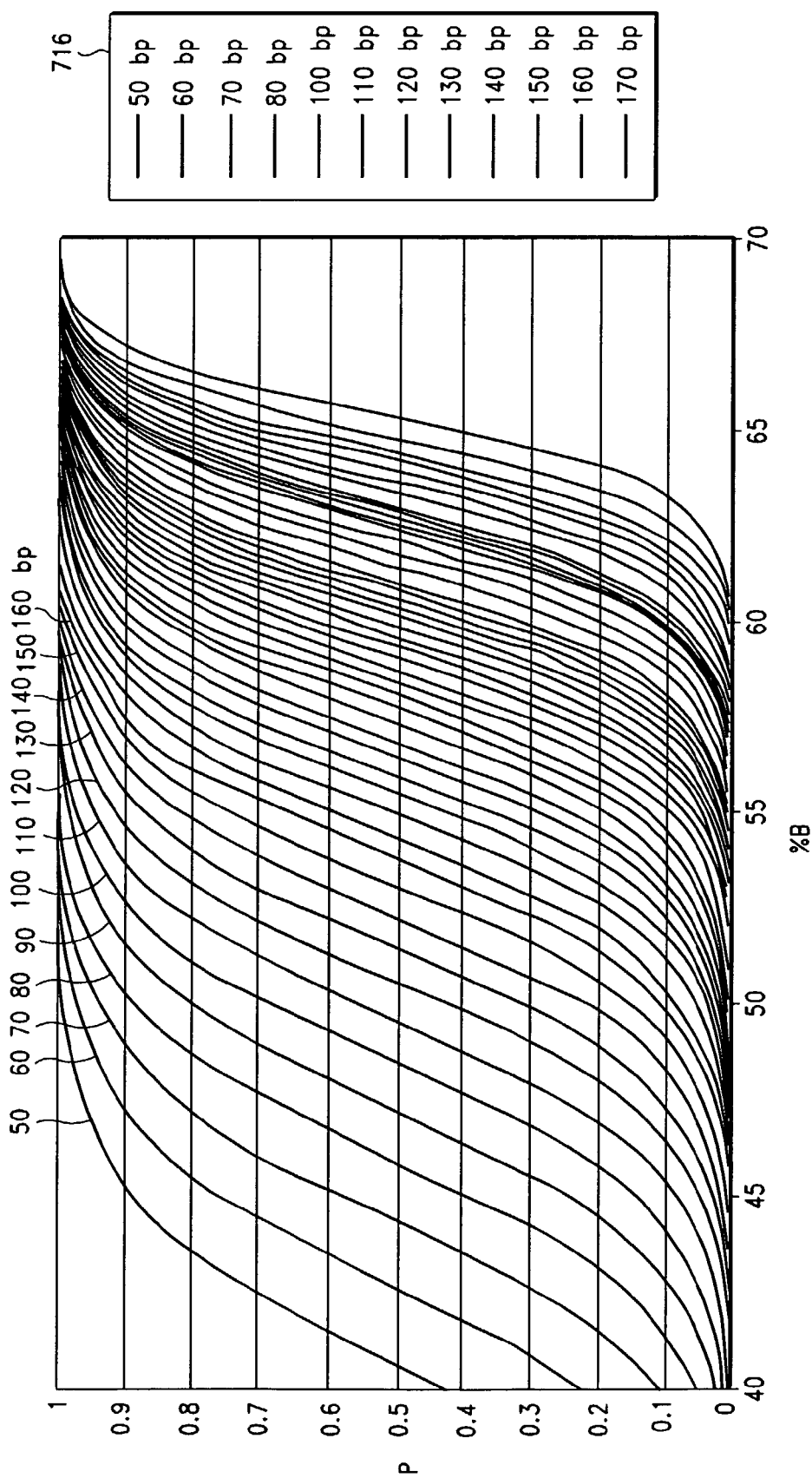
FIG. 37 shows a calculated plot of P vs. % B.

In one embodiment of a method of using Equation (iii), the calculated data of FIG. 37 can be stored in digital memory. To predict the isocratic elution profile of one or more fragments of DNA, the software performs a "table look up" of the stored data at any selected % B and determines a P value for a given fragment length. For convenience, a graphical user interface shows the plot of FIG. 37, and the user selects a % B by inspection based on the lengths of the fragments as indicated in the legend 716. When a % B is selected, a user interface, such as a Gradient Template, shows a preview plot of the predicted retention time(s).

Figure 43:
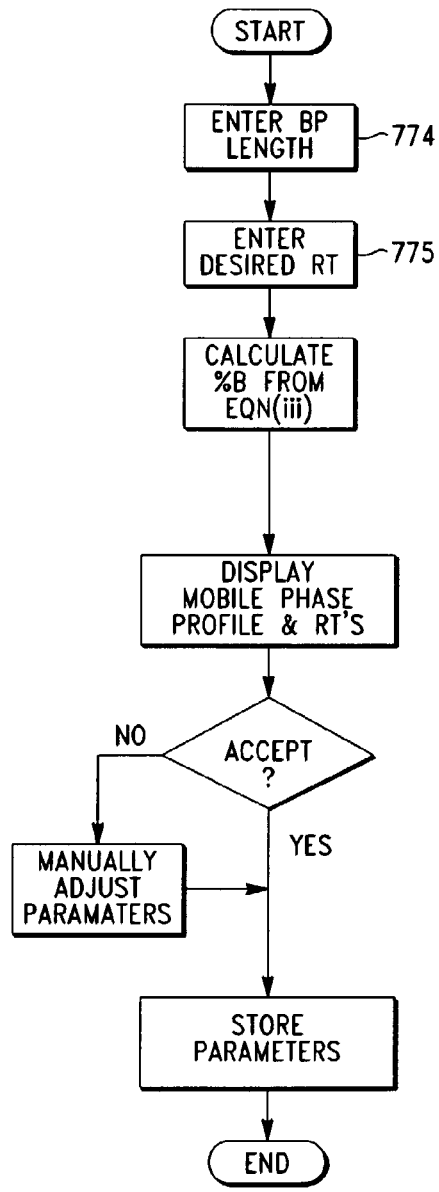
FIG. 43 is a flow diagram showing the operation of an embodiment of software for calculating mobile phase isocratic gradient to be used to separate DNA heteroduplex and homoduplex fragments having a known base pair length by DMIPC.

In another embodiment of a method of using Equation (iii), the user is prompted to input the base pair length and the desired retention time. A value of P is calculated by the software from the relationship P=(void volume)/(desired retention time) and Equation (iii) is then used to determine the value of % B. The display, such as a Gradient Template, shows the mobile phase profile and preferably also displays the predicted retention time of the fragment or fragments of interest. A flow diagram illustrating the software steps of this embodiment is shown in FIG. 43.

In using Equation (iii), the void volume of the instrument must have been predetermined and entered into the computer memory. For example, a value of 1.95 mL for the void volume was determined as described in Example 2.

It will be appreciated that by changing the start and end points of the separation gradient that the separation of selected base-pair length fragments can include a separation of all of the fragments within a mixture of DNA fragments, or can include a separation of one or more fragments within a mixture of DNA fragments.

The present invention takes advantage of the highly reproducible relationship between the concentration of organic solvent in the mobile phase, required to elute DNA fragments from an MIPC column, and the base pair length of the DNA fragments. Once a solvent concentration has been determined for a given base pair length, the retention time of that fragment will be constant at that solvent concentration, not only from day to day on the same column but also from one column to another. This reproducible quality makes it possible to create a reference relating solvent concentration to base pair length and to predict a solvent concentration for eluting a DNA fragment of known base pair length without any additional methods development.

Although good results can be obtained with the default values and no calibration, preferred practice is to calibrate when a new column is used with the instrument or when fragments are consistently eluting earlier or later than expected. Calibration of the separation column is accomplished by determining the % B required to elute one or more DNA fragment(s) of known size. An example of a full calibration procedure is described in Example 2 in which standard fragments obtained from a pUC18 DNA-HaeIII digest were used. The standard has preferably three or more fragments of known size. The standard's peaks preferably resolve well for the calibration and enough standard must be used so that the peak heights average between 5-10 mV.

As one alternative to full calibration, a zero point calibration can be selected, in which the default values (such as the % B vs. bp values obtained as described in Example 2) within the computer memory are used, and no standards are analyzed.

As another alternative to full calibration, a single-point calibration procedure can be used, and is sufficient if all of the samples are of the same length. In the first step of this process, the user selects a Gradient Template page, selects the option Double-Stranded Sizing-single fragment, enters the fragment size in the Base-pairs field, and presses an Update button. The user examines the predicted gradient and predicted retention time, checks that the oven Temperature field is set to 50° C., and injects the sample. After the analysis, the results are reviewed, and compared to the predicted retention time. If the predicted and observed retention times differ by more than 0.5 min, the user enters the observed retention time in a Calibration Dialog Box (not shown) and makes a selection to force re-calibration based on the observed retention time.

When a second calibration point is required, e.g., for a fragment of very different size (e.g., more than 50% different in size) to the first standard, the user can use a Second Point, step-wise calibration to calibrate with a second standard without altering the gradient that is predicted for the first standard. The user can run the second point calibration at any time after the first point calibration. In this process, the user selects the Gradient Template page, selects the option Double-stranded sizing-single fragment, and enters the fragment size that will be used. This is preferably at least 50% different in size from the first standard. The user then presses an Update button. The user examines the predicted gradient and predicted retention time, checks that the oven Temperature field is set to 50° C., and injects the sample. After the analysis, the results are reviewed, and compared to the predicted retention time. If the predicted and observed retention times differ by more than 0.5 min, the user enters the observed retention time for the second standard in a Calibration Dialog Box (not shown) and makes a selection to force re-calibration based on the observed second standard retention time.

Figure 38:
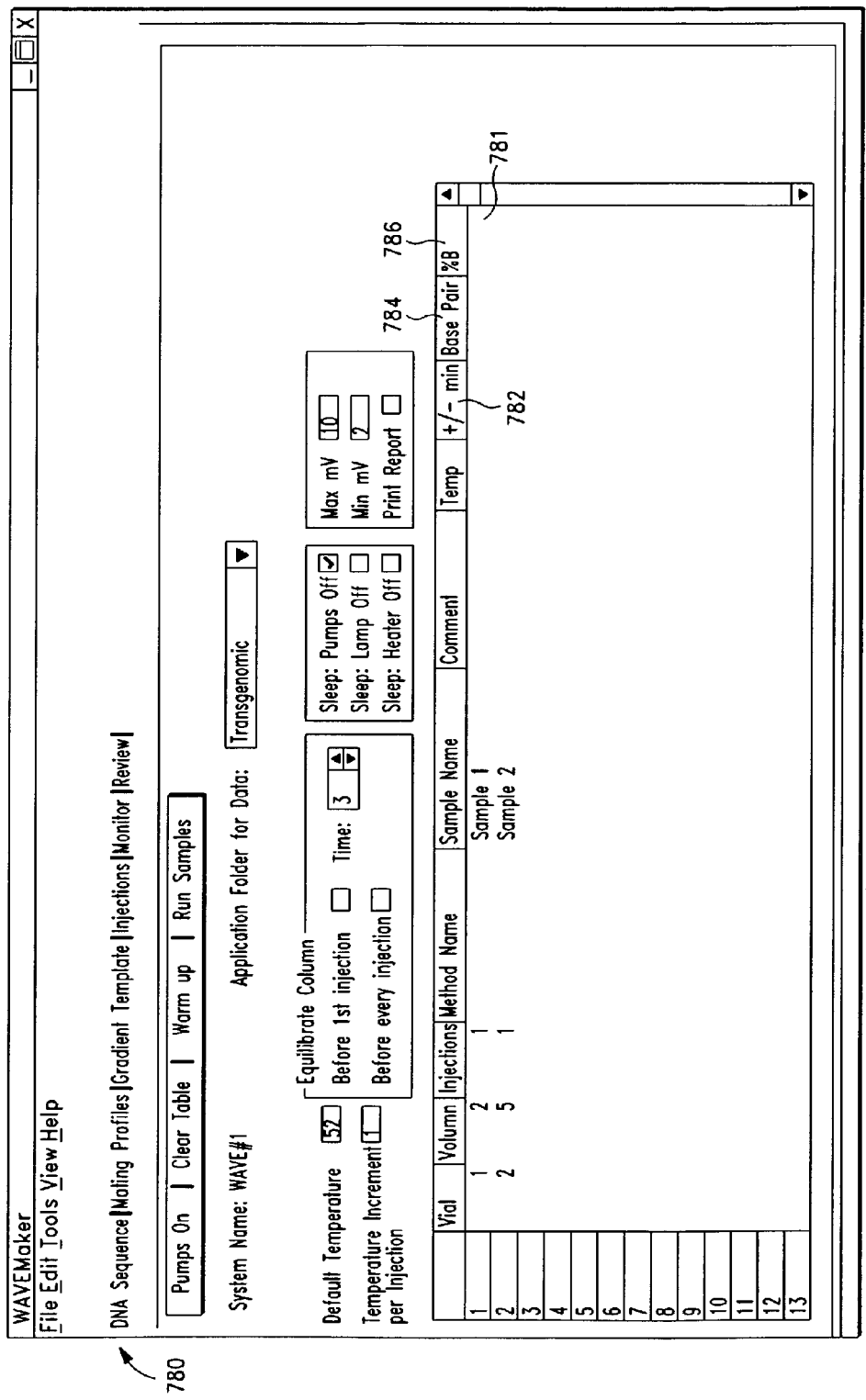
FIG. 38 illustrates an embodiment of a graphical user interface comprising a Sample Table.

In another embodiment of a graphical user interface, FIG. 38 shows an embodiment of an Injection Table 780. The Injection Table includes a Sample Table 781 which provides for entry of vial number, volume for injection, number of injections, method name, sample name, comments, and temperature. The rightmost three columns provide options for modifying the gradient. The column 782, labeled "−/+ min", offsets the % B in all of the Gradient Table rows 714, according to the formula Value·slope. Thus, with a slope of 2% per minute, an entry of −1 decreases % B in all rows except clean off by 2%. This decrease in % B will give peaks a 1 minute increase in retention time. The column 784, labeled "Base Pairs", offsets the Gradient Template (except the clean off) by the percentage required for a DNA fragment of the stated length. For example, if the Gradient Template assumes a 207 bp fragment length, and the user wants to run a 392 bp fragment using the same template, entering 392 in column 784 will offset the gradient by 3% B. The actual % B change might vary depending on the calibration of the column. The column 786, labeled % B, allows the % B for the start of the gradient to be set explicitly. The slope set in the Gradient Template is maintained. The value entered in column 786 overrides those in either columns 782, or 784. Preferably, the settings in columns 782, 784 and 786 can be adjusted "on the fly", while the software is running, so that the user can make adjustments to upcoming sample parameters based on previously obtained results.

In one embodiment, using the Gradient Template, when a plurality of fragments are being analyzed, a user can modify a gradient, for example by creating a multi-step gradient, in order to increase the resolution between peaks.

The Injection Table preferably also includes the following options: Pumps On which tuns the pumps on or off; clear Table which deletes all entries in the Sample Table; Warm Up which provides a safe low flow rate (e.g. 0.2 mL/min) while the oven warms; Run Samples which runs the sample listed in the Sample Table; Application folder which indicates the application folder where the results will be stored; Default temperature which indicates the oven temperature to be used as the default (This temperature was determined for the selected sequence on the DNA Sequence screen.); Temperature Increment which shows the value of the temperature increment for each injection if there is more than one injection indicated for a sample (The default is set to 1). The Injection Table can also include options for equilibrating the column, such as the duration or the time within and analysis; settings for generating a printed chromatogram; and options for turning off the pump, detector lamp, or heater after an analysis has terminated.

The software of the invention can also include an interface for displaying a Results Table (not shown) which lists information, including a data file location, for available samples. Chromatograms from one or more samples can be selected for viewing.

The software implementation for the present invention is within the skill of the art, and is dependent on such factors as the particular computer, or computers used, and the operating systems. Likewise, the connections between the computer and the HPLC need not be hard wired. It is possible to use infrared or other electromagnetic radiation to relay the control functions to the HPLC, with appropriate modulators/demodulators of common design. The computer 500 (FIG. 1) or an equivalent logic implementing unit, commands the logic and operation of the MIPC system. Preferably, a single computer, for example an IBM-PC or IBM-PC compatible computer running a multi-tasking operating system such as OS/Warp, a product of IBM Corporation, Windows-98, or Windows-NT, both products of Microsoft Corporation, are used.

The computer 500 is preferably equipped with appropriate memory, hard and floppy disk drives, video monitor, keyboard, pointing device, and other peripherals. The user interface and the gradient calculations as described herein are preferably implemented using software packages such as Visual Basic (Microsoft), C++, JAVA, or Delphi which are designed to integrate with Windows based operating systems. However, there is no reason why the system cannot be implemented on other computers with other operating systems, such as a Macintosh computer running Mac OS available from Apple Computer, Inc., or other computers available from Hewlett-Packard or Digital Equipment Corporation. Preferably, the software will be implemented to provide user-friendly screens to assist in entering the needed information and for reviewing and analyzing the results.

In one embodiment, the software described herein can include vendor-supplied software which can be customized for carrying out MIPC. For example, Hitachi makes accessible selected computer instructions which enable a user to develop customized software that integrates with HSM. HSM is described D-7000 HPLC System Manager User Manual (Part No. 810-9441-3), $4^{th}$ Edition (July 1996), which is incorporated by reference herein.

Figure 39:
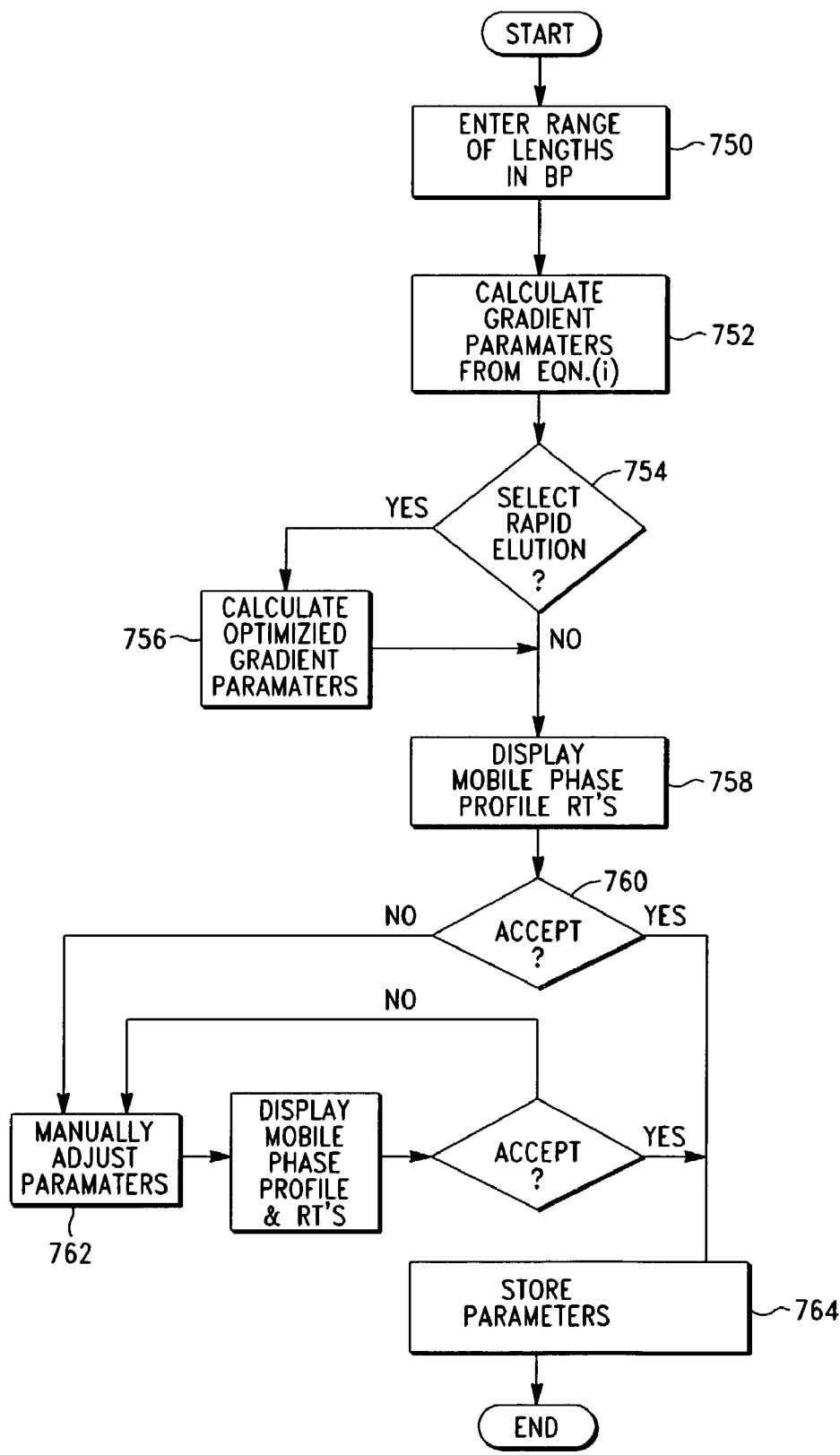
FIG. 39 is a flow diagram showing the operation of an embodiment of software for calculating mobile phase gradient to be used to separate DNA fragments having a range of base pair length by MIPC.

FIG. 39 shows a chart illustrating one embodiment of a solvent concentration and gradient computing software for computing the solvent gradient beginning and ending solvent concentrations. The user enters the length in base pairs of the fragments of interest at 550, and the software calculates the gradient parameters using Equation (i) at 552. The user can select to use optimized gradient parameters to accelerate the separation at 754,756. The mobile phase profile is displayed along with the retention times at 758. The user can manually adjust the parameters at 760,762. When the user accepts the parameters, the software stores them (as indicated at 764) in digital memory to be accessed by the Instrument Control Software.

Figure 40:
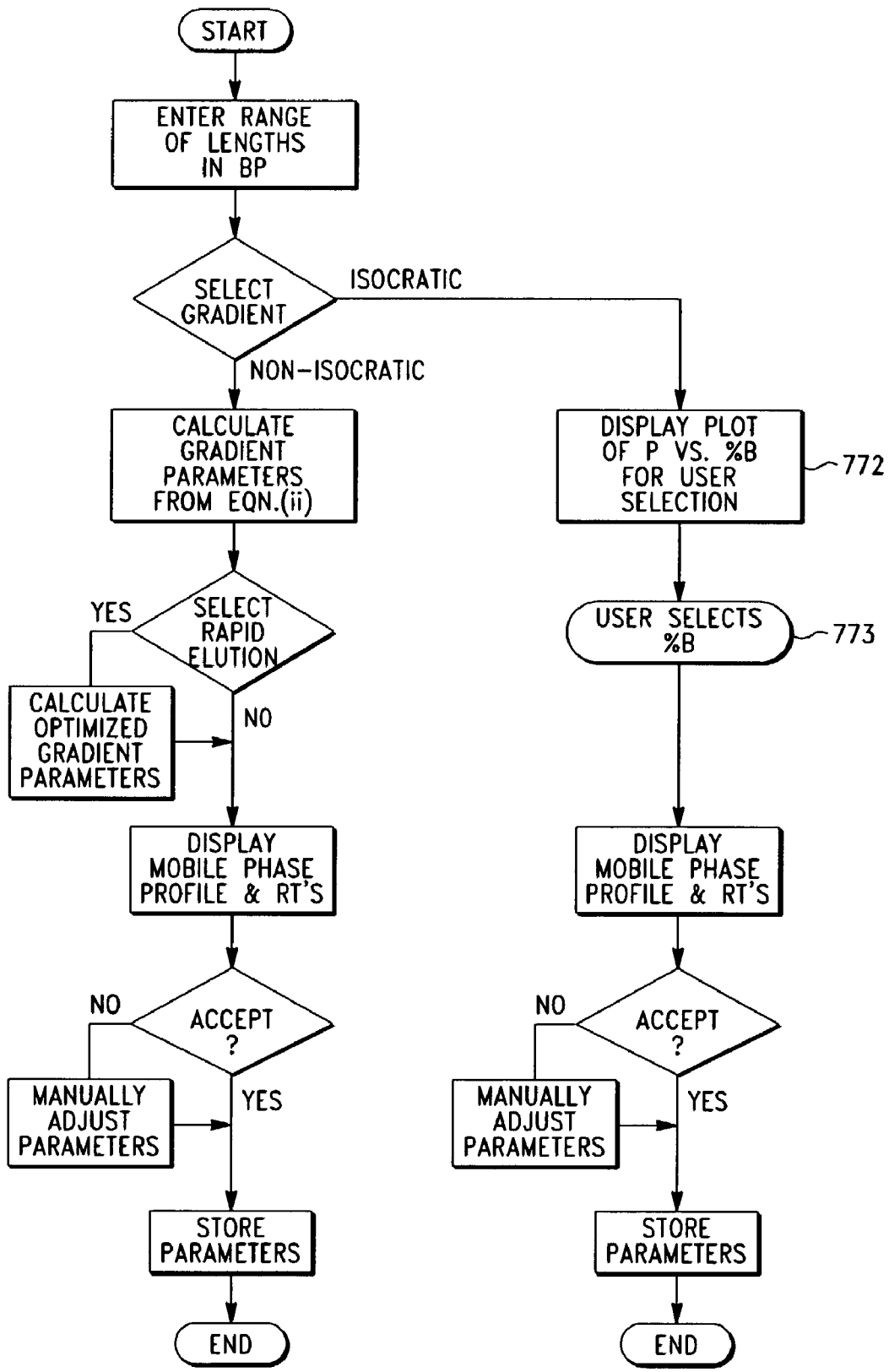
FIG. 40 is a flow diagram showing the operation of another embodiment of software for calculating mobile phase gradient to be used to separate DNA fragments having a range of base pair length by MIPC.

FIG. 40 shows a chart similar to FIG. 39 but illustrating the use of Equation (ii) in calculating the gradient parameters 770. The user also has the option of using an isocratic gradient, in which case a plot (such as shown in FIG. 37) is displayed at 772 and the user selects the % B as described hereinabove in relation to Equation (iii).

Figure 41:
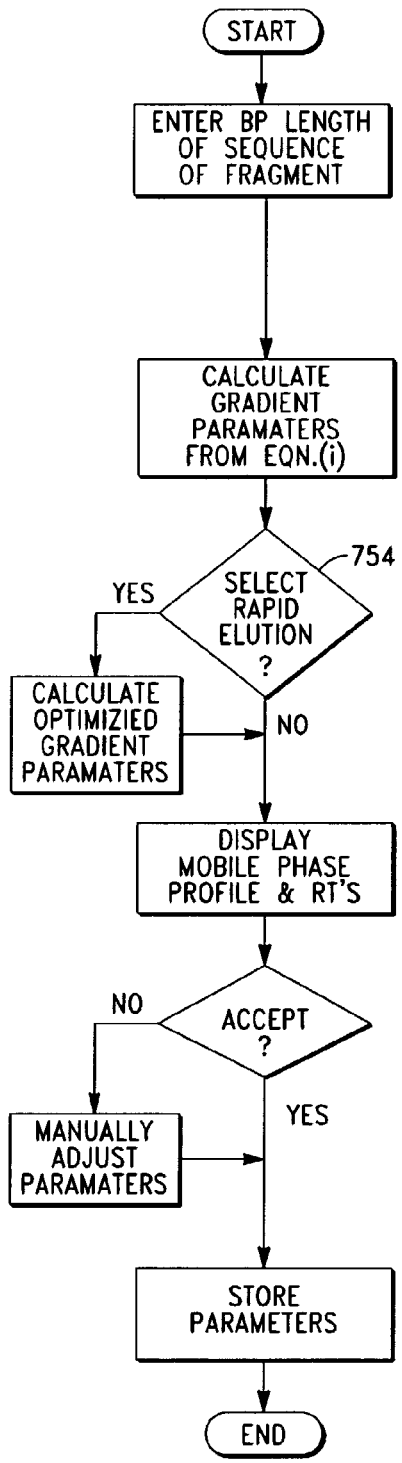
FIG. 41 is a flow diagram showing the operation of an embodiment of software for calculating mobile phase gradient to be used to separate DNA heteroduplex and homoduplex fragments having a known base pair length by DMIPC.

FIG. 41 is analogous to FIG. 39 except that only a single bp length is entered as would be the case for mutation detection.

Figure 42:
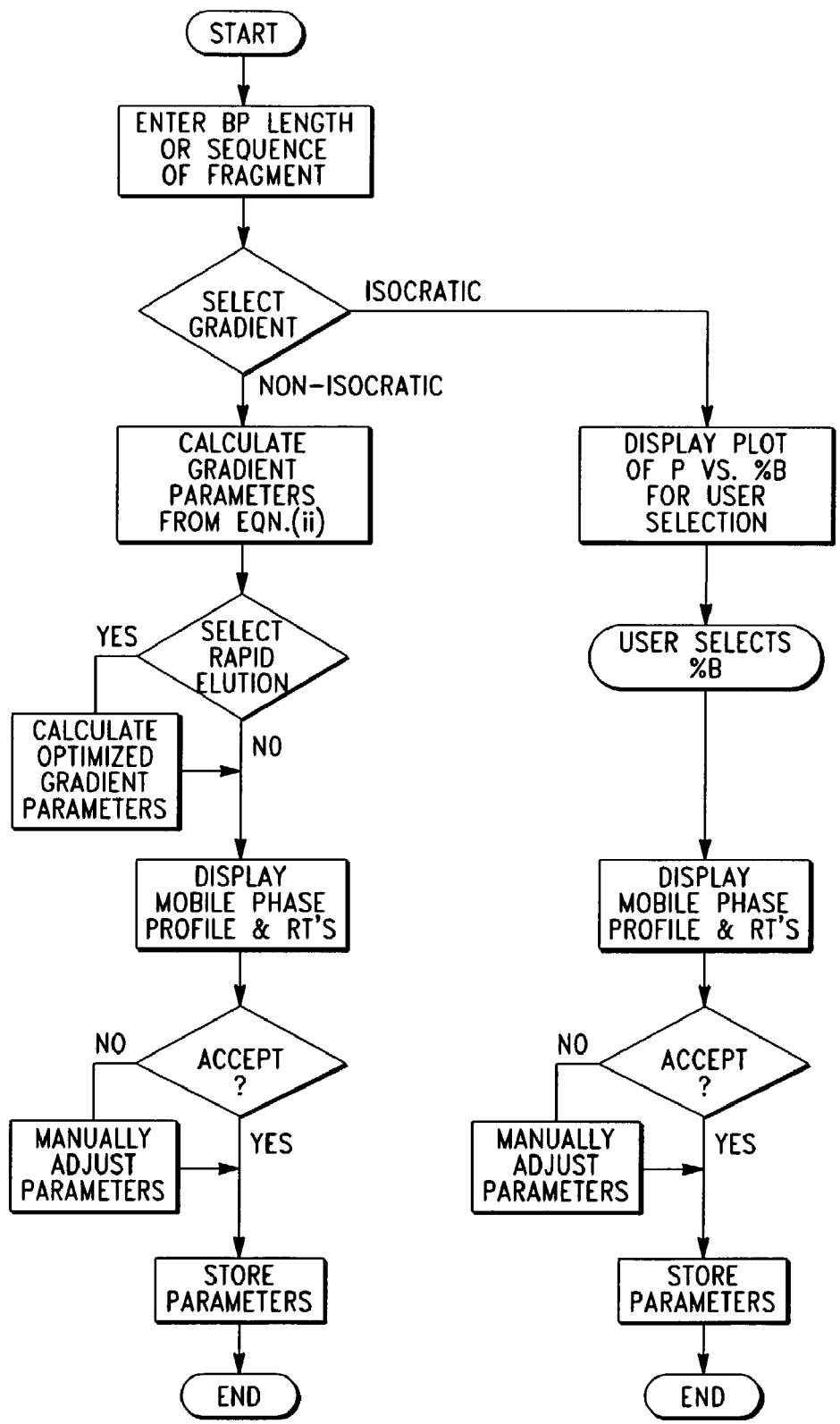
FIG. 42 is a flow diagram showing the operation of an embodiment of software for calculating mobile phase gradient to be used to separate DNA heteroduplex and homoduplex fragments having a known base pair length by DMIPC.

FIG. 42 is analogous to FIG. 40, but for a fragment of a single base pair length.

FIG. 43 illustrates the use of equation (iii) to calculate the % B. The user is prompted to enter the base pair length at 774 and the desired retention time at 775.

Another aspect of the present invention concerns a system and method for use in conducting DNA mutation detection. As discussed hereinabove, the instant invention can be used to detect mutations in double stranded DNA. The following definitions will be used herein:

The "melting temperature" is defined herein to mean the temperature at which 50% of the base pairs in a DNA fragment have separated from the complementary strand.

A "homoduplex" is defined herein to mean, a double stranded DNA fragment wherein the bases in each strand are complementary relative to their counterpart bases in the other strand.

A heteroduplex" is defined herein to mean a double stranded DNA fragment wherein at least one base in each strand is not complementary to at least one counterpart base in the other strand. This can be due to a mismatched base or a deletion. Since at least one base pair in a heteroduplex is not complementary, it takes less energy to separate the bases at that site compared to its fully complementary base pair analog in a homoduplex. This results in the lower melting temperature at the site of a mismatched base of a heteroduplex compared to a homoduplex.

The term "hybridization" refers to a process of heating and cooling a dsDNA sample, e.g., heating to 95° C. followed by slow cooling. The heating process causes the DNA strands to denature. Upon cooling, the strands recombine into duplexes in a largely statistical fashion. If the sample contains a mixture of wild type and mutant DNA, then hybridization will form a mixture of hetero- and homoduplexes.

The "heteromutant site separation temperature" T(hsst) is defined herein to mean the temperature which preferentially denatures the heteroduplex DNA at a site of mutation and which gives the greatest difference in the degree of denaturation between the heteroduplexes and homoduplexes. This is a temperature which is optimal to effect a chromatographic separation of heteroduplexes and homoduplexes by DMIPC and hence, detect mutations.

The term "heteromutant" is defined herein to mean a DNA fragment containing a polymorphism or non-complementary base pair.

The term "mutation separation temperature range" is defined herein to mean the temperature range between the highest temperature at which a DNA segment is completely non-denatured and the lowest temperature at which a DNA segment is completely denatured.

The term "mutation separation profile" is defined herein to mean a DMIPC separation chromatogram which shows the separation of heteroduplexes from homoduplexes. Such separation profiles are characteristic of samples which contain mutations or polymorphisms and have been hybridized prior to being separated by DMIPC. The DMIPC separation chromatograms shown in FIG. 45 which were performed at 51° C. to 61° C. exemplify mutation separation profiles as defined herein.

The term "temperature titration" of DNA as used herein is an experimental procedure in which the retention-time from DMIPC is plotted as the ordinate against column temperature as the abscissa.

Figure 44:
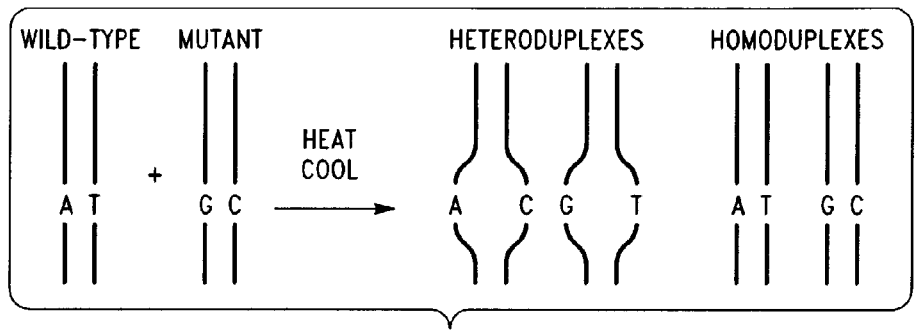
FIG. 44 shows a schematic representation of a hybridization to form homoduplex and heteroduplex.

A reliable way to detect mutations is by hybridization of the putative mutant strand in a sample with the wild type strand (Lerman, et al., Meth. Enzymol., 155:482 (1987)). If a mutant strand is present, then two homoduplexes and two heteroduplexes will be formed as a result of the hybridization process, as shown in FIG. 44. Hence separation of heteroduplexes from homoduplexes provides a direct method of confirming the presence or absence of mutant DNA segments in a sample.

An embodiment of the present invention is a method for selection of the T(hsst) based on the temperature titration. In this embodiment, a sample containing the mutation is examined at a series of temperatures using a heuristic optimization approach. The optimum temperature obtained by this procedure is the temperature at which the mutant DNA fragment is most easily distinguished from the wild-type DNA by the difference in the pattern of peaks.

In the present invention, the preferred software provides a user interface, such as a Sample Table, which allows the user to enter the temperature of the first injection. The default temperature is the predicted temperature (as described hereinbelow). However, the user has the option of entering any temperature. The user next enters the desired number of injections and the temperature increment per injection. The default value for the increment is 1° C. For example, if the predicted temperature is 55° C., and the user would like to perform a temperature titration of 5 injections to cover the range of 55+/−2° C., the user would first set the temperature as 53° C. in the Sample Table, and then set the number of injections to 5.

Figure 45:
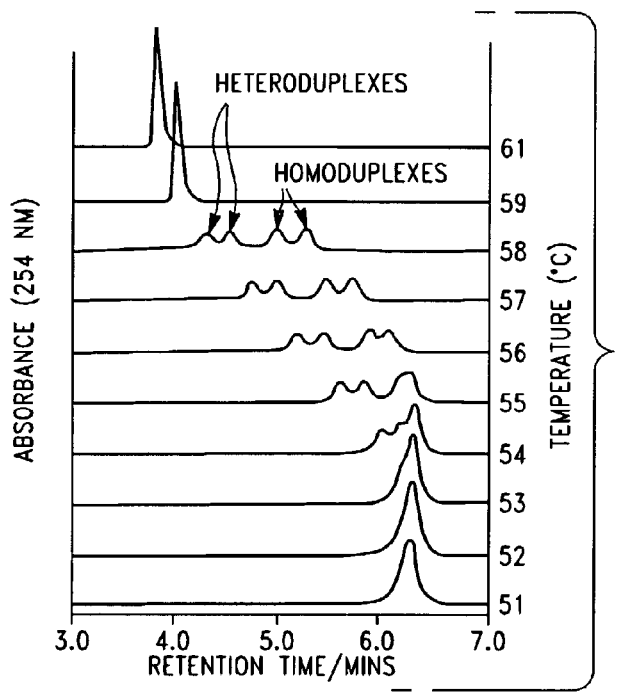
FIG. 45 illustrates a temperature dependent separation of homo- and heteroduplexes.
Figure 46:
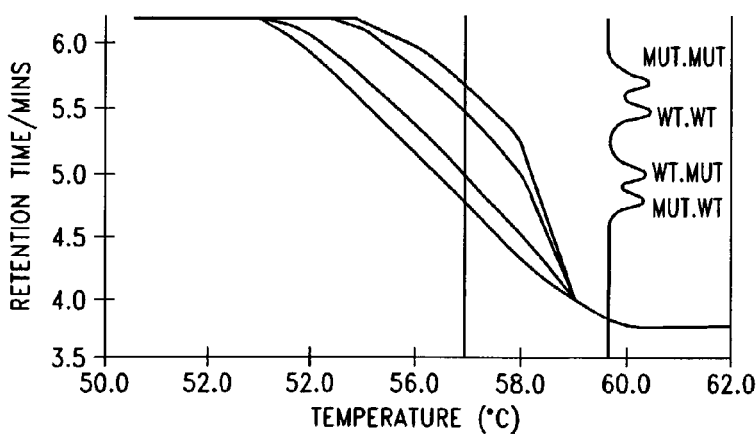
FIG. 46 shows the change in retention time with temperature of the peaks of the homo-and heteroduplexes from FIG. 45.

In one example of a temperature titration, the temperature dependent separation of a standard containing 209 base pair homoduplexes and heteroduplexes by DMIPC is shown in FIG. 45 as a series of separation chromatograms and the separation process is described in Example 4. The sample, containing a heterozygous sample of 209 base pair homoduplex fragments wherein the mutant fragments contained a single base pair deviation from the wild type, was hybridized by heating and then cooling. The hybridization process created 2 homoduplexes and 2 heteroduplexes as shown schematically in FIG. 44. As shown in FIG. 45, when MIPC was performed at 51° C., a single peak, representing all 4 mixture components, was seen. This result was expected since all 4 components have the same base pair length and the separation was performed at non-denaturing conditions, i.e., at a temperature too low to cause any denaturing. At 53° C. a shoulder appeared on the low retention time side of the main peak. This indicated the beginning of melting as well as the potential presence and the partial separation of a heteroduplex. As the temperature of the separation was increased incrementally, the original single peak was eventually separated into 4 clearly defined peaks. The 2 lower retention time peaks representing the 2 heteroduplexes and the 2 higher retention time peaks representing the 2 homoduplexes are shown in FIG. 45. The 2 homoduplexes separate because the A-T base pair, at locus 168, denatures at a lower temperature than the C-G base pair. Without wishing to be bound by theory, the results are consistent with a greater degree of denaturation in one duplex and/or a difference in the polarity of one partially denatured heteroduplex compared to the other, resulting in a difference in retention time on the MIPC column. A temperature titration of the homoduplex and heteroduplex species from the elution profiles of FIG. 45 is shown FIG. 46.

As seen in FIG. 45, the temperature range of 57° to 58° C. was optimal for this separation. The appearance of four distinct peaks was observed when a mutation was present in the original sample, in agreement with the expected results, based on the hybridization schematic in FIG. 44. Above that temperature the region containing the mutation is completely denatured. This is evidenced by the single peak, representing 4 equivalently denatured species, seen at low retention time when the separation was carried out at about 59°-61° C.

In some mutation analyses, only two peaks or a partially resolved peak(s) are observed in DMIPC analysis. The two homoduplex peaks may appear as one peak or a partially resolved peak and the two heteroduplex peaks may appear as one peak or a partially resolved peak. In some cases, only a broadening of the initial peak is observed under partially denaturing conditions.

If a sample contained homozygous DNA fragments of the same length, then hybridization and analysis by MIPC would only produce a single peak at any temperature since no heteroduplexes could be formed. In the operation of the present method, the determination of a mutation can be made by hybridizing the homozygous sample with the known wild type fragment and performing a DMIPC analysis at a partially denaturing temperature. If the sample contained only wild type fragments then a single peak would be seen in the DMIPC analysis since no heteroduplexes could be formed.

Applicants have developed a formula for predicting the heteromutant site separation temperature T(hsst). In general, this formula is expressed by the equation:

$$T(hsst) = X + m \cdot T(w) \qquad (iv)$$

wherein T(hsst) is the heteromutant site separation temperature, where X is the DMIPC detection factor, and m is a weighting factor selected between 0 and 2; both factors are used to adjust T(w) to the T(hsst).

In a particular embodiment of the invention, T(w) is the melting temperature determined from a UV melting profile of the normal (i.e. wild type) DNA duplex.

In another particular embodiment, T(w) is calculated by software as described hereinbelow. The values of m are preferably between 0 and 2.

A thermodynamic mathematical model of the melting behavior of known fragments can be used to predict the melting behavior of new fragments without any experimental work on the sample itself. The model is used to predict optimum temperatures for mutation detection and also to assess the suitability of the fragment to the technique. Modeling of melting behavior of DNA is well developed in the literature. However, the published thermodynamic melting procedures must be modified before they can be fully used for temperature prediction for mutation detection.

In a preferred embodiment of the present invention, a melting T(hsst) to be used in DMIPC analysis of a sample for mutation detection, is predicted by a mathematical model. As an example of a general approach, a predicted T(hsst) can be obtained by a method comprising a calculation step for obtaining a calculated T(hsst) and a prediction step for obtaining the predicted heteromutant site separation temperature. The calculation step comprises calculating a calculated heteromutant site separation temperature according to a first mathematical model. The prediction step comprises adjusting the calculated heteromutant site separation temperature according to a second mathematical model. Preferably, the second mathematical model is based on a comparison of empirically determined heteromutant site separation temperatures with calculated heteromutant site separation temperatures.

In one example of this approach, calculated melting temperature is derived using a first mathematical model such as the Fixman-Friere implementation of Poland's model. A predicted melting temperature is then derived by adjusting the calculated melting temperature according to a second mathematical model. A preferred example of a second mathematical model is an adjustment equation developed by comparing calculated temperatures based on the first model with empirically-determined temperatures observed from temperature titrations. The adjustment equation can be used to predict the T(hsst) of melting for DMPIC using only the sequence information of the wild type or homoduplex DNA. An adjustment of the Fixman-Friere calculated temperature is necessary to account for differences between the conditions used in obtaining the thermodynamic data (Breslauer et al. *Proc Nat. Acad. Sci USA* 83:3746 (1986), incorporated by reference herein) and the conditions used in DMIPC.

One illustration of an equation derived from a mathematical model is the following, which is a particular embodiment of Equation (iv):

$$Tm_{0.75}' = 19.6 + 0.68 \cdot Tm_{0.75} \qquad (v)$$

where $Tm'_{0.75}$ is the predicted temperature corresponding to 75% helical content and $Tm_{0.75}$ is the temperature calculated from the Fixman-Friere implementation of Poland's model (Poland, *Biopolymers* 13:1859 (1974) and Fixman et al., *Biopolymers* 16:2693 (1977), both reference incorporated by reference herein) using a σ value of 0.0001.

FIG. 47 is a graph of the calculated melting temperatures versus empirically observed melting temperatures. Equation (v) is derived from the solid line in FIG. 48 which represents a linear fit of the 40 points from FIG. 47. Also plotted on the graph of FIG. 48 are dashed lines representing one degree above and below the line representing $Tm_{0.75}'$. These dashed lines indicate that the accuracy of the predicted $Tm_{0.75}'$ may be expected to be within about one degree of the empirically determined values.

T(hsst) in Equation (v) was selected at 75% helical content because this gave the best agreement between experimentally observed temperature titration data and the predicted values for T(hsst). Those skilled in the art will recognize that other points on the empirical temperature titration curves can be selected, e.g., 50% or 90% helical content, and calculated temperatures can be obtained and adjusted as described hereinabove.

In other examples of using the above general approach for predicting T(hsst), the calculated melting profile of a fragment can be obtained using software such as MacMelt® (BioRad Laboratories, Hercules, Calif.), MELT (Lerman et al. *Meth. Enzymol.* 155:482 (1987)), or WinMelt™ (BioRad Laboratories).

Other equations giving predicted values for T(hsst) can be used in the instant invention, such as the equations described by Oefner et al *Current Protocols in Human Genetics*, Wiley & Sons, NY, Suppl. 19:7.10-7.10.12 and Jones et al. in *Clinical Chem.* 45:1133-1140 (1999), which references are incorporated by reference herein.

The predicted values for T(hsst) can be manually entered at a graphical user interface, such as a Sample Table for a particular sample.

In one embodiment of the present invention, the user enters the sequence of bases for the homoduplex wild type DNA, or enters the bp fragment length at a computer interface, and enters a value for a predicted T(hsst), which is stored in digital memory to be used by the oven temperature control software module in the analysis of the sample as described hereinabove.

In a preferred embodiment of the present invention, the user enters the sequence of bases for the homoduplex wild type DNA at a computer interface, software within the computer (or linked to the computer, such as through a network) for predicting T(hsst) generates a predicted T(hsst), which can optionally be reviewed by the user, and which is stored in digital memory to be used by the oven temperature control software module in the analysis of the sample as described hereinabove.

In another preferred embodiment, the user enters the sequence of bases for the homoduplex wild type DNA at a computer interface, and both the software for predicting T(hsst) and the software for computing the solvent concentration and gradient together generate all of the method parameters needed, which can optionally be reviewed, and the DMIPC analysis is carried out automatically.

Figure 49:
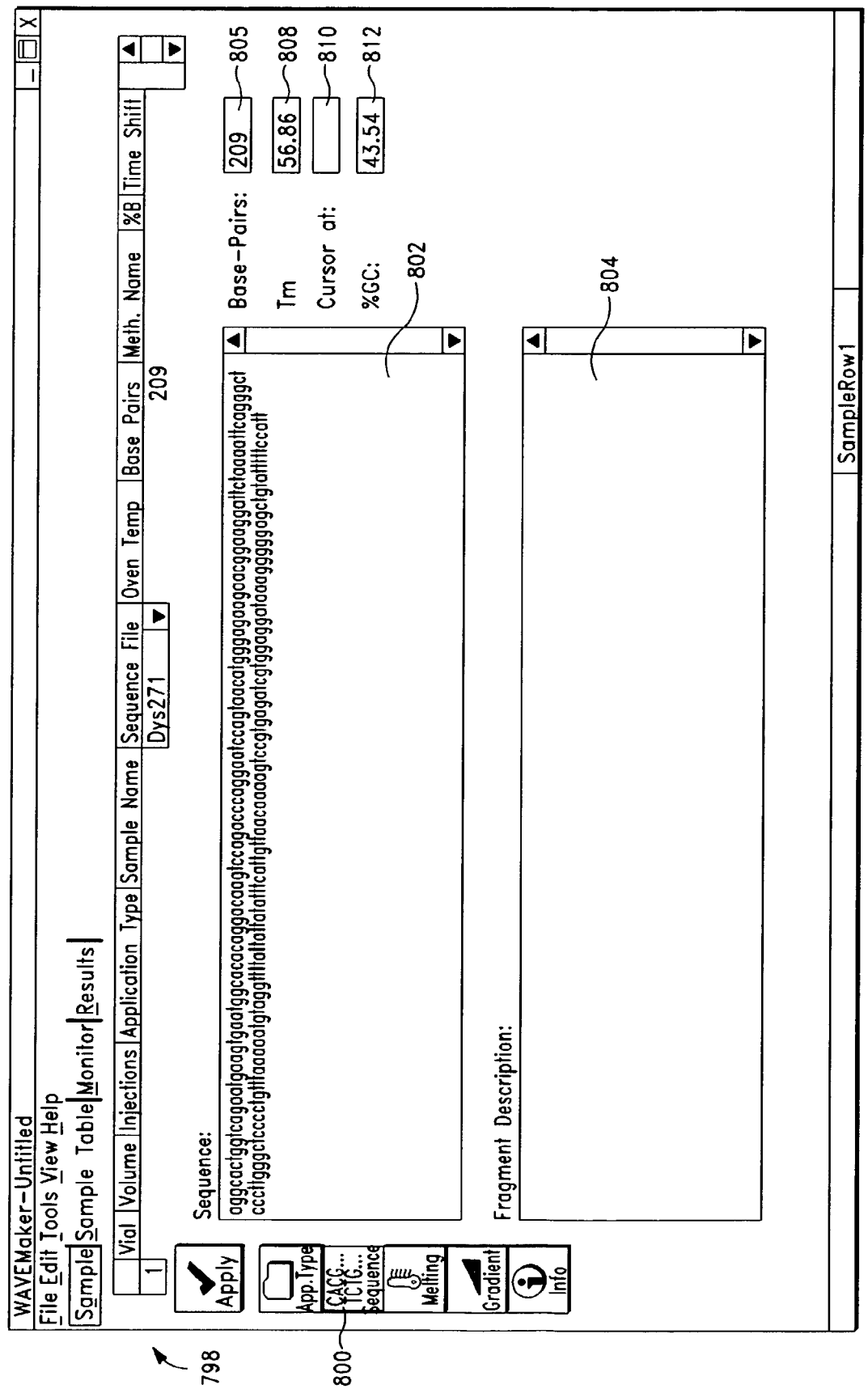
FIG. 49 is an embodiment of a software interface screen for use in mutation detection and illustrates the entry of an exemplary DNA sequence (SEQ ID NO: 1).

The preferred software of the instant invention provides novel graphical user interface screens to facilitate data entry and evaluation for mutation detection by DMIPC. Illustrating one embodiment of such an interface, FIG. 49 shows a DNA Sequence Screen 798 which is accessible by click button 800. Field 802 provides a field for entering the DNA sequence from the keyboard, clipboard, or ASCII text file. A Fragment Description field 804 provides a field for entering a description of the fragment. The number of base pairs is automatically calculated, displayed in field 806, and also entered in an associated Gradient Template for the sample. T(hsst), predicted preferably by Equation (v) described herein, is displayed at 808. The current cursor position is shown at 810. The % GC of the sequence is displayed at 812.

Figure 50:
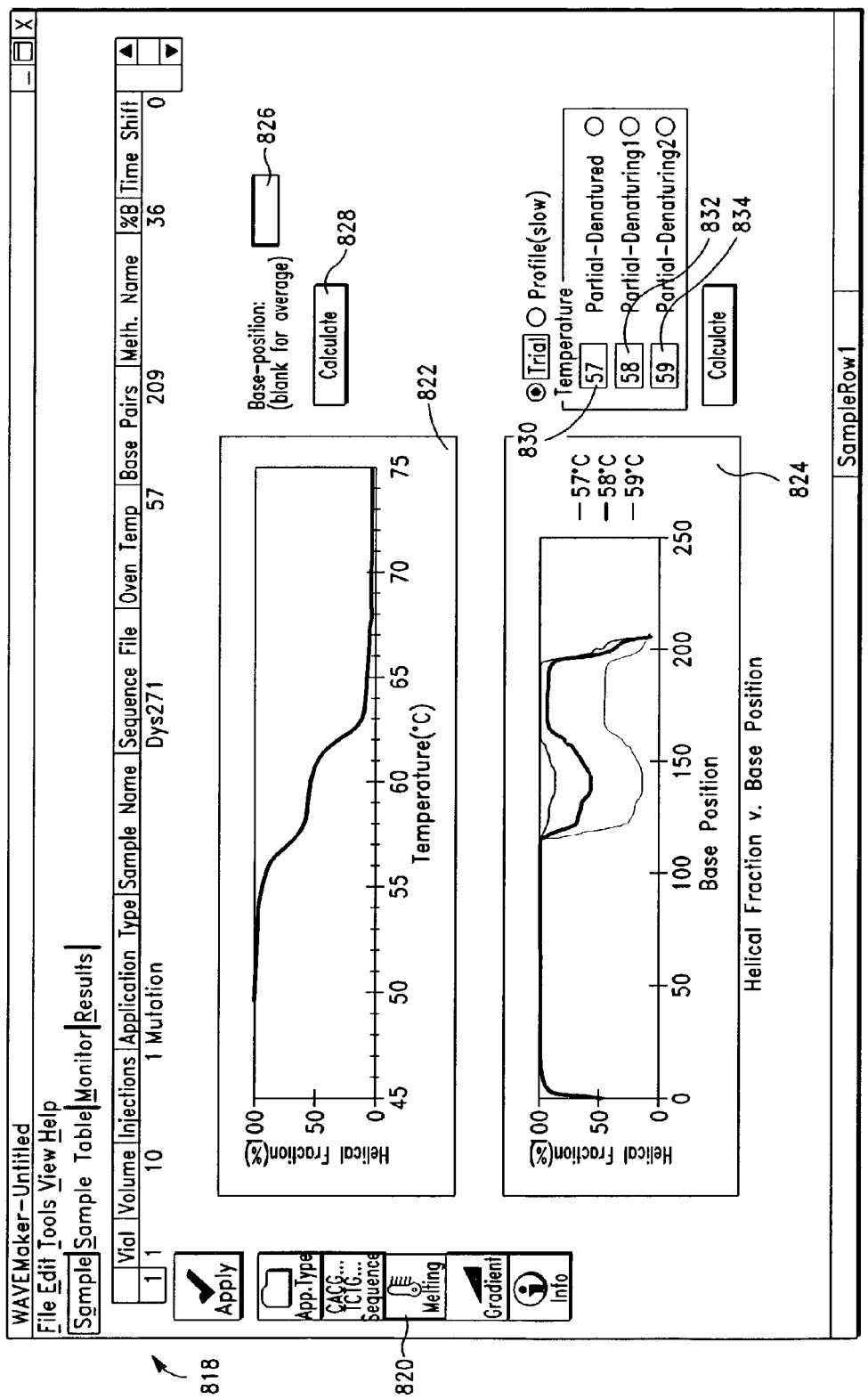
FIG. 50 is second embodiment of a software interface screen for use in mutation detection.

FIG. 50 illustrates a Melting Profiles Screen 818 which is accessible by click button 820. This screen includes fields 822 and 824 which display the melting behavior, as predicted by an equation such as Equation (v) described hereinabove, of the duplex fragment entered in the DNA Sequence field 802.

Field 822 shows Helical Fraction vs. Temperature. The percent helicity at a particular base may be displayed by entering the location of the base in the field 826. If the filed is left blank, the average percent helicity is displayed. In either case, the plot is updated by pressing the Calculate button 828. All of the user interfaces described herein incorporate the usual options for editing, pasting, and copying into other computer applications.

Figure 51:
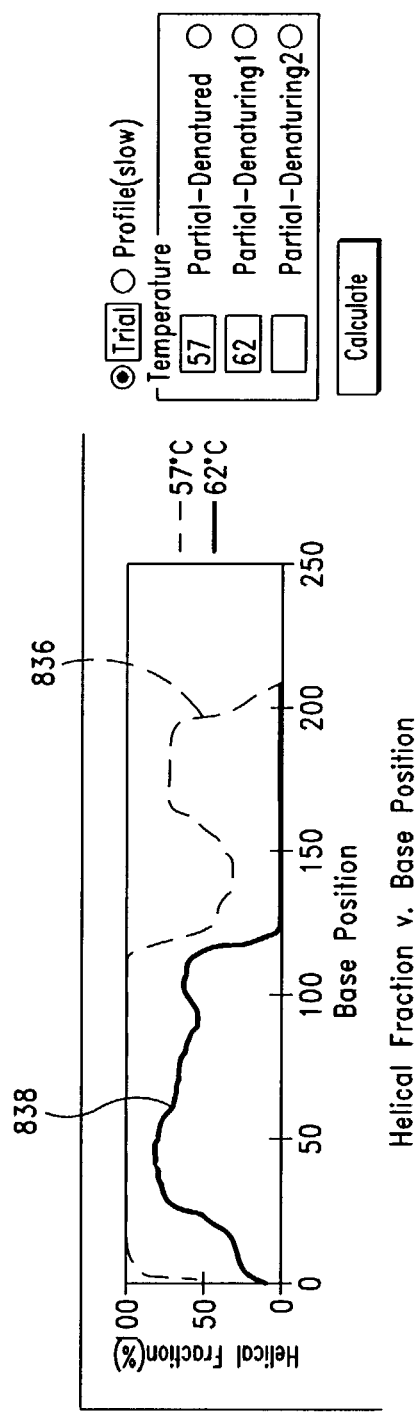
FIG. 51 is an example of a field from the interface screen of FIG. 50.

Field 824 shows the pattern of denaturation along the fragment at the temperatures entered in the fields 830, 832, 834. A plurality of traces (e.g., three as shown) can be displayed at different temperatures distinguished by different colors. FIG. 51 illustrates the use of the graph in field 824 to determine the temperatures needed to detect mutations in different regions of the fragment. The dashed trace 836 indicates that mutations located in the region from approximately 120 to 209 bp would be found with the oven temperature at 57° C., while the solid trace 838 indicates mutations in the region 1-120 bp would require an oven temperature of 62° C. The first temperature is automatically determined by the software using an equation such as Equation (v). The second temperature can be determined by entering test temperatures in the boxes and calculating the melting curves. A preferred temperature will display the region of interest between about 30 to 80 percent Helical Fraction.

Figure 52:
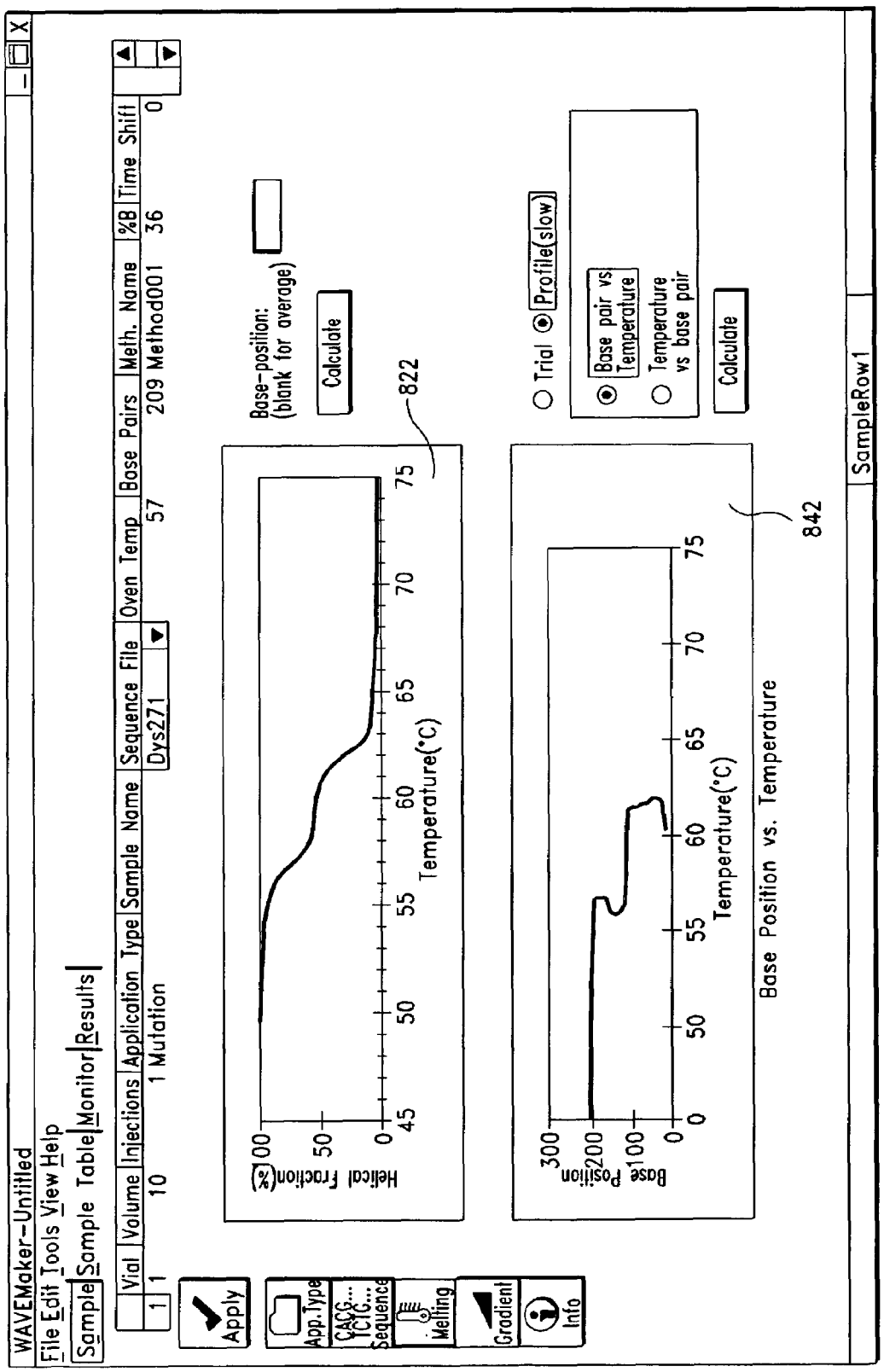
FIG. 52 is a third embodiment of a software interface screen for use in mutation detection.

FIG. 52 illustrates another embodiment of a Melting Profiles Screen at 840. Temperature corresponding to 75% helical is plotted against fragment size (base pair) in field 842. This plot can be rotated by 90 degrees so that the temperature scale matches that of the plot 822.

In its most general form, the separation process used in the chromatography system of the invention concerns separation of polynucleotides, e.g. DNA, utilizing a stationary separation medium having non-polar surfaces. The preferred surfaces are essentially free from multivalent cation contamination which can trap polynucleotides. The separation is performed on the stationary surface. The surface can be porous, but preferably any surface pores are of a size which excludes the smallest polynucleotide being analyzed.

In one embodiment, the non-polar surfaces comprise the surfaces of polymeric beads. In an alternative embodiment, the surfaces comprise the surfaces of interstitial spaces in a molded polymeric monolith. For purposes of simplifying the description of the invention and not by way of limitation, the separation of polynucleotides using nonporous beads, and the preparation of such beads, will be primarily described herein, it being understood that other separation surfaces, such as the interstitial surfaces of polymeric monoliths, are intended to be included within the scope of this invention. Monoliths such as rods contain polymer separation media which have been formed inside a column as a unitary structure having through pores or interstitial spaces which allow eluting solvent and analyte to pass through and which provide the non-polar separation surface.

In general, the only requirement for the separation media of the present invention is that they must have a surface that is either intrinsically non-polar or be bonded with a material that forms a surface having sufficient non-polarity to interact with a counterion agent.

The non-porous polymeric beads can have an average diameter of about 0.5-100 microns; preferably, 1-10 microns; more preferably, 1-5 microns. Beads having an average diameter of 1.0-3.0 microns are most preferred.

In U.S. Pat. No. 5,585,236, Bonn et al. had characterized the nucleic acid separation process as reverse phase ion pairing chromatography (RPIPC). However, since RPIPC does not incorporate certain essential characteristics described in the present invention, another term, Matched Ion Polynucleotide Chromatography (MIPC), has been selected. MIPC as used herein, is defined as a process for separating single and double stranded polynucleotides using non-polar beads, wherein the process uses a counterion agent, and an organic solvent to elute the nucleic acid from the beads, and wherein the beads are characterized as having a DNA Separation Factor of at least 0.05. In a preferred embodiment, the beads have a DNA Separation Factor of at least 0.5. In an optimal embodiment, the beads have a DNA Separation Factor of at least 0.95.

Figure 53:
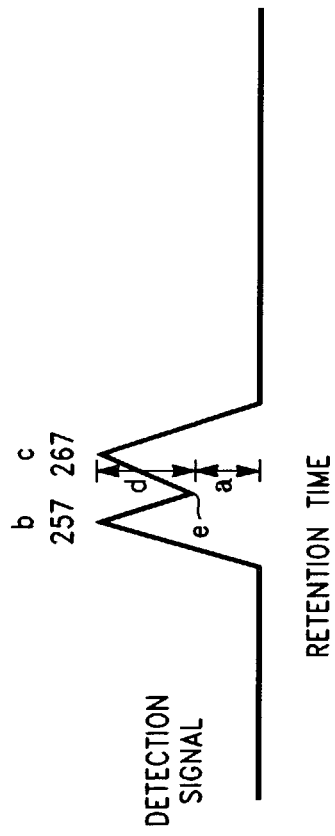
FIG. 53 is a schematic representation of the determination of the DNA Separation Factor.

The beads in the present invention provide high efficiency separation by MIPC of double stranded and single stranded DNA. A useful criterion for measuring performance of the beads is a DNA Separation Factor described in detail in copending application Ser. No. 09/183,123 (now U.S. Pat. No. 6,066,258). This is measured as the resolution of 257- and 267-base pair double stranded DNA fragments of a pUC18 DNA-HaeIII restriction digest and is defined as the ratio of the distance from the valley between the peaks to the top of the peaks, over the distance from the baseline to the top of the peaks. Referring to the schematic representation of FIG. 53, the DNA Separation Factor is determined by measuring the distance "a" from the baseline to the valley "e" between the peaks "b" and "c" and the distance "d" from the valley "e" to the top of one of the peaks "b" or "c". If the peak heights are unequal, the highest peak is used to obtain "d." The DNA Separation Factor is the ratio of d/(a+d). The peaks of 257- and 267-base pairs in this schematic representation are similar in height. Operational beads of the present invention have a DNA Separation Factor of at least 0.05. Preferred beads have a DNA Separation Factor of at least 0.5.

Without wishing to be bound by theory, Applicants believe that the beads which conform to the DNA Separation Factor as specified herein have a pore size which essentially excludes the polynucleotides being separated from entering the bead. As used herein, the term "nonporous" is defined to denote a bead which has surface pores having a diameter that is less than the size and shape of the smallest DNA fragment in the separation in the solvent medium used therein. Included in this definition are polymer beads having these specified maximum size restrictions in their natural state or which have been treated to reduce their pore size to meet the maximum effective pore size required. Preferably, all beads which provide a DNA Separation Factor of at least 0.5 are intended to be included within the definition of "nonporous" beads.

The surface conformations of nonporous beads of the present invention can include depressions and shallow pit-like structures which do not interfere with the separation process. A pretreatment of a porous bead to render it nonporous can be effected with any material which will fill the pores in the bead structure and which does not significantly interfere with the MIPC process.

Pores are open structures through which mobile phase and other materials can enter the bead structure. Pores are often interconnected so that fluid entering one pore can exit from another pore. Applicants believe that pores having dimensions that allow movement of the polynucleotide into the interconnected pore structure and into the bead impair the resolution of separations or result in separations that have very long retention times. In MIPC, however, the beads are "nonporous" and the polynucleotides do not enter the bead structure.

Chromatographic efficiency of the column beads is predominantly influenced by the properties of surface and near-surface areas. For this reason, the following descriptions are related specifically to the close-to-the-surface region of the polymeric beads. The main body and/or the center of such beads can exhibit entirely different chemistries and sets of physical properties from those observed at or near the surface of the polymeric beads of the present invention.

In another embodiment of the present invention, the separation medium can be in the form of a polymeric monolith such as a rod-like monolithic column. The monolithic column is polymerized or formed as a single unit inside of a tube as described in the Examples hereinbelow. The through pore or interstitial spaces provide for the passage of eluting solvent and analyte materials. The separation is performed on the stationary surface. The surface can be porous, but is preferably nonporous. The form and function of the separations are identical to columns packed with beads. As with beads, the pores contained in the rod must be compatible with DNA and not trap the material. Also, the rod must not contain contamination that will trap DNA.

The molded polymeric rod of the present invention is prepared by bulk free radical polymerization within the confines of a chromatographic column. The base polymer of the rod can be produced from a variety of polymerizable monomers. For example, the monolithic rod can be made from polymers, including mono- and di-vinyl substituted aromatic compounds such as styrene, substituted styrenes, alpha-substituted styrenes and divinylbenzene; acrylates and methacrylates; polyolefins such as polypropylene and polyethylene; polyesters; polyurethanes; polyamides; polycarbonates; and substituted polymers including fluorosubstituted ethylenes commonly known under the trademark TEFLON.

The base polymer can also be mixtures of polymers, non-limiting examples of which include poly(glycidyl methacrylate-co-ethylene dimethacrylate), poly(styrene-divinylbenzene) and poly(ethylvinylbenzene-divinylbenzene). The rod can be unsubsituted or substituted with a substituent such as a hydrocarbon alkyl or an aryl group. The alkyl group optionally has 1 to 1,000,000 carbons inclusive in a straight or branched chain, and includes straight chained, branch chained, cyclic, saturated, unsaturated nonionic functional groups of various types including aldehyde, ketone, ester, ether, alkyl groups, and the like, and the aryl groups includes as monocyclic, bicyclic, and tricyclic aromatic hydrocarbon groups including phenyl, naphthyl, and the like.

In a preferred embodiment, the alkyl group has 1-24 carbons. In a more preferred embodiment, the alkyl group has 1-8 carbons. The substitution can also contain hydroxy, cyano, nitro groups, or the like which are considered to be non-polar, reverse phase functional groups. Methods for hydrocarbon substitution are conventional and well-known in the art and are not an aspect of this invention. The preparation of polymeric monoliths is by conventional methods well known in the art as described in the following references: Wang et al. (*J. Chromatog. A* 699:230 (1994)), Petro et al. (*Ana. Chem.* 68:315 (1996)), and the following U.S. Pat. Nos. 5,334,310; 5,453,185; 5,522,994 (to Frechet). Monolith or rod columns are commercially available from Merck & Co (Darmstadt, Germany).

The nonporous polymeric beads of the present invention are prepared by a two-step process in which small seed beads are initially produced by emulsion polymerization of suitable-polymerizable monomers. The emulsion polymerization procedure of the invention is a modification of the procedure of Goodwin, et al. (*Colloid & Polymer Sci.*, 252:464-471 (1974)). Monomers which can be used in the emulsion polymerization process to produce the seed beads include styrene, alkyl substituted styrenes, alpha-methyl styrene, and alkyl substituted alpha-methyl styrene. The seed beads are then enlarged and, optionally, modified by substitution with various groups to produce the nonporous polymeric beads of the present invention.

The seed beads produced by emulsion polymerization can be enlarged by any known process for increasing the size of the polymer beads. For example, polymer beads can be enlarged by the activated swelling process disclosed in U.S. Pat. No. 4,563,510. The enlarged or swollen polymer beads are further swollen with a crosslinking polymerizable monomer and a polymerization initiator. Polymerization increases the crosslinking density of the enlarged polymeric bead and reduces the surface porosity of the bead. Suitable crosslinking monomers contain at least two carbon-carbon double bonds capable of polymerization in the presence of an initiator. Preferred crosslinking monomers are divinyl monomers, preferably alkyl and aryl (phenyl, naphthyl, etc.) divinyl monomers and include divinyl benzene, butadiene, etc. Activated swelling of the polymeric seed beads is useful to produce polymer beads having an average diameter ranging from 1 up to about 100 microns.

Alternatively, the polymer seed beads can be enlarged simply by heating the seed latex resulting from emulsion polymerization. This alternative eliminates the need for activated swelling of the seed beads with an activating solvent. Instead, the seed latex is mixed with the crosslinking monomer and polymerization initiator described above, together with or without a water-miscible solvent for the crosslinking monomer. Suitable solvents include acetone, tetrahydrofuran (THF), methanol, and dioxane. The resulting mixture is heated for about 1-12 hours, preferably about 4-8 hours, at a temperature below the initiation temperature of the polymerization initiator, generally, about 10° C.-80° C., preferably 30° C.-60° C.

Optionally, the temperature of the mixture can be increased by 10-20% and the mixture heated for an additional 1 to 4 hours. The ratio of monomer to polymerization initiator is at least 100:1, preferably about 100:1 to about 500:1, more preferably about 200:1 in order to ensure a degree of polymerization of at least 200. Beads having this degree of polymerization are sufficiently pressure-stable to be used in high pressure liquid chromatography (HPLC) applications. This thermal swelling process allows one to increase the size of the bead by about 110-160% to obtain polymer beads having an average diameter up to about 5 microns, preferably about 2-3 microns. The thermal swelling procedure can, therefore, be used to produce smaller particle sizes previously accessible only by the activated swelling procedure.

Following thermal enlargement, excess crosslinking monomer is removed and the particles are polymerized by exposure to ultraviolet light or heat. Polymerization can be conducted, for example, by heating of the enlarged particles to the activation temperature of the polymerization initiator and continuing polymerization until the desired degree of polymerization has been achieved. Continued heating and polymerization allows one to obtain beads having a degree of polymerization greater than 500.

In the present invention, the packing material disclosed by Bonn et al. or U.S. Pat. No. 4,563,510 can be modified through substitution of the polymeric beads with alkyl groups or can be used in its unmodified state. For example, the polymer beads can be alkylated with 1 or 2 carbon atoms by contacting the beads with an alkylating agent, such as methyl iodide or ethyl iodide. Alkylation is achieved by mixing the polymer beads with the alkyl halide in the presence of a Friedel-Crafts catalyst to effect electrophilic aromatic substitution on the aromatic rings at the surface of the polymer blend. Suitable Friedel-Crafts catalysts are well-known in the art and include Lewis acids such as aluminum chloride, boron trifluoride, tin tetrachloride, etc. The beads can be hydrocarbon substituted by substituting the corresponding hydrocarbon halide for methyl iodide in the above procedure, for example.

The term alkyl as used herein in reference to the beads of the present invention is defined to include alkyl and alkyl substituted aryl groups, having from 1 to 1,000,000 carbons, the alkyl groups including straight chained, branch chained, cyclic, saturated, unsaturated nonionic functional groups of various types including aldehyde, ketone, ester, ether, alkyl groups, and the like, and the aryl groups including as monocyclic, bicyclic, and tricyclic aromatic hydrocarbon groups including phenyl, naphthyl, and the like. Methods for alkyl substitution are conventional and well-known in the art and are not an aspect of this invention. The substitution can also contain hydroxy, cyano, nitro groups, or the like which are considered to be non-polar, reverse phase functional groups.

The chromatographic material reported in the Bonn patent was limited to nonporous beads substituted with alkyl groups having at least 3 carbons because Bonn et al. were unsuccessful in obtaining separations using polymer beads lacking this substitution. Additionally, the polymer beads were limited to a small group of vinyl aromatic monomers, and Bonn et al. were unable to effect double stranded DNA separations with other materials.

In the present invention, successful separation of double stranded DNA can be achieved using underivatized nonporous beads as well as using beads derivatized with alkyl groups having 1 to 1,000,000 carbons.

The base polymer of the invention can also be other polymers, non-limiting examples of which include mono- and di-vinyl substituted aromatics such as styrene, substituted styrenes, alpha-substituted styrenes and divinylbenzene; acrylates and methacrylates; polyolefins such as polypropylene and polyethylene; polyesters; polyurethanes; polyamides; polycarbonates; and substituted polymers including fluorosubstituted ethylenes commonly known under the trademark TEFLON. The base polymer can also be mixtures of polymers, non-limiting examples of which include poly(styrene-divinylbenzene) and poly(ethylvinyl-benzene-divinylbenzene). Methods for making beads from these polymers are conventional and well known in the art (for example, see U.S. Pat. No. 4,906,378). The physical properties of the surface and near-surface areas of the beads are the predominant influence on chromatographic efficiency. The polymer, whether derivatized or not, must provide a nonporous, non-reactive, and non-polar surface for the MIPC separation.

The description of the separation process of this invention is presented in relationship to polymeric beads with non-polar surfaces described above, not by way of limitation but to simplify the presentation. It should be understood that the separation surfaces can also be provided by monolithic polymeric materials described above or they can be provided by the inorganic polymers with non-polar surfaces described hereinbelow, and processes and systems including all of these materials are intended to be included within the scope of this invention.

The beads of the invention comprise a nonporous particle which has non-polar molecules or a non-polar polymer attached to or coated on its surface such as the materials described in copending application Ser. No. 09/183,450, the entire contents of which are hereby incorporated by reference. In general, the beads comprise nonporous particles which have been coated with a polymer or which have substantially all surface substrate groups reacted with a non-polar hydrocarbon or substituted hydrocarbon group, and any remaining surface substrate groups endcapped with a tri(lower alkyl)chlorosilane or tetra(lower alkyl)dichloro-disilazane as described above.

The nonporous particle is preferably an inorganic particle, but can be a nonporous organic particle. The nonporous particle can be, for example, silica, silica carbide, silica nitrite, titanium oxide, aluminum oxide, zirconium oxide, carbon, insoluble polysaccharides such as cellulose, or diatomaceous earth, or any of these materials which have been modified to be nonporous. Examples of carbon particles include diamond and graphite which have been treated to remove any interfering contaminants. The preferred particles are essentially non-deformable and can withstand high pressures. The nonporous particle is prepared by known procedures. The preferred particle size is about 0.5-100 microns; preferably, 1-10 microns; more preferably, 1-5 microns. Beads having an average diameter of 1.0-3.0 microns are most preferred.

Because the chemistry of preparing conventional silica-based reverse phase HPLC materials is well-known, most of the description of the beads of the invention herein is presented in reference to silica. It is to be understood, however, that other nonporous particles, such as those listed above, can be modified in the same manner and substituted for silica in the process of the invention. For a description of the general chemistry of silica, see Colin F. Poole, and Salwa K. Poole, *Chromatography Today*, Elsevier: New York (1991), pp. 313-342 and Snyder, R. L. and J. J. Kirkland, *Introduction to Modern Liquid Chromatography*, $2^{nd}$ ed., John Wiley & Sons, Inc.: New York (1979), pp. 272-278, the disclosures of which are hereby incorporated herein by reference in their entireties.

The nonporous beads of the invention are characterized by having minimum exposed silanol groups after reaction with the coating or silating reagents. Minimum silanol groups are needed to reduce the interaction of the DNA with the substrate and also to improve the stability of the material in a high pH and aqueous environment. Silanol groups can be harmful because they can repel the negative charge of the DNA molecule, preventing or limiting the interaction of the DNA with the stationary phase of the column.

Another possible mechanism of interaction is that the silanol can act as ion exchange sites, taking up metals such as iron (III) or chromium (III). Iron (III) or other metals which are trapped on the column can distort the DNA peaks or even prevent DNA from being eluted from the column.

Silanol groups can be hydrolyzed by the aqueous-based mobile phase. Hydrolysis will increase the polarity and reactivity of the stationary phase by exposing more silanol sites, or by exposing metals that can be present in the silica core. Hydrolysis will be more prevalent with increased underivatized silanol groups. The effect of silanol groups on the DNA separation depends on which mechanism of interference is most prevalent. For example, iron (III) can become attached to the exposed silanol sites, depending on whether the iron (III) is present in the mobile phase, instrument or sample.

The effect of metals can only occur if metals are already present within the system or reagents. Metals present within the system or reagents can get trapped by ion exchange sites on the silica. However, if no metals are present within the system or reagents, then the silanol groups themselves can cause interference with DNA separations. Hydrolysis of the exposed silanol sites by the aqueous environment can expose metals that might be present in the silica core.

Fully hydrolyzed silica contains a concentration of about 8 μmoles of silanol groups per square meter of surface. At best, because of steric considerations, a maximum of about 4.5 μmoles of silanol groups per square meter can be reacted, the remainder of the silanol being sterically shielded by the reacted groups. Minimum silanol groups is defined as reaching the theoretical limit of or having sufficient shield to prevent silanol groups from interfering with the separation.

Numerous methods exist for forming nonporous silica core particles. For example, sodium silicate solution poured into methanol will produce a suspension of finely divided spherical particles of sodium silicate. These particles are neutralized by reaction with acid. In this way, globular particles of silica gel are obtained having a diameter of about 1-2 microns. Silica can be precipitated from organic liquids or from a vapor. At high temperature (about 2000° C.), silica is vaporized, and the vapors can be condensed to form finely divided silica either by a reduction in temperature or by using an oxidizing gas. The synthesis and properties of silica are described by R. K. ller in *The Chemistry of Silica, Solubility, Polymerization, Colloid and Surface Properties, and Biochemistry*, John Wiley & Sons: New York (1979).

W. Stöber et al. described controlled growth of monodisperse silica spheres in the micron size range in *J. Colloid and Interface Sci.*, 26:62-69 (1968). Stöber et al. describe a system of chemical reactions which permit the controlled growth of spherical silica particles of uniform size by means of hydrolysis of alkyl silicates and subsequent condensation of silicic acid in alcoholic solutions. Ammonia is used as a morphological catalyst. Particle sizes obtained in suspension range from less than 0.05 μm to 2 μm in diameter.

Nonporous silica core beads can be obtained from Micra Scientific (Northbrook, Ill.) and from Chemie Uetikkon (Lausanne, Switzerland).

To prepare the nonporous beads of the invention, the nonporous particle is coated with a polymer or reacted and endcapped so that substantially all surface substrate groups of the nonporous particle are blocked with a non-polar hydrocarbon or substituted hydrocarbon group. This can be accomplished by several methods.

Figure 54:
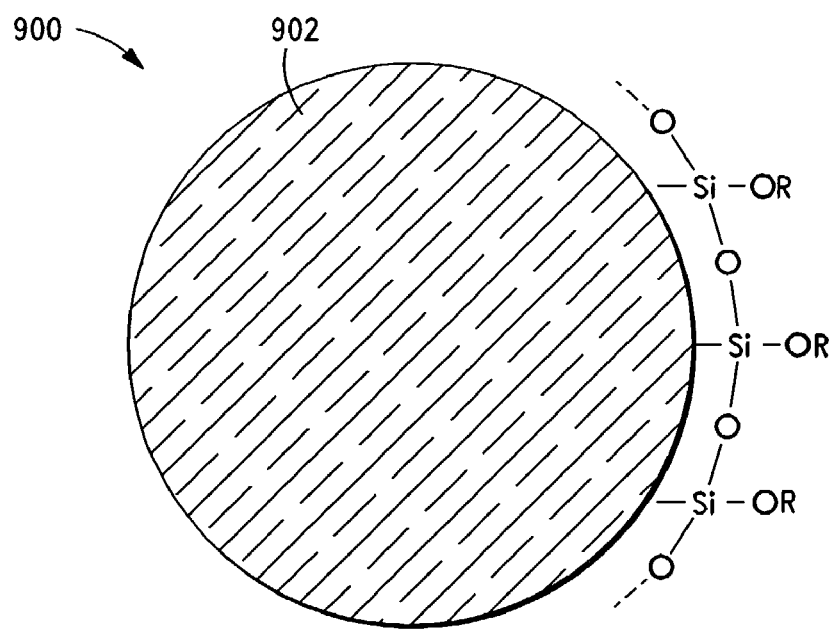
FIG. 54 is a schematic drawing of a cross-section of a representation of a reverse phase bead with a silica core and endcapping shielding.

The organic bonded-phase siloxane coating can be made as a monomolecular layer or as a polymerized multilayer coating. Packings with so-called monomolecular organic layers are normally prepared by reacting the surface silanol groups of siliceous-base particles with mono-, di-, or trifunctional chloro-, dimethyl-, amino-, siloxy-, or alkoxy-silanes. Typical monofunctional reactants used in these reactions include X—Si—R, where X=Cl, OH, $OCH_3$, or $OC_2H_5$, and R is an organic radical. FIG. 54 is a schematic representation of a bead 900 having a silica core 902 and a monomolecular organic layer. (The figure does not necessarily reflect the morphology or pore structure of the beads of the invention and is meant for illustrative purposes only.)

Using bi- and trifunctional reactants, such as $R_2SiX_2$ and $RSiX_3$, for the surface modifications, up to two Si—X groups per bonded functional group remain unreacted. After treatment with water, hydrolysis of these unreacted groups takes place, and additional silanol groups are formed (sometimes in a polymer matrix) in about the same concentration as the bonded organic functional groups present in the packing. These acidic organo-silanol groups can significantly affect the retention behavior of solutes and adversely influence the stability of the packing in aqueous solutions at pH>7.

Thus, incomplete reaction of the surface with the silane reagent, or the formation of new Si—OH groups from using bi- or trifunctional modifiers, can result in a population of residual acidic Si—OH groups that are readily accessible to molecules of the mobile phase or sample. Therefore, the recent trend is toward (a) a dense monolayer of functional groups instead of partial coverage and (b) the use of monofunctional dimethylsilanes [X—Si$(CH_3)_2$—R] to provide a homogeneous organic coating with a minimum possibility of residual Si—OH groups. Monochlorosilane reagents are preferred, if the required organic functionality can be prepared. If two of the R groups in the monofunctional modifier are methyl, surface coverage can be as high as about 4 μmoles per square meter of organic (based on carbon analysis). In the latter case, residual Si—OH groups on the silica surface are unavailable for chromatographic interactions with most solutes because of steric shielding.

The reaction of organosilanols (e.g., HO—Si—$R_3$) or organoalkoxy-(e.g., RO—Si—$R_3$) silanes with silica supports without polymerization can also produce good packings. These reactions are relatively reproducible, provided that traces of water or other reactive species are absent. Unreacted, accessible silanols can be left after the initial reaction, but these can be removed by capping of the packing with chlorotrimethylsilane (providing the R groups do not react with the latter silane).

According to one method, the nonporous particle is coated with a polymer coating. Suitable polymers for use in coating the particle include chain reaction polymers and step reaction polymers, for example, polystyrene, polymethacrylate, polyethylene, polyurethane, polypropylene, polyamide, insoluble polysaccharides such as cellulose, polydimethyl siloxane, polydialkyl siloxane, and related materials. The polymer coating can be attached to the nonporous particle by means of a multi-coating process so that complete shielding of the surface is achieved.

Figure 55:
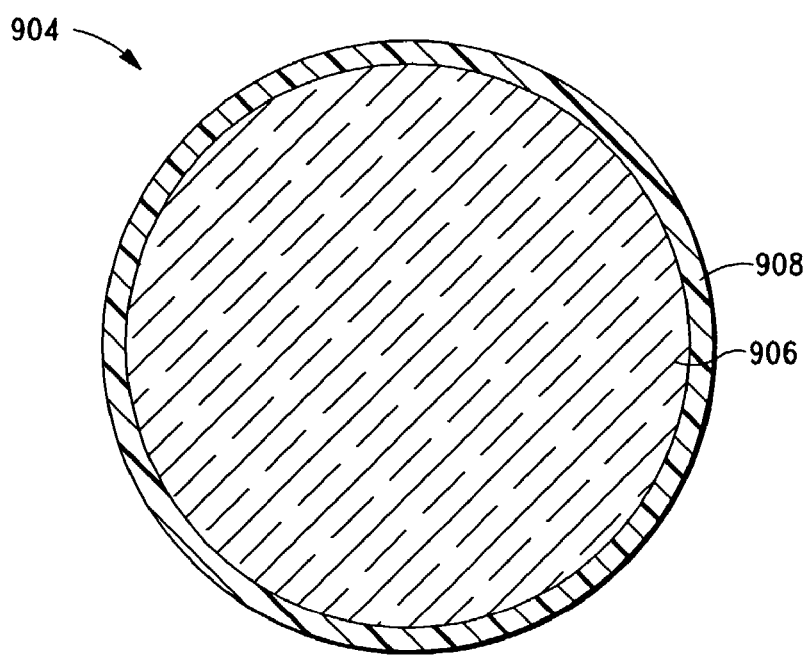
FIG. 55 is a schematic drawing of a cross-section of a representation of a reverse phase bead with a silica core and polymer shielding.

In the last few years, new bonded phase packings, known as polymer-coated or polymer-encapsulated packings, have been introduced based on techniques used to prepare immobilized stationary phases for open tubular column gas chromatography. In this case, the phases are prepared by mechanically coating either bare silica or presilanized silica microparticles with a poly(siloxane) or poly(butadiene) prepolymer, which is then immobilized by peroxide, azo-tert-butane, or gamma radiation-induced chemical crosslinking reactions. FIG. 55 is a schematic illustration of a coated bead 904 having a silica core 906 and polymer coating 908. (The figure does not necessarily reflect the morphology or pore structure of the beads of the invention and is meant for illustrative purposes only.)

An alternative method comprises a combination of covalent bonding with a vinyl-containing silane molecule and then polymerizing a coating on the surface of the particles. A second coating can be applied if residual silanol groups or metal groups are present.

In a variation of this method, the silica surface is first modified by reaction with vinyltrichlorosilane, followed by polymerizing acrylic acid derivatives to and over the derivatized silica surface. The availability of a large number of useful monomers and prepolymers has enabled a wide variety of reverse phase, polar, and ion exchange packings to be prepared using the same general reaction. Also, since the general approach does not depend on the chemistry of the underlying substrate, materials other than silica, for example, alumina and zirconia, can be modified and used under conditions for which silica is unsuitable, for example, with mobile phases outside the pH range 2-7.5. Returning to silica, presilanization decreases the number of active silanol groups, which are then further shielded by the polymeric film anchored over the surface. In reverse phase liquid chromatography, these packings have shown improved chromatographic properties compared to monomeric, chemically bonded phases for the separation of basic solutes. Polymer-encapsulated packings have a film thickness of about 1 nm to maintain reasonable mass transfer characteristics. A description of this procedure has been published by H. Engelhart et al. (*Chromatographia*, 27:535 (1989)).

The polymer-coated beads prepared according to either of the above methods can be used in their unmodified state or can be modified by substitution with a hydrocarbon group. Any hydrocarbon group is suitable. The term "hydrocarbon" as used herein is defined to include alkyl and alkyl substituted aryl groups, having from 1 to 1,000,000 carbons, the alkyl groups including straight chained, branch chained, cyclic, saturated, unsaturated nonionic functional groups of various types including, aldehyde, ketone, ester, ether, alkyl groups, and the like, and the aryl groups including as monocyclic, bicyclic, and tricyclic aromatic hydrocarbon groups including phenyl, naphthyl, and the like. Methods for hydrocarbon substitution are conventional and well-known in the art and are not an aspect of this invention. The hydrocarbon can also contain hydroxy, cyano, nitro groups, or the like which are considered to be non-polar, reverse phase functional groups. The preferred hydrocarbon groups are alkyl groups, and the description of suitable substitution processes hereinbelow are presented as alkylation for purposes of simplification and not by way of limitation, it being understood that aryl substitution by conventional procedures are also intended to be included within the scope of this invention.

The polymer-coated beads can be alkylated by reaction with the corresponding alkyl halide such as the alkyl iodide. Alkylation is achieved by mixing the polymer-coated beads with an alkyl halide in the presence of a Friedel-Crafts catalyst to effect electrophilic aromatic substitution on the aromatic rings at the surface of the polymer blend. Suitable Friedel-Crafts catalysts are well-known in the art and include Lewis acids such as aluminum chloride, boron trifluoride, tin tetrachloride, etc. Substitution with hydrocarbon groups having from 1 to 1,000,000 and preferably from 1 to 22 carbons can be effected by these processes. Hydrocarbon groups having from 23 to 1,000,000 carbons are referenced herein as hydrocarbon polymers.

Alkylation can be accomplished by a number of known synthesis procedures. These include Friedel-Crafts alkylation with an alkyl halide, attachment of an alkyl alcohol to a chloromethylated bead to form an ether, etc. Although the preferred method for alkylating the polymer-coated beads of the present invention is alkylation after the polymer coating has been formed on the nonporous particle, an alternative method of alkylation is to polymerize alkylated monomers to form an alkylated polymer coating on the nonporous particle. In this embodiment, the monomers will be substituted with alkyl groups having any number of carbon atoms, for example, from 1 to 100, 1 to 50 or 1 to 24, for example, depending upon the requirements of the separation variables.

As an alternative to polymer coating, the nonporous particle can be functionalized with an alkyl group or other non-polar functional group including cyano, ester, and other non-ionic groups, followed by a complete endcapping process to reduce silanol and metal interaction. Endcapping of the nonporous particle can be achieved by reacting the particle with trialkyl chlorosilane or tetraalkyl dichlorodisilazane, such as, for example, trimethyl chlorosilane or dichloro-tetraisopropyl-disilazane.

A large number of factors influence the success of the bonding reactions and the quality of the final bonded-phase product. The rate and extent of the bonding reaction depends on the reactivity of the silane, choice of solvent and catalyst, time, temperature, and the ratio of reagents to substrate. Reactive organosilanes with Cl, OH, OR, $N(CH_3)_2$, $OCOCF_3$, and enolates as leaving groups have been widely used. The dimethylamine, trifluoroacetate, and enol ethers of pentane-2,4-dione are the most reactive leaving groups, although economy, availability, and familiarity result in the chlorosilanes and alkoxysilanes being the most widely used, particularly among commercial manufacturers.

Initially, reactions can be almost stoichiometric but, as the surface coverage approaches a maximum value, the reaction becomes very slow. For this reason, reaction times tend to be long (12-72 hours), reaction temperatures moderately high (in most cases, around 100° C.) and, in the case of chlorosilanes, an acid acceptor catalyst (e.g., pyridine) is used. Some reagents, such as the alkylsilyl enolates and alkylsilyidimethylamines, do not require additional catalyst, or even solvent, to carry out the reaction. The most common solvents employed are toluene and xylene, although other solvents, such as carbon tetrachloride, trichloroethane, and dimethylformamide (DMF), have been recommended as being superior. Since the bonding reactions are carried out by refluxing in an inert atmosphere, solvents are often selected based on their capacity to be a good solvent for the organosilanes and to attain the desired reaction temperature at reflux.

Except for 3-cyanopropylsiloxane bonded phases, the high reactivity of chlorosilanes towards certain polar functional groups (e.g., OH, etc.) precludes the use of these groups for the preparation of polar, reverse phase bonded phases. Alkoxysilanes containing acidic or basic functional groups are autocatalytic and the bonded phases are usually prepared by refluxing the silane in an inert solvent at a temperature high enough to distill off the alcohol formed by the condensation reaction with the surface silanol groups. Bonding of neutral, polar ligands generally requires the addition of a catalyst, such as toluene-4-sulfonic acid or triethylamine, in the presence of sufficient water to generate monolayer coverage of the silica. The presence of water speeds up the hydrolysis of the alkoxy groups of the adsorbed organosilane, which tends to react with surface silanol groups rather than polymerize in solution.

It seems to be a general problem in the preparation of polar bonded phases that surface silanol groups are blocked by physically adsorbed organosilanes, giving rise to a lower bonded phase density after workup than the maximum theoretically predicted. The bonded phase density can be increased by repeating the reaction a second time or exposed silanol groups minimized by endcapping.

Although most bonded phases are prepared from organosilanes containing a single functionalized ligand bonded to silicon, with the remaining groups being leaving groups and/or methyl groups, more highly substituted organosilanes can also be used. Bifunctional organosilanes, such as 1,3-dichlorotetraisopropyldisilazane, are able to react with surface silanol groups at both ends of the chain, forming a bonded phase that is more hydrolytically stable than bonded phases formed from conventional organosilanes. The bidentate organosilanes have reactive sites that more closely match the spacing of the silanol groups on the silica surface and provide a higher bonded phase coverage than is achieved with dichlorosilanes with both leaving groups attached to the same silicon atom. For alkyldimethylsilanes, increasing the length of the alkyl group increases the hydrolytic stability of the bonded phase relative to that of the trimethylsilyl bonded ligands. Increasing the chain length of the methyl groups increases the hydrolytic stability of the bonded phase, but reduces the phase coverage due to steric effects. The use of monofunctional organosilanes containing one or two bulky groups, for example, isopropyl or t-butyl, on the silicon atom of the silane can become more important in the preparation of bonded phases for use at low pH. The bulky alkyl groups provide better steric protection to the hydrolytically sensitive siloxane groups on the packing surface than does the methyl group.

The general process of coating and endcapping of a silica substrate is well-known technology. However, the general understanding of those who have used these materials is they are not suitable for high performance double stranded DNA separations. However, the beads of this invention are formed by a more careful application of the coating and end-capping procedures to effect a thorough shielding of the silica core, the resulting beads having the ability to perform rapid separations of both single stranded and double stranded DNA which are equal to or better than those achieved using the alkylated nonporous polymer beads disclosed in U.S. Pat. No. 5,585,236, for example.

Care must be taken during the preparation of the beads to ensure that the surface of the beads has minimum silanol or metal oxide exposure and that the surface remains nonporous.

In an important aspect of the present invention, the beads and other media of the invention are characterized by having low amounts of metal contaminants or other contaminants that can bind DNA. The preferred beads of the present invention are characterized by having been subjected to precautions during production, including a decontamination treatment, such as an acid wash treatment, designed to substantially eliminate any multivalent cation contaminants (e.g. Fe(III), Cr(III), or colloidal metal contaminants). Only very pure, non-metal containing materials should be used in the production of the beads in order that the resulting beads will have minimum metal content.

In addition to the beads themselves being substantially metal-free, Applicants have also found that, to achieve optimum peak separation during MIPC, the separation column and all process solutions held within the column or flowing through the column are preferably substantially free of multivalent cation contaminants. As described in commonly owned U.S. Pat. Nos. 5,772,889; 5,997,742; and 5,972,222 and in co-pending U.S. patent applications Ser. No.09/080,547 (filed May 18, 1998) ( now U.S. Pat. No. 6,017,457) this can be achieved by supplying and feeding solutions that enter the separation column with components which have process solution-contacting surfaces made of material which does not release multivalent cations into the process solutions held within or flowing through the column, in order to protect the column from multivalent cation contamination. The process solution-contacting surfaces of the system components are preferably material selected from the group consisting of titanium, coated stainless steel, passivated stainless steel, and organic polymer.

There are two places where multivalent cation binding agents, e.g., chelators, are used in MIPC separations.

In one embodiment, these binding agents can be incorporated into a solid through which the mobile phase passes. Contaminants are trapped before they reach places within the system that can harm the separation. In these cases, the functional group is attached to a solid matrix or resin (e.g., a flow-through cartridge, usually an organic polymer, but sometimes silica or other material). The capacity of the matrix is preferably about 2 mequiv./g. An example of a suitable chelating resin is available under the trademark CHELEX 100 (Dow Chemical Co.) containing an iminodiacetate functional group.

In another embodiment, the multivalent cation binding agent can be added to the mobile phase. The binding functional group is incorporated into an organic chemical structure. The preferred multivalent cation binding agent fulfills three requirements. First, it is soluble in the mobile phase. Second, the complex with the metal is soluble in the mobile phase. Multivalent cation binding agents such as EDTA fulfill this requirement because both the chelator and the multivalent cation binding agent-metal complex contain charges which make them both water-soluble.

Also, neither precipitate when acetonitrile, for example, is added. The solubility in aqueous mobile phase can be enhanced by attaching covalently bound ionic functionality, such as, sulfate, carboxylate, or hydroxy. A preferred multivalent cation binding agent can be easily removed from the column by washing with water, organic solvent or mobile phase. Third, the binding agent must not interfere with the chromatographic process.

The multivalent cation binding agent can be a coordination compound. Examples of preferred coordination compounds include water soluble chelating agents and crown ethers. Non-limiting examples of multivalent cation binding agents which can be used in the present invention include acetylacetone, alizarin, aluminon, chloranilic acid, kojic acid, morin, rhodizonic acid, thionalide, thiourea, α-furildioxime, nioxime, salicylaldoxime, dimethylglyoxime, α-furildioxime, cupferron, α-nitroso-β-naphthol, nitroso-R-salt, diphenylthiocarbazone, diphenylcarbazone, eriochrome black T-, PAN, SPADNS, glyoxal-bis(2-hydroxyanil), murexide, α-benzoinoxime, mandelic acid, anthranilic acid, ethylenediamine, glycine, triaminotriethylamine, thionalide, triethylenetetramine, EDTA, metalphthalein, arsonic acids, α,α'-bipyridine, 4-hydroxybenzothiazole, 8-hydroxyquinaldine, 8-hydroxyquinoline, 1,10-phenanthroline, picolinic acid, quinaldic acid, α,α',α"-terpyridyl, 9-methyl-2,3,7-trihydroxy-6-fluorone, pyrocatechol, salicylic acid, tiron, 4-chloro-1,2-dimercaptobenzene, dithiol, mercaptobenzothiazole, rubeanic acid, oxalic acid, sodium diethyldithiocarbarbamate, and zinc dibenzyldithiocarbamate. These and other examples are described by Perrin in *Organic Complexing Reagents: Structure, Behavior, and Application to Inorganic Analysis*, Robert E. Krieger Publishing Co. (1964). In the present invention, a preferred multivalent cation binding agent is EDTA.

To achieve high resolution chromatographic separations of polynucleotides, it is generally necessary to tightly pack the chromatographic column with the solid phase polymer beads. Any known method of packing the column with a column packing material can be used in the present invention to obtain adequate high resolution separations. Typically, a slurry of the polymer beads is prepared using a solvent having a density equal to or less than the density of the polymer beads. The column is then filled with the polymer bead slurry and vibrated or agitated to improve the packing density of the polymer beads in the column. Mechanical vibration or sonication are typically used to improve packing density.

For example, to pack a 50×4.6 mm I.D. column, 2.0 grams of beads can be suspended in 10 mL of methanol with the aid of sonication. The suspension is then packed into the column using 50 mL of methanol at 8,000 psi of pressure. This improves the density of the packed bed.

The separation method of the invention is generally applicable to the chromatographic separation of single stranded and double stranded polynucleotides of DNA and RNA. Samples containing mixtures of polynucleotides can result from total synthesis of polynucleotides, cleavage of DNA or RNA with restriction endonucleases or with other enzymes or chemicals, as well as nucleic acid samples which have been multiplied and amplified using polymerase chain reaction techniques.

The method of the present invention can be used to separate double stranded polynucleotides having up to about 1500 to 2000 base pairs. In many cases, the method is used to separate polynucleotides having up to 600 bases or base pairs, or which have up to 5 to 80 bases or base pairs.

In a preferred embodiment, the separation is by Matched Ion Polynucleotide Chromatography (MIPC). The nonporous beads of the invention are used as a reverse phase material that will function with counterion agents and a solvent gradient to effect the DNA separations. In MIPC, the polynucleotides are paired with a counterion and then subjected to reverse phase chromatography using the nonporous beads of the present invention.

There are several types of counterions suitable for use with MIPC. These include a mono-, di-, or trialkylamine that can be protonated to form a positive counter charge or a quaternary alkyl substituted amine that already contains a positive counter charge. The alkyl substitutions may be uniform (for example, triethylammonium acetate or tetrapropylammonium acetate) or mixed (for example, propyldiethylammonium acetate). The size of the alkyl group may be small (methyl) or large (up to 30 carbons) especially if only one of the substituted alkyl groups is large and the others are small. For example octyidimethylammonium acetate is a suitable counterion agent. Preferred counterion agents are those containing alkyl groups from the ethyl, propyl or butyl size range.

The purpose of the alkyl group is to impart a nonpolar character to the polynucleic acid through a matched ion process so that the polynucleic acid can interact with the nonpolar surface of the separation media. The requirements for the extent of nonpolarity of the counterion-DNA pair depends on the polarity of the separation media, the solvent conditions required for separation, the particular size and type of fragment being separated. For example, if the polarity of the separation media is increased, then the polarity of the counterion agent may have to change to match the polarity of the surface and increase interaction of the counterion-DNA pair. Triethylammonium acetate is preferred although quaternary ammonium reagents such as tetrapropyl or tetrabutyl ammonium salts can be used when extra nonpolar character is needed or desired. In general, as the polarity of the alkyl group is increased, size specific separations, sequence independent separations become more possible. Quaternary counterion reagents are not volatile, making collection of fragments more difficult.

In some cases, it may be desired to increase the range of concentration of organic solvent used to perform the separation. For example, increasing the alkyl length on the counterion agent will increase the nonpolarity of the counterion-DNA pair resulting in the need to either increase the concentration of the mobile phase organic solvent, or increase the strength of the organic solvent type, e.g. acetonitrile is about two times more effective than methanol for eluting polynucleic acids. There is a positive correlation between concentration of the organic solvent required to elute a fragment from the column and the length of the fragment. However, at high organic solvent concentrations, the polynucleotide could precipitate. To avoid precipitation, a strong organic solvent or a smaller counterion alkyl group can be used. The alkyl group on the counterion reagent can also be substituted with halides, nitro groups, or the like to moderate polarity.

The mobile phase preferably contains a counterion agent. Typical counterion agents include trialkylammonium salts of organic or inorganic acids, such as lower alkyl primary, secondary, and lower tertiary amines, lower trialkyammonium salts and lower quaternary alkyalmmonium salts. Lower alkyl refers to an alkyl radical of one to six carbon atoms, as exemplified by methyl, ethyl, n-butyl, i-butyl, t-butyl, isoamyl, n-pentyl, and isopentyl. Examples of counterion agents include octylammonium acetate, octadimethylammonium acetate, decylammonium acetate, octadecylammonium acetate, pyridiniumammonium acetate, cyclohexylammonium acetate, diethylammonium acetate, propylethylammonium acetate, propyldiethylammonium acetate, butylethylammonium acetate, methylhexylammonium acetate, tetramethylammonium acetate, tetraethylammonium acetate, tetrapropylammonium acetate, tetrabutylammonium acetate, dimethydiethylammonium acetate, triethylammonium acetate, tripropylammonium acetate, tributylammonium acetate, tetrapropylammonium acetate, and tetrabutylammonium acetate.

Although the anion in the above examples is acetate, other anions may also be used, including carbonate, phosphate, sulfate, nitrate, propionate, formate, chloride, and bromide, or any combination of cation and anion. These and other agents are described by Gjerde, et al. in *Ion Chromatography*, 2nd Ed., Dr. Alfred Hüthig Verlag Heidelberg (1987). Counterion agents that are volatile are preferred for use in the method of the invention, with triethylammonium acetate (TEAA) and triethylammonium hexafluoroisopropyl alcohol being most preferred.

MIPC has been successfully applied to the detection of mutations in double stranded DNA by separating heteroduplexes from homoduplexes. Such separations depend on the lower temperature required to denature a heteroduplex at the site of base pair mismatch compared to a fully complementary homoduplex DNA fragment. MIPC, when performed at a temperature which is sufficient to partially denature a heteroduplex is referred to herein as Denaturing Matched Ion Polynucleotide Chromatography (DMIPC). DMIPC is typically performed at a temperature between 52° C. and 70° C. The optimum temperature for performing DMIPC is 54° C. to 59° C.

EXAMPLE 1

Universal Gradient for Mutation Detection Using MIPC

The following Universal Gradient has not been optimized for speed of analysis and can be used for mutation detection for any sample within the size range amenable to MIPC:

| Time (min) | % A | % B | Flow (mL/min) |
|---|---|---|---|
| 0.0 | 65 | 35 | 0.9 |
| 0.1 | 60 | 40 | 0.9 |
| 16.1 | 28 | 72 | 0.9 |
| 16.2 | 0 | 100 | 0.9 |
| 16.7 | 0 | 100 | 0.9 |
| 16.8 | 65 | 35 | 0.9 |
| 18.0 | 65 | 35 | 0.9 |

The mobile phase solutions are prepared from concentrated triethylammonium acetate (100 mL Transgenomic part No. 553301) to give A=0.1 M TEAA, pH 7, B=0.1 M TEAA and 25% acetonitrile. The separation is obtained using a WAVE® DNA Fragment Analysis System (Transgenomic, Inc., San Jose, Calif.) under the following conditions: Column: 50×4.6 mm i.d. containing alkylated poly(styrene-divinylbenzene) beads (DNASEP®, Transgenomic, Inc.); the flow rate is 0.9 mL/min and detection by UV at 260 nm.

EXAMPLE 2

Preparation of a Reference Graph of Mobile Phase vs. Nucleotide Base Pair Length A standard pUC18 HaeIII restriction enzyme digest (Part no. 440582 available from Transgenomic, Inc., San Jose, Calif.) containing DNA fragments having base pair lengths of 80, 102, 174, 257, 267, 298, 434, 458 and 587 was applied to a MIPC column at non-denaturing temperature, 50° C. The column was eluted using the Universal Gradient. The separation (not shown) was obtained using a WAVE® DNA Fragment Analysis System (Transgenomic, Inc., San Jose, Calif.) under the following conditions: Column: 50×4.6 mm i.d. containing alkylated poly(styrene-divinylbenzene) beads (DNASEP®, Transgenomic, Inc.); UV detection was performed at 260 nm. The bp length and retention time (Rt) for each fragment was entered at a computer interface (not shown). A preferred interface is a Column Calibration window which includes a graphical display of Rt vs. bp and/or % B vs. bp. The reference curve 590 shown in FIG. 33 was obtained by fitting the observed data to Equation (i) using a statistical curve fitting routine within the software of the invention.

EXAMPLE 3

Determination of the Dead Time

Using the column and instrumentation as described in Example 2, a method was entered which was a gradient square wave as shown:

| Step | Time | % A | % B | mL/min |
|---|---|---|---|---|
| Loading | 0.0 | 65 | 35 | 0.9 |
| Start Gradient | 0.5 | 65 | 35 | 0.9 |
| Stop Gradient | 2.0 | 65 | 35 | 0.9 |
| Start Clean | 2.1 | 0 | 100 | 0.9 |
| Stop Clean | 5.1 | 0 | 100 | 0.9 |
| Start Equilibrate | 5.2 | 65 | 35 | 0.9 |
| Stop Equilibrate | 8.2 | 65 | 35 | 0.9 |

Next, a 0 μL injection was performed using this gradient. The rise in spectral background was observed at about 4.8 min (not shown). The dead time was obtained by subtracting 2 from this observed rise time. The value of about 2.8 minutes for the dead time was stored in digital memory.

EXAMPLE 4

Description of Temperature Dependent DMIPC Separation Process

This Example refers to FIG. 45 (heteroduplex separations over a 51° to 61° C. temperature range). A mutation standard containing a 209 base pair fragment from the human Y chromosome, locus DYS271 with an A to G mutation at position 168 (part no. 440582 from Transgenomic and as described by Seielstad et al., *Hum. Mol. Genet.* 3:2159 (1994)) was hybridized as recommended by the vendor and the sample was injected onto an MIPC column (50 mm×4.6 mm i.d.) at 51° C. The column was eluted at 0.9 mL/min with a gradient of acetonitrile in 0.1 M TEM over 7 minutes. The chromatography was monitored 260 nm using an UV detector. The heteroduplex present in the mixture was not denatured at 51° C.; therefore, a single peak was observed.

As seen in FIG. 45, the injection and chromatography of the sample was repeated at 10° C. incremental increases in temperature. A shoulder was observed on the low retention time side of the main peak at 53° C. indicating the potential presence of a heteroduplex. At 54° C. three peaks were seen. And at 55°-58° C. four peaks were seen indicating the definite presence of a mutation. The two lower retention time peaks were two heteroduplexes and the higher retention time peaks were homoduplexes.

The instant invention provides an automated system and method, which are simple to use, and which minimize the use of empirical methods to determine optimal mobile phase concentrations and temperatures in the separation of DNA fragments by MIPC.

While the foregoing has presented specific embodiments of the present invention, it is to be understood that these embodiments have been presented by way of example only. It is expected that others will perceive and practice variations which, though differing from the foregoing, do not depart from the spirit and scope of the invention as described and claimed herein.

The invention claimed is:

1. In a method for effecting a base-pair length based separation of a mixture of double-stranded DNA fragments with a high pressure liquid chromatography system comprising mobile phase flow control means for controlling the flow of solvent solution and aqueous components of a mobile phase, the flow control means including computer instruction input means; a Matched Ion Polynucleotide Chromatography separation column; conduit means for directing mobile phase from the mobile phase flow control means to the separation column; and a computer in communication with the mobile phase flow control means having a software mobile phase flow control module resident therein; the computerized steps of:

a) receiving the numerical range of base-pair lengths in the mixture of DNA fragments to be separated;

b) calculating the range of solvent concentrations and corresponding solvent gradient which will effect separation of selected fragments having said range of base-pair lengths, wherein said calculating comprises calibrating said chromatography system and said column with a standard mixture of double-stranded DNA fragments and using said calibration in an algorithm, wherein said algorithm relates the base pair length of DNA fragments in the standard mixture of double-stranded DNA fragments to solvent concentration required to elute the fragments in said standard mixture;

c) providing said range of solvent concentrations and corresponding solvent gradient to the mobile phase flow control module; and d) conducting the separation, wherein the mobile phase flow control module controls the settings of the mobile phase flow control means to effect said range of solvent concentrations and corresponding solvent gradient required to effect separation of the selected fragments.

2. The method of claim 1 wherein the mobile phase flow control means of step d) are a set of flow control valves, each with automatic opening controls responsive to control commands from the flow control module.

3. The method of claim 1 wherein the mobile phase flow control means of step d) are a set of pumps, the flow settings of which are responsive to control commands from the flow control module.

4. The method of claim 1 wherein the separation of the selected fragments of step d) is a separation of all of the fragments of the mixture of DNA fragments.

5. The method of claim 1 wherein the separation of the selected fragments of step d) is a separation of one or more fragments of the mixture of DNA fragments.

6. The method of claim 1 wherein the gradient of step c) includes an isocratic gradient.

7. The method of claim 1 wherein the range of solvent concentrations of step c) begins below the value of % B calculated for the smallest fragment in said mixture of DNA fragments to be separated and ends above the value of % B calculated for the largest fragment in said mixture of DNA fragments to be separated, wherein % B is the percentage in the mobile phase of an aqueous solution containing organic solvent; wherein said % B is calculated by a linear, hyperbolic, quadratic or cubic formula using constants obtained in the calibration of step b).

8. The method of claim 1 wherein the range of solvent concentrations of step c) begins below the value of % B calculated for the smallest fragment in said mixture of DNA fragments to be separated and ends above the value of % B calculated for the largest fragment in said mixture of DNA fragments to be separated, wherein % B is calculated by the following formula:

$$\% B = p_1 + \frac{p_2 \cdot bp}{p_3 + bp}$$

wherein % B is the percentage in the mobile phase of an aqueous solution containing organic solvent;
bp is the base pair length of a DNA fragment; and
$p_1$, $p_2$ and $p_3$ are constants obtained by calibration of the chromatography system and separation column for the selected solvent with said standard mixture of double-stranded DNA fragments, wherein said calibration comprises relating the base pair length of DNA fragments in said standard mixture of double-stranded DNA fragments to the % B required to elute the fragments in said standard mixture.

9. The method of claim 1 wherein the range of solvent concentrations of step c) begins below the value of % B calculated for the smallest fragment in said mixture of DNA fragments to be separated and ends above the value of % B calculated for the largest fragment in said mixture of DNA fragments to be separated, wherein % B is calculated by the following formula:

$$\% B = \frac{1}{k} \ln\left[\frac{\exp(s \cdot d \cdot k) - 1}{\text{void}}\right] + \text{offset}$$

wherein $$k = p_4 \cdot bp + p_5;$$

$$\text{offset} = p_6 + \frac{p_7 \cdot bp}{p_8 + bp};$$

wherein
% B is the percentage in the mobile phase of an aqueous solution containing organic solvent;
bp is the base pair length of a DNA fragment;
s is the slope of the gradient;
d, void, $p_4$, $p_6$, $p_7$, and $p_8$ are constants obtained by calibrating the chromatography system and separation column for the selected solvent with said standard mixture of double-stranded DNA fragments, wherein said calibration comprises relating the base pair length of DNA fragments in said standard mixture of double-stranded DNA fragments to the % B required to elute the fragments in said standard mixture; and
wherein
d=2.0;
void=1.95;
$p_4 = 9.596 \times 10^{-4}$;
$p_5 = 0.417$;
$p_6 = 25.4$;
$p_7 = 45.2$; and,
$p_8 = 85.0$.

10. A high pressure liquid chromatography system including a computerized control means, the chromatography system comprising mobile phase flow control means for controlling the flow of solvent solution and aqueous components of a mobile phase, the flow control means including computer instruction input means; a Matched Ion Polynucleotide Chromatography separation column; conduit means for directing mobile phase from the mobile phase flow control means to the separation column; and a computer in communication with the mobile phase flow control means; a software mobile phase flow control module in working association with the computer and the mobile phase flow control means, wherein the mobile phase flow control means are a set of flow control valves, each with automatic opening controls responsive to control commands from the flow control module or the mobile phase control means is a set of pumps, the flow settings of which are responsive to control commands from the flow control module, said computer including solvent concentration and gradient computing software for computing the solvent gradient and beginning and ending solvent concentrations for the separation of double-stranded DNA fragments.

11. The high pressure liquid chromatography system of claim 10 wherein the solvent concentration and gradient computing software comprises software means for receiving the range of fragment base pair lengths to be separated in a mixture of double-stranded DNA fragments and calculating the solvent concentration to begin below the value of % B calculated for the smallest fragment in said mixture of DNA fragments to be separated and to end above the value of % B calculated for the largest fragment in said mixture of DNA fragments to be separated, wherein said % B is the percentage in the mobile phase of an aqueous solution containing organic solvent, wherein said % B is calculated by a linear, hyperbolic, quadratic or cubic formula using constants which are obtained by calibrating the chromatography system and separation column for the selected solvent with a standard mixture of double-stranded DNA fragments, wherein said calibration comprises relating the base pair length of DNA fragments in a standard mixture of double-stranded DNA fragments to the % B required to elute the fragments in said standard mixture.

12. The high pressure liquid chromatography system of claim 10 wherein the solvent concentration and gradient computing software comprises software means for receiving the range of fragment base pair lengths to be separated in a mixture of double-stranded DNA fragments and calculating the solvent concentration to begin below the value of % B calculated for the smallest fragment to be separated and to end above the value of % B calculated for the largest fragment to be separated, wherein % B is calculated by the following formula:

$$\% B = p_1 + \frac{p_2 \cdot bp}{p_3 + bp};$$

wherein
bp is the base pair length of a DNA fragment
% B is the percentage in the mobile phase of an aqueous solution containing organic solvent; and
$p_1$, $p_2$ and $p_3$ are constants obtained by calibrating the chromatography system and separation column for the selected solvent with a standard mixture of DNA fragments, wherein said calibration comprises relating the base pair length of DNA fragments in said standard mixture of double-stranded DNA fragments to the % B required to elute the fragments in a standard mixture.

13. The high pressure liquid chromatography system of claim 10 wherein the solvent concentration and gradient computing software comprises software means for receiving the range of fragment base pair lengths to be separated in a mixture of double-stranded DNA fragments and calculating the solvent concentration to begin below the value of % B calculated for the smallest fragment to be separated and to end above the value of % B calculated for the largest fragment to be separated, wherein % B is calculated by the following formula:

$$\% B = \frac{1}{k} \ln\left[\frac{\exp(s \cdot d \cdot k) - 1}{\text{void}}\right] + \text{offset}$$

wherein $$k = p_4 \cdot + p_5;$$

$$\text{offset} = p_6 + \frac{p_7 \cdot bp}{p_8 + bp};$$

% B is the percentage in the mobile phase of an aqueous solution containing organic solvent;

bp is the base pair length of a DNA fragment;

s is the slope of the gradient;

d, void, $p_4$, $p_5$, $p_6$, $p_7$, and $p_8$ are constants obtained by calibrating the chromatography system and separation column for the selected solvent with said standard mixture of double-stranded DNA fragments, wherein said calibration comprises relating the base pair length of DNA fragments in a standard mixture of double-stranded DNA fragments to the % B required to elute the fragments in said standard mixture; and wherein d=2.0;

void=1.95;

$p_4 = 9.596 \times 10^{-4}$;

$p_5 = 0.417$;

$p_6 = 25.4$;

$p_7 = 45.2$; and, $p_8 = 85.0$.

14. A computer-readable medium encoded with a software program implementing a method comprising receiving a range of base pair lengths to be separated from a mixture of double-stranded DNA fragments, calculating solvent concentrations required to separate the range of base pair lengths to be separated by Matched Ion Polynucleotide Chromatography, and selecting the solvent gradient to be used to separate the range of base pair lengths to be separated by Matched Ion Polynucleotide Chromatography, wherein the step of calculating said solvent concentrations includes calculating the solvent concentration to begin below the value of % B calculated for the smallest fragment in said mixture to be separated and to end above the value of % B calculated for the largest fragment in said mixture to be separated, wherein % B is the percentage in the mobile phase of an aqueous solution containing organic solvent, wherein said % B is calculated by a linear, hyperbolic, quadratic or cubic formula using constants which are obtained by calibrating the chromatography system and separation column for the selected solvent with a standard mixture of double-stranded DNA fragments.

15. The computer-readable medium of claim 14, wherein % B is calculated by the following formula:

$$\% B = p_1 + \frac{p_2 \cdot bp}{p_3 + bp}$$

wherein bp is the base pair length of a DNA fragment; and $p_1$, $p_2$ and $p_3$ are constants obtained by calibrating the chromatography system and separation column for the selected solvent with a standard mixture of DNA fragments, wherein said calibration comprises relating the base pair length of DNA fragments in a standard mixture of double-stranded DNA fragments to the % B required to elute the fragments in said standard mixture.

16. The computer-readable medium of claim 14 wherein % B is calculated by the following formula:

$$\% B = \frac{1}{k} \ln\left[\frac{\exp(s \cdot d \cdot k) - 1}{\text{void}}\right] + \text{offset}$$

wherein $$k = p_4 \cdot bp + p_5;$$

$$\text{offset} = p_6 + \frac{p_7 \cdot bp}{p_8 + bp};$$

bp is the base pair length of a DNA fragment;

s is the slope of the gradient;

d, void, $p_4$, $p_5$, $p_6$, $p_7$, and $p_8$ are constants obtained by calibrating the chromatography system and separation column for the selected solvent with said standard mixture of double-stranded DNA fragments, wherein said calibration comprises relating the base pair length of DNA fragments in a standard mixture of double-stranded DNA fragments to the % B required to elute the fragments in said standard mixture; and wherein d=2.0;

void=1.95;

$p_4 = 9.596 \times 10^{-4}$;

$p_5 = 0.417$;

$p_6 = 25.4$;

$p_7 = 45.2$; and, $p_8 = 85.0$.

17. In a method for effecting a separation of equal length heteroduplex and homoduplex DNA molecules in a mixture, with a high pressure liquid chromatography system comprising mobile phase flow control means for controlling the flow of solvent solution and aqueous components of a mobile phase, the flow control means including computer instruction input means; a Matched Ion Polynucleotide Chromatography separation column; conduit means for directing mobile phase from the mobile phase flow control means to the separation column; and a computer in communication with the mobile phase flow control means having a software mobile phase flow control module resident therein; the computerized steps of:

a) receiving the numerical value of the base-pair length of a double-stranded DNA molecule having the length of a homoduplex or heteroduplex molecule in the mixture;

b) calculating a solvent concentration which will effect elution of a molecule having said base-pair length from said column under non-denaturing conditions, wherein said calculating comprises calibrating said chromatography system and said column with a standard mixture of double-stranded DNA fragments and using said calibration in an algorithm, wherein said algorithm relates the base pair length of DNA fragments in the standard mixture of double-stranded DNA fragments to solvent concentration required to elute the fragments in said standard mixture;

c) calculating a range of solvent concentrations and corresponding mobile phase gradient to begin below a solvent concentration that will elute said double-stranded DNA molecule and to end above a solvent concentration that will elute said double-stranded DNA molecule;

d) providing said range of solvent concentrations and corresponding mobile phase gradient to the mobile phase flow control module; and e) conducting the separation under conditions effective to partially denature said heteroduplexes, wherein the mobile phase flow control module controls the settings of the mobile phase flow control means to effect said range of solvent concentrations and corresponding mobile phase gradient to effect separation of said homoduplex and said heteroduplex molecules.

18. The method of claim 17 wherein the mobile phase flow control means of step e) are a set of flow control valves, each with automatic opening controls responsive to control commands from the flow control module.

19. The method of claim 17 wherein the mobile phase flow control means of step e) are a set of pumps, the flow setting of which are responsive to control commands from the flow control module.

20. The method of claim 17 wherein the gradient of step d) includes an isocratic gradient.

21. The method of claim 17 wherein the range of solvent concentrations of step d) begins below the value of % B calculated for a DNA molecule having said base-pair length and ends above the value of % B calculated for a DNA molecule of said base-pair length, wherein said % B is the percentage in the mobile phase of an aqueous solution containing organic solvent, wherein said % B is calculated by a linear, hyperbolic, quadratic or cubic formula using constants obtained in the calibration of step b).

22. A denaturing high pressure liquid chromatography system including a computerized control means, the chromatography system comprising mobile phase flow control means for controlling the flow of solvent solution and aqueous components of a mobile phase, the flow control means including computer instruction input means; a Matched Ion Polynucleotide Chromatography separation column; conduit means for directing mobile phase from the mobile phase flow control means to the separation column; and a computer in communication with the mobile phase flow control means; a software mobile phase flow control module in working association with the computer and the mobile phase flow control means, wherein the mobile phase flow control means are a set of flow control valves, each with automatic opening controls responsive to control commands from the flow control module or the mobile phase control means is a set of pumps, the flow settings of which are responsive to control commands from the flow control module, said computer including solvent concentration and gradient computing software for computing the solvent gradient and beginning and ending solvent concentrations for the separation of equal length heteroduplex and homoduplex DNA molecules in a mixture.

23. The high pressure liquid chromatography system of claim 22 wherein the solvent concentration and gradient computing software comprises software means for receiving the base-pair length of a homoduplex or a heteroduplex molecule in said mixture and calculating the solvent concentration to begin below the value of % B calculated for a DNA molecule having said base-pair length and to end above the value of % B calculated for a DNA molecule of said base-pair length, wherein % B is the percentage in the mobile phase of an aqueous solution containing organic solvent, wherein said % B is calculated by a linear, hyperbolic, quadratic or cubic formula using constants which are obtained by calibrating the chromatography system and separation column for the selected solvent with a standard mixture of double-stranded DNA fragments.

24. A computer-readable medium encoded with a software program implementing a method comprising receiving the base pair length of equal length heteroduplex and homoduplex DNA molecules in a mixture to be separated, calculating a solvent concentration required to elute a DNA molecule having said base-pair length by Matched Ion Polynucleotide Chromatography, and selecting the solvent gradient to be used to separate said heteroduplex and homoduplex DNA molecules under partially denaturing conditions, wherein the step of calculating said solvent concentration includes calculating the solvent concentration to begin below the value of % B calculated for a DNA molecule having said base-pair length and is calculated to end above the value of % B calculated for a DNA molecule of said base-pair length, wherein % B is the percentage in the mobile phase of an aqueous solution containing organic solvent, wherein said % B is calculated by a linear, hyperbolic, quadratic or cubic formula using constants which are obtained by calibrating the chromatography system and separation column for the selected solvent with a standard mixture of DNA fragments.

25. The computer-readable medium of claim 24, wherein % B is calculated by the following formula:

$$\% B = p_1 + \frac{p_2 \cdot bp}{p_3 + bp};$$

wherein bp is the base pair length of a DNA fragment; and $p_1$, $p_2$ and $p_3$ are constants obtained by calibrating the chromatography system and separation column for the selected solvent with a standard mixture of DNA fragments, wherein said calibration comprises relating the base pair length of DNA fragments in a standard mixture of double-stranded DNA fragments to the % B required to elute the fragments in said standard mixture.

26. The computer-readable medium of claim 24 wherein % B is calculated by the following formula:

$$\% B = \frac{1}{k} \ln\left[\frac{\exp(s \cdot d \cdot k) - 1}{\text{void}}\right] + \text{offset}$$

wherein $$k = p_4 \cdot bp + p_5;$$

$$\text{offset} = p_6 + \frac{p_7 \cdot bp}{p_8 + bp};$$

s is the slope of the gradient;
bp is the base pair length of a DNA fragment;
d, void, $p_4$, $p_5$, $p_6$, $p_7$, and $p_8$ are constants obtained by calibrating the chromatography system and separation column for the selected solvent with a standard mixture of double-stranded DNA fragments, wherein said calibration comprises relating the base pair length of DNA fragments in a standard mixture of double-stranded DNA fragments to the % B required to elute the fragments in said standard mixture; and
wherein
d=2.0;
void=1.95;
$p_4 = 9.596 \times 10^{-4}$;
$p_5 = 0.417$;
$p_6 = 25.4$;
$p_7 = 45.2$; and,
$p_8 = 85.0$.

27. In a method for effecting a separation of equal length heteroduplex and homoduplex DNA molecules in a mixture, with a high pressure liquid chromatography system comprising a Matched Ion Polynucleotide Chromatography separation column; mobile phase flow control means for controlling the flow of solvent solution and aqueous components of a mobile phase, the flow control means including computer instruction input means; conduit means for directing mobile phase from the mobile phase flow control means to the separation column; oven temperature control means for controlling the temperature of mobile phase entering the separation column, the oven temperature control means including computer instruction input means; and a computer in communication with the mobile phase flow control means having a software mobile phase flow control module resident therein; said computer in communication with the oven temperature control means having an oven temperature control software module resident therein; the method comprising the computerized steps of:

a) receiving the numerical value of the base-pair length of a double-stranded DNA molecule having the length of a homoduplex or heteroduplex molecule in the mixture;

b) calculating a % B which will effect elution of a double-stranded DNA molecule having said base-pair length from said column under non-denaturing conditions, wherein said calculating comprises calibrating said chromatography system and said column with a standard mixture of double-stranded DNA fragments and using said calibration in an algorithm, wherein said algorithm relates the base pair length of the standard mixture of double-stranded DNA fragments to the % B required to elute the fragments in said standard mixture, wherein % B is the percentage in the mobile phase of an aqueous solution containing organic solvent;

c) calculating a range of % B and corresponding mobile phase gradient to begin below the value of % B that will elute said double-stranded DNA molecule having said base-pair length and to end above a value of % B that will elute said double-stranded DNA molecule having said base-pair length;

d) providing said range of % B and corresponding mobile phase gradient to the mobile phase flow control module;

e) receiving a predicted heteromutant site separation temperature; heating said mixture of DNA molecules to said predicted heteromutant site separation temperature; and f) conducting the separation, wherein the mobile phase flow control module controls the settings of the mobile phase flow control means to effect said range of % B and corresponding mobile phase gradient required to effect separation of the homoduplex and heteroduplex fragments by Denaturing Matched Ion Polynucleotide Chromatography at the predicted heteromutant site separation temperature to identify the presence of any heteromutant site separated components in the mixture.

* * * * *

SEQUENCE LISTING

```
<160> NUMBER OF SEQ ID NOS: 1

<210> SEQ ID NO 1
<211> LENGTH: 209
<212> TYPE: DNA
<213> ORGANISM: Homo sapiens
<220> FEATURE:
<221> NAME/KEY: STS
<222> LOCATION: (1)...(209)
<223> OTHER INFORMATION: sY81

<400> SEQUENCE: 1
aggcactggt cagaatgaag tgaatggcac acaggacaag tccagaccca ggaaggtcca       60
gtaacatggg agaagaacgg aaggagttct aaaattcagg gctcccttgg gctccsctgt      120
ttaaaaatgt aggttttatt attatatttc attgttaaca aaagtccgtg agatctgtgg     180
aggataaagg gggagctgta ttttccatt                                        209
```